(12) United States Patent
Vogel et al.

(10) Patent No.: US 6,864,404 B1
(45) Date of Patent: Mar. 8, 2005

(54) ENGINEERING DISEASE RESISTANCE WITH PECTATE LYASE-LIKE GENES

(75) Inventors: John Vogel, Sunnyvale, CA (US); Shauna Somerville, Portola Valley, CA (US)

(73) Assignee: Carnegie Institution of Washington, Washington, DC (US)

( * ) Notice: Subject to any disclaimer, the term of this patent is extended or adjusted under 35 U.S.C. 154(b) by 243 days.

(21) Appl. No.: 09/684,960

(22) Filed: Oct. 10, 2000

Related U.S. Application Data

(60) Provisional application No. 60/159,566, filed on Oct. 15, 1999.

(51) Int. Cl.[7] .................... C12N 15/09; C12N 15/29; C12N 15/82; A01H 5/00
(52) U.S. Cl. .................... 800/279; 800/278; 800/306; 800/320; 800/317; 800/298; 435/320.1; 435/419; 435/468; 536/23.6
(58) Field of Search .................. 800/278, 279, 800/306, 320, 298, 317; 435/419, 468; 320.1, 420; 536/23.6, 23.2

(56) References Cited

PUBLICATIONS

Bork, "Powers and Pitfalls in Sequence Analysis: The 70% Hurdle", 2000, Genome Research vol. 10, pp. 398–400.*
Linthorst et al, Constitutive Expression of Pathogenesis–Related Proteins PR–1, GRP amd PR–S in Tobacco Has No Effect on Virus Infection, 1989, The Plant Cell vol. 1, pp. 285–291.*
Ryals et al, "Systemic Acquired Resistance", 1996, The Plant Cell, vol. 8, pp. 1809–1819.*
Lacombe et al, "The Identity of Plant Glutamate Receptors", 2001, Science vol. 292, pp. 1486–1487.*

Profile Order: Erysiphales (Powdery Mildews) Alan J. Silverside (Apr. 2001), Biological Sciences, University of Paisley Biodiversity Reference.
Van Custem et al., 1994, Acta Bot. Neerl. 43(3), p. 231–245.
Taniguchi et al., 1995, Allergy, 50: 90–93.
Bechtold et al., 1993, C.R. Acad. Sci. Paris, Sciences de la vie/Life Sciences, 316: 1194–1199.
Dircks et al., 1996, Plant Physiol. Biochem, 34(4): 509–520.
Vogel et al., 2002, The Plant Cell, 14: 2095–2106.
Eckardt, 2002, The Plant Cell, 14: 1983–1986.
Barras, 1994, Annu. Rev. Phytopathol, 32: 201–234.
Domingo et al., 1998, The Plant Journal, 13(1): 17–28.
Medina–Escobar et al., 1997, Plant Molecular Biology, 34: 867–877.
Adam et al., 1996, The Plant Journal, 9(3): 341–356.
Edwards et al., 1991, Nucleic Acids Research, 19(6): 1349.
Bowling et al., 1997, The Plant Cell, 9: 1573–1584.
Jorgensen, 1994, Critical Reviews in Plant Sciences, 13(1) 97–119.
Ryals et al., 1996, The Plant Cell, 8: 1809–1819.
Moerschbacher et al., 1999, Journal of Experimental Botany, 50(334): 605–612.

* cited by examiner

*Primary Examiner*—Elizabeth F. McElwain
*Assistant Examiner*—Medina A. Ibrahim
(74) *Attorney, Agent, or Firm*—Morgan, Lewis & Bockius

(57) ABSTRACT

A mutant gene coding for pectate lyase and homologs thereof is provided, which when incorporated in transgenic plants effect an increased level disease resistance in such plants. Also is provided the polypeptide sequence for the pectate lyase of the present invention. Methods of obtaining the mutant gene, producing transgenic plants which include the nucleotide sequence for the mutant gene and producing improved disease resistance in a crop of such transgenic plants are also provided.

12 Claims, 16 Drawing Sheets

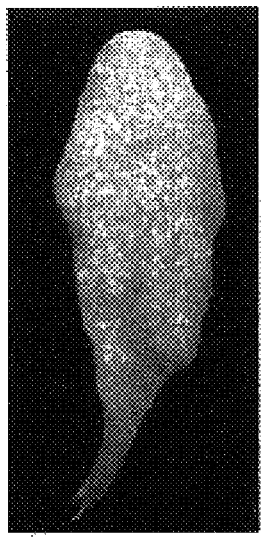 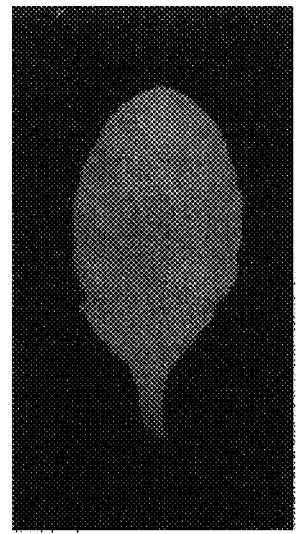 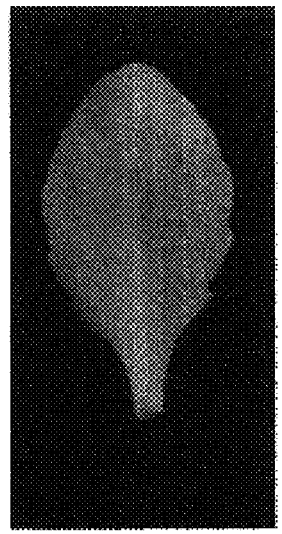
COLUMBIA     pmr5     pmr6
FIG. 1A-1     FIG. 1A-2     FIG. 1A-3
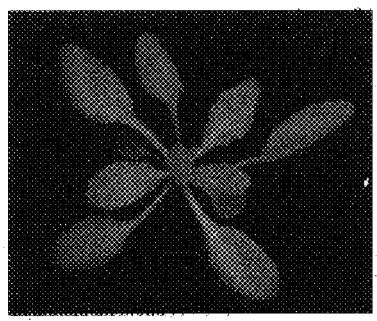 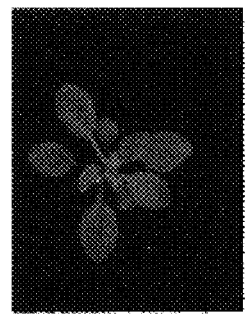 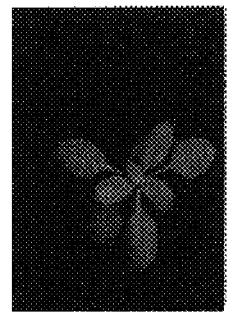
COLUMBIA     pmr5     pmr6
FIG. 1B-1     FIG. 1B-2     FIG. 1B-3

COLUMBIA pmr5 pmr6

COLUMBIA pmr5 pmr6 cgatttgcaggtatacaagttactcggcaatatgtttggcttctccggatatgaagaataaataacctccagctcacgcaggcagtgagaaact gctataacaacccacatcttgatattctcaggtgtgcattttgaatcaattaagtaaagacggaagctttctataaccggagctctatgtaatggc agatttttgtcaagaaaacactccaacctcttgcattcagaagaatctctatgaccatacttaagtttaggcaaccacatccaaagatactcccat cttttcgacaaaatgctagtggatacagcaattttgttggaacaaacaataatatcttaataagcacttcatcagataactcactgaatctatccat atcttgaaacccgaaacccccaagttactgttgttactgtcgacagaacttgggaccctaataagaaagaagataacatctttcaggctcataaa gctaaagaagccaattagtaaacaagtgaaaactcggacacaaagaggaacagtactaaaccttagaaacaagctagattgttaggtgaag ctgagaaattttcagtgcccaaagaactgtatatccttttcaaatctagtagaatggtagtctgaactaggaatcaagaaagggtaaatgtaaac gaagcttgaatggtacatagcaaggaaaaaggaatatgaacaagttggtttatcagaagataccacaatcgctgagcatcggaacgacaaa gtgttgtcctcaccgttgatactcacactggccactgacccactcatcaaagcgttcggcgtccatttaatttaggtgtttaattaccataaacga tgggcctggttatgggcctaacttttatgttatacgcccatttaacttgggtgtttaattacaaacttgctttagcgacgactttgacgagaaatga gaggcccaatataaaatacgagcttgcttaccaaaatttgagacccaaatagtaaaccaatctcctccagaatgcaagtggacacaaatccc caagagaaacagaatcaaaatctcaagaaaacctattagccctgtttccagcaagagggcagagaagcagagagagagagagtgtgaga gagaaagcagcttcttcttcttctcctcctcttctcccttatgtggatttcaaatccttctctgctactctctcttcacatttctctaccaacattcttctt ctgacactcaacacacacactgcaacttccacagctaaatctagcaacaccaagtcaaaatccgccactaacgATGCTTCTTCAA

AACTTCTCCAACACCATTTTCCTTCTCTGCCTCTTCTTCACACTCCTCTCCGCCACTAA

ACCCCTAAATCTCACTCTCCCTCACCAACACCCTTCCCCTGATTCCGTCGCTCTCCAT

GTCATCAGgtaaacaaaagctcctccctctctcattacacatttttcccagataaaataaaaactcaaactttcttctccgaaattcacag

GAGTGTAAATGAATCTCTTGCAAGAAGACAACTAAGCTCACCATCATCATCCTCATC

FIG. 5A-1

ATCATCATCCTCCTCATCATCATCCTCTTGCCGTACCGGAAACCCAATCGACGATTG
CTGGAGATGCAGCGACGCAGACTGGTCAACAAACCGACAAAGACTAGCAGACTGTT
CAATCGGCTTCGGACACGGCACACTCGGAGGCAAAAACGGCAAGATCTACGTCGTA
ACTGACTCATCCGACAACAACCCAACAAACCCAACACCAGGGACACTCCGTTACGG
CGTAATCCAAGAAGAGCCACTCTGGATCGTCTTCTCTTCAAACATGCTCATCAGACT
AAAACAAGAACTCATCATCAACAGCTACAAAACCTTAGATGGTCGTGGCTCAGCCG
TTCACATTACCGGAAACGGTTGCTTAACTCTCCAATACGTTCAACACATCATCATCC
ACAACCTCCATATCTATGACTGTAAACCTTCAGCTGGATTCGAGAAACGTGGTAGAT
CCGATGGAGATGGGATCTCGATCTTCGGATCTCAGAAGATCTGGGTTGATCATTGTT
CAATGAGTCATTGCACCGACGGGCTAATTGATGCTGTGATGGGTTCTACAGCTATAA
CTATATCTAACAATTACTTCACCCACCACGACGAGGTTATGTTGTTGGGTCATGATG
ATAACTATGCTCCTGATACGGGGATGCAAGTGACGATAGCGTTTAATCATTTCGGAC
AAGGGCTTGTTCAGAGGATGCCTAGGTGTCGGAGAGGTTACATTCATGTAGTGAATA
ATGATTTCACTGAGTGGAAAATGTATGCTATTGGTGGTAGTGGTAATCCCACCATTA
ACAGTCAAGGAAATCGTTACTCTGCTCCTTCTGATCCTAGCGCCAAAGAGgtattttccttt
tatataacaaattttacatttttttggattacccatatagaaatatctttcctttttgttgttgttgttatatggtgtggaacactttctttagtagcttaactt
tgtagggtttagtatgatttgtggatagattttaggcttttaccatagagaacttttttattgagtaattgacaaatgtgtagttttcattagttgatttg
attgggttgtaaaatgttttgagtatggtcctatcttctatgaatccagttcatatttcacatggacagttgttaatctttagctagtaggaaaaaatat
ccagttaaagttgtatgtaaatgggaaaaggaagaatcttattttttatgagaattgggtctacgaggagtgagacagtgatggtatgtatgtata
gtattataagtgcatgacagacatgtgggctgcttcttctacttcttctctgtccacacactttatttgttgttgttagttgtttgaataccaccacgc
gcaacgacggcgcgtggaaaagagattgtttgctgatcggtggtgaaaagcagGTGACGAAGCGAGTGGACTCGA
AGGACGATGGTGAATGGTCGAATTGGAATTGGAGAACAGAAGGGGATTTGATGGAG
AATGGAGCTTTCTTTGTGGCCTCTGGTGAAGGAATGAGCTCAATGTACTCTAAAGCT

FIG. 5A-2

TCTAGTGTTGACCCTAAAGCTGCTTCTCTCGTAGACCAGCTCACTCGAAACGCTGGC

GTTTTTGGCGGTCCCAGgtactatttcttttttcccttttacccttctttatttctaattagattttatttaaccaatttaaaagtatactc ccttattagaaaaatcttttaaaaactgaagcatgatctctcatttcggtgtttaatgtataataaaattagctgtgaaagcgcgtgattagagcgc atgatttgttattgtcgttattcgttaagtcaagaacagataacaaccgtactattttactattttagttgtgtttagtctttactttggagtctagttaa cttgtgattagaaaaagaaaactctaaactgacgaatttgtaatttcttattggaaaataggataaataggttctttcttgtttgaggttcttaatcac attctatattcattcattcaattattcttgaaatggtgatatatagaagaggaactatggtaagtctgaataattagaatctgtataaacaattaaagt gacacattattggtttatttgaaaaagtagctcattgagaatatcagacgttagggttttggcagtattccagaattcatgtagagtcgcacgtga ttgtctacttagggaaccgaccaacttgactagtgtctgaattaaccccacttgctatttcattttgcattattttcaagttttagattgcatcattt ttgttgtccctttgggattatgggtggtggaaatgtctgtcttaatgttaattaagacatgcatgatcatgatgcaaactacattttgatacatcaaat gtaatttactatacaaaagccaataggttttttggtcgtaatgatgtcattatgatggaaatgtggaggttaaggacgattgggacccttaccta gaaagatgattccttttctatggatccataataataattacaagtccttttaaatcgcattaattgtatccttttgactttgtttagctagaatgaataa tatcgtataacttctaatgagatggttttggtggggttagGGATGATCAAGGTCAGAGTGGCAATTCTTACTC

TCCTTATGGAGGCGACGGCGGTGGCGGTGGGAGCAGCGGTGGGAGCAGCGGTGGAG

GGATGGACGTTATGGGAGGTACGACGAGAGGAAGCAGCAGCAGCGGCGATGA

CAGCAATGTCTTCCAGATGATATTTGGAAGCGATGCACCGTCTCGGCCGCGTTTAAC

GTTATTGTTTTCTTTGTTAATGATTTCGGTTTTGTCGTTATCAACTCTATTATTGTGAcg aatggataacaaataggatttggaccgttcaattgattggttttggtgtaaagtgtggctctctctccattatttctttaattgtagttggattggca acaatacaaaacactaaaatgggattgtcaaggcaacgtcaaagacgaactttgtctcatccaatcaaatgctttgtttcatcaatgatgtagca ttctcatctttctatgtccactacctttattcctctaacgaaaattaaggttgtgtagaagtcacatttttaatatagcaaaatttgccgcatgaaaaa gcttcttcaagtgatgctaatagcgagttttccatcggttgagaagtctgagatagagagaatcatcagagagaaggcgacaagggttgcgg aaggaggagaggaagagaatgttatggcaaaacgattgtctaaagaagctatttcaaatgcagatgaaggatcttgagttcattcaacaaca aaacatagagccttaacaatataggttgcaatggccaaacatgtttcttttttccagtccggattataaaaagaaggatttaactttta tttcaaatccttctctgctactctctcttcacatttctctaccaacattcttcttctgacactcaacacacacactgcaacttccacagctaaatctag caacaccaagtcaaaatccgccactaacgATGCTTCTTCAAAACTTCTCCAACACCATTTTCCTTCTCT

GCCTCTTCTTCACACTCCTCTCCGCCACTAAACCCCTAAATCTCACTCTCCCTCACCA

ACACCCTTCCCCTGATTCCGTCGCTCTCCATGTCATCAGGAGTGTAAATGAATCTCTT

GCAAGAAGACAACTAAGCTCACCATCATCATCCTCATCATCATCATCCTCCTCATCA

TCATCCTCTTGCCGTACCGGAAACCCAATCGACGATTGCTGGAGATGCAGCGACGCA

GACTGGTCAACAAACCGACAAAGACTAGCAGACTGTTCAATCGGCTTCGGACACGG

CACACTCGGAGGCAAAAACGGCAAGATCTACGTCGTAACTGACTCATCCGACAACA

ACCCAACAAACCCAACACCAGGGACACTCCGTTACGGCGTAATCCAAGAAGAGCCA

CTCTGGATCGTCTTCTCTTCAAACATGCTCATCAGACTAAAACAAGAACTCATCATC

AACAGCTACAAAACCTTAGATGGTCGTGGCTCAGCCGTTCACATTACCGGAAACGGT

TGCTTAACTCTCCAATACGTTCAACACATCATCATCCACAACCTCCATATCTATGACT

GTAAACCTTCAGCTGGATTCGAGAAACGTGGTAGATCCGATGGAGATGGGATCTCG

ATCTTCGGATCTCAGAAGATCTGGGTTGATCATTGTTCAATGAGTCATTGCACCGAC

GGGCTAATTGATGCTGTGATGGGTTCTACAGCTATAACTATATCTAACAATTACTTC

ACCCACCACGACGAGGTTATGTTGTTGGGTCATGATGATAACTATGCTCCTGATACG

GGGATGCAAGTGACGATAGCGTTTAATCATTTCGGACAAGGGCTTGTTCAGAGGAT

GCCTAGGTGTCGGAGAGGTTACATTCATGTAGTGAATAATGATTTCACTGAGTGGAA

AATGTATGCTATTGGTGGTAGTGGTAATCCCACCATTAACAGTCAAGGAAATCGTTA

CTCTGCTCCTTCTGATCCTAGCGCCAAAGAGGTGACGAAGCGAGTGGACTCGAAGG

ACGATGGTGAATGGTCGAATTGGAATTGGAGAACAGAAGGGGATTTGATGGAGAAT

GGAGCTTTCTTTGTGGCCTCTGGTGAAGGAATGAGCTCAATGTACTCTAAAGCTTCT

FIG. 5B-1

AGTGTTGACCCTAAAGCTGCTTCTCTCGTAGACCAGCTCACTCGAAACGCTGGCGTT

TTTGGCGGTCCCAGGGATGATCAAGGTCAGAGTGGCAATTCTTACTCTCCTTATGGA

GGCGACGGCGGTGGCGGTGGGAGCAGCGGTGGGAGCAGCGGTGGAGGGATGGACG

TTATGGAGGTACGACGAGAGGAAGCAGCAGCAGCAGCGGCGATGACAGCAATGT

CTTCCAGATGATATTTGGAAGCGATGCACCGTCTCGGCCGCGTTTAACGTTATTGTTT

TCTTTGTTAATGATTTCGGTTTTGTCGTTATCAACTCTATTATTGTGAcgaatggataacaaata ggatttggaccgttcaattgattggttttgg

FIG. 5B-2

MLLQNFSNTIFLLCLFFTLLSATKPLNLTLPHQHPSPDSVALHVIRSVNESLARRQLSSPSS
SSSSSSSSSSSSCRTGNPIDDCWRCSDADWSTNRQRLADCSIGFGHGTLGGKNGKIYVVT
DSSDNNPTNPTPGTLRYGVIQEEPLWIVFSSNMLIRLKQELIINSYKTLDGRGSAVHITGN
GCLTLQYVQHIIIHNLHIYDCKPSAGFEKRGRSDGDGISIFGSQKIWVDHCSMSHCTDGLI
DAVMGSTAITISNNYFTHHDEVMLLGHDDNYAPDTGMQVTIAFNHFGQGLVQRMPRC
RRGYIHVVNNDFTEWKMYAIGGSGNPTINSQGNRYSAPSDPSAKEVTKRVDSKDDGEW
SNWNWRTEGDLMENGAFFVASGEGMSSMYSKASSVDPKAASLVDQLTRNAGVFGGPR
DDQGQSGNSYSPYGGDGGGGGSSGGSSGGGMDVMGGTTRGSSSSSGDDSNVFQMIFGS
DAPSRPRLTLLFSLLMISVLSLSTLLL.

FIG. 5C ctcttgaaagctctgatggcgggaaacaaaggttggatgagaatctgaaaaggttggtactgtgtgatgatgaatttgccgtattgaatcccat cgaagaatgggtagaagtaacagacggctgagattatccgatccgatgcatcgacggaatcatcacccttggattggagtacgagtgtggc ggctctgtccctggaaagtctaggttttgggaattgggtatcaaggtttagagggagaaaagaacgaccggttagggttagggttccggtga gagatggtaatggagcaaaaaaactgagatattattgccatttttgctctgtttttgtttcacttcacacaaaactgaaagactgcttaacacatgatg agaggataataaactaaactccactctgttttaaaagtttagcttaaaacattgtgtcgtcttcttatctttctaatatgataaaacggtacgtagtta tttgaagtaaggtaacaattaaatagcctctgttattgtctttgtttttttgtgtatatttaaatatcaaaatccaccggtataaaacggcgtaatgcctt tgtattggacccaattctttcaattttcacctaatttaattacctccgtatttatttttagtgcacttcaatgtctcttgcatatatatattggagcaaatt ataaacataATGTTCATAGTGAAATTGTTAGTTGGTTTTAATCTCTTTTTAAGACAACATAT

AATGTCAATTGTATGTACGTTTTTCTTGTTTCTCTTAAACACTTCTTTTGCGTTTGCAT

TTGCGATTCCTAAACCGCCAATAGTAAGGAGACTATCAACGACAGTGACATCAAATT

CAACAGCGTCTTCTTGCTCAGCCAATGGAAATCCAATCGATGAGTGTTGGAGATGCG

ACGAAAACTGGAAGGACAACCGCAAAAACCTCGCGGATTGCGCGGTTGGATTCGGA

CGCGACTCAATTGGCGGTAGAGCCGGGGAGTTCTACACGGTGACTGATTCAGGAGA

CGACAATCCTCTAAATCCAACTCCAGGTACATTACGGTACGCTGCGACACAAGATCA

ACCTCTATGGATCATTTTTGATCGAGACATGGTAATACAACTAAAACAAGATCTTCA

AGTAGCTTCATACAAAACCATTGATGGTAGAGGAAATAACGTACAAATAGCTTATG

GACCGTGTTTAACTTTATATAAAGTTAGTAACATTATTATAAACAATCTTTATATTCA

FIG. 7A-1

CGATTGTGTTCCCGTGAAACGGAATGCTTTATCGTCGTTGGGAGGATACTCGGATGG

AGATGGAATATCGATATTCGAGTCTCGAGATATTTGGATTGATCATTGTACGTTAGA

GAAATGTTACGATGGGCTTATTGATGCGGTGAATGGATCCACGGATATAACGATTTC

GAATAGTTACATGTTAATCATAATGAAGTCATGCTTTTGGGCCATAGTGATGAGTA

TTCCGGTGATCGGGATATGCGAGTTACGATCGCGTTTAACTATTTTGGTGAAGGACT

TGTCCAAAGAATGCCAAGgttagtacaatcttatatttcttttcttcttttttaatgtcaaatttataagctaaccaaaatattcgtg cttaaaataccaatgtgtagGTGTAGGCATGGATATTTTCACATAGTGAATAACATTTATAGAGA

CTGGAAGATGTATGCTATTGGTGGAAGTGCTAATCCAACGATCTTTAGCCAAGGAAA

TGTTTTCATAGCTTCCAATAATCAGTTCACCAAGGAGgtacgttcgtgacatgtgctccacaaaactaag agcgttttaacctcacaattagtacaatctaattcatagtcgactaatcatttagaaatttgattttcatgtgtcttactatatggattagattctagac ggaaatgtttgctccatacttctaaactcacatgccctatacgcagGTTACAAAGCGAGAGAGTGCAGATGGAGA

CGAAGAATGGAAGGAATGGAACTGGAAATCAGAAGGAGACGAAATGGTTAACGGA

GCTTTCTTTACACCGTCAGGGAAAGAGGATTCTCCGAGCTACGCGAAATTTTCGAGT

ATGGTAGCTCGACCAGCTTCACTTCTCAAGACCACACATCCATCAGTAGGTGTTCTT

AGTTGCGAAATTGACCAAGCTTGTTAAaaacacaaacataagcttgtgaccaaatctagtgtttgtccttctttttcttt tttgctcttctacttgttgtggttattgttatcgtaaataggatttgtactgaatgtgatgatgatcatagacccaaacaacaattgttcattgtcaattt ctttaccaaaaaatttcttttacgagtcacaaagtttcgtcagttttttttatttataaatacattaaaattacttaacaacctttttccatcggataaaact aagattgacactcatcattaataattttatatatactcccattttttttagtgagtgttaacataagattaggaa

FIG. 7A-2 ctttcaattttcacctaatttaattacctccgtatttatttttttagtgcacttcaatgtctcttgcatatatatattggagcaaattataaacataATGT
TCATAGTGAAATTGTTAGTTGGTTTTAATCTCTTTTTAAGACAACATATAATGTCAAT
TGTATGTACGTTTTTCTTGTTTCTCTTAAACACTTCTTTTGCGTTTGCATTTGCGATTC
CTAAACCGCCAATAGTAAGGAGACTATCAACGACAGTGACATCAAATTCAACAGCG
TCTTCTTGCTCAGCCAATGGAAATCCAATCGATGAGTGTTGGAGATGCGACGAAAAC
TGGAAGGACAACCGCAAAAACCTCGCGGATTGCGCGGTTGGATTCGGACGCGACTC
AATTGGCGGTAGAGCCGGGGAGTTCTACACGGTGACTGATTCAGGAGACGACAATC
CTCTAAATCCAACTCCAGGTACATTACGGTACGCTGCGACACAAGATCAACCTCTAT
GGATCATTTTTGATCGAGACATGGTAATACAACTAAAACAAGATCTTCAAGTAGCTT
CATACAAAACCATTGATGGTAGAGGAAATAACGTACAAATAGCTTATGGACCGTGT
TTAACTTTATATAAAGTTAGTAACATTATTATAAACAATCTTTATATTCACGATTGTG
TTCCCGTGAAACGGAATGCTTTATCGTCGTTGGGAGGATACTCGGATGGAGATGGAA
TATCGATATTCGAGTCTCGAGATATTTGGATTGATCATTGTACGTTAGAGAAATGTT
ACGATGGGCTTATTGATGCGGTGAATGGATCCACGGATATAACGATTTCGAATAGTT
ACATGTTGAATCATAATGAAGTCATGCTTTTGGGCCATAGTGATGAGTATTCCGGTG
ATCGGGATATGCGAGTTACGATCGCGTTTAACTATTTTGGTGAAGGACTTGTCCAAA
GAATGCCAAGGTGTAGGCATGGATATTTTCACATAGTGAATAACATTTATAGAGACT
GGAAGATGTATGCTATTGGTGGAAGTGCTAATCCAACGATCTTTAGCCAAGGAAAT
GTTTTCATAGCTTCCAATAATCAGTTCACCAAGGAGGTTACAAAGCGAGAGAGTGCA
GATGGAGACGAAGAATGGAAGGAATGGAACTGGAAATCAGAAGGAGACGAAATGG
TTAACGGAGCTTTCTTTACACCGTCAGGGAAGAGGATTCTCCGAGCTACGCGAAAT
TTTCGAGTATGGTAGCTCGACCAGCTTCACTTCTCAAGACCACACATCCATCAGTAG
GTGTTCTTAGTTGCGAAATTGACCAAGCTTGTTAAaaacacaaacataagcttgtgaccaaatctagtgttt
gtccttcttttcttttttgctcttctacttgttgtggttattgttatcgtaaatagg

FIG. 7B

MFIVKLLVGFNLFLRQHIMSIVCTFFLFLLNTSFAFAFAIPKPPIVRRLSTTVTSNSTASSCS

ANGNPIDECWRCDENWKDNRKNLADCAVGFGRDSIGGRAGEFYTVTDSGDDNPLNPTP

GTLRYAATQDQPLWIIFDRDMVIQLKQDLQVASYKTIDGRGNNVQIAYGPCLTLYKVSN

IIINNLYIHDCVPVKRNALSSLGGYSDGDGISIFESRDIWIDHCTLEKCYDGLIDAVNGSTD

ITISNSYMLNHNEVMLLGHSDEYSGDRDMRVTIAFNYFGEGLVQRMPRCRHGYFHIVN

NIYRDWKMYAIGGSANPTIFSQGNVFIASNNQFTKEVTKRESADGDEEWKEWNWKSEG

DEMVNGAFFTPSGKEDSPSYAKFSSMVARPASLLKTTHPSVGVLSCEIDQACZ

FIG. 7C

ENGINEERING DISEASE RESISTANCE WITH PECTATE LYASE-LIKE GENES

This application claims the benefit of U.S. Provisional Application No. 60/159,566, filed Oct. 15, 1999.

This invention relates to a mutant gene coding for pectate lyase and homologs thereof and the use of such mutant genes in producing transgenic plants having improved disease resistance. The invention described herein was made in the course of work under grant number DE-FG02-94ER20133 and grant number DE-FG02-97ER20133 from the U.S. Department of Energy and grant number F32 GM 19499 of the National Institute of Health. The U.S. government may retain certain rights in this invention.

BACKGROUND OF THE INVENTION

1. Field of the Invention

2. Description of the Related Art

Pectate lyases, along with polygalacturonases and pectin lyases are enzymes that degrade pectin, a component of plant cell walls. Pectins are thought to act like a cement that holds adjacent cells together. Degradation of pectin plays a role in several normal developmental processes including: fruit ripening, pollen maturation, pollen tube growth and cell expansion and growth. Degradation of pectin is also a hallmark of several soft-rot diseases caused by both bacteria and fungi. Not surprisingly, pectate lyases are important virulence factors produced by several soft-rot pathogens. Therefore, the role of pathogen-produced pectate lyases in plant-pathogen interactions has been well studied. In particular, the pectate lyases (eels) of the soft-rotting Erwinia spp. have been well characterized. See Barras, F., F. Van Gijsegem, and A. K. Chatteijee[1]). Pels break the $\alpha$-1,4-glycosidic linkages in pectate by $\beta$-elimination producing unsaturated products. Pels also require $Ca^{++}$ for activity and function best at high pH, 8–9. PelA through PelE act as endo-pectate lyases with their final degradation products being short oligomers of galacturonic acid (di- to dodecamers) whose average length varies between Pels.

Plants also contain numerous genes homologous to pectate lyases. To date, two plant genes have been shown to have Pel activity when expressed in E. coli or yeast cells. One gene is primarily expressed in ripening strawberries and the other is expressed in a cultures of zinnia mesophyll cells that are differentiating into tracheary elements (See Domingo, C., et al.[2]. Also see Medina Escobar, N., et al.[3]). Pel activity was also demonstrated in cultures of zinnia cells in response to auxin or traceary element inducing media (See Domingo, C., et al.[2]).

In addition, Many pectate lyase-like genes are also highly expressed in mature pollen and are potent human allergens. Pet activity was demonstrated for a major pollen allergen of Japanese cedar, Cry j I (Taniguchi, Y., et al, Cryj I[4]). In contrast, researchers were unable to demonstrate Pel activity of Lat59 or Lat56, two tomato pollen-specific pectate lyase-like gene, expressed in a baculovirus expression system (Dircks, L. K., G. U. Y. Vancanneyt, and S. McCormick[5]). Therefore, it is possible that at least some of the Pel homologs found in plants may have activities other that degrading polygalacturonic acid and may utilize different pectic substrates.

SUMMARY OF THE INVENTION

The present invention discloses methods of creating disease resistant plant lines by using antisense, co-suppression or any other method to genetically engineer the loss, or partial loss, of activity of pectate lyase homologs into any plant. The inventors have surprisingly discovered that a plant-produced pectate lyase homolog is necessary for the compatible interaction between Arabidopsis and the obligate pathogens *Erysiphe cichoracearum* and *E. orontii*. The present invention identifies four putative loss of function mutations in a gene, PMR6, with homology to pectate lyases and demonstrated that the mutants are highly resistant to *E. cichoracearum* and *E. orontii*. In addition, we envision that another mutant, pmr5, is resistant to powdery mildew due to a mutation in another pectate lyase homolog that contained on BAC AB009050 (SEQ ID Nos: 7 and 8). Several host defenses are also constitutively activated in these mutants, suggesting a possible mechanism for the resistance. In addition, the mutant plants are more compact and have altered leaf morphology.

A primary object of the present invention is to use any plant gene with homology to pectate lyase to increase pathogen resistance and alter plant morphology in any plant species. If the pmr5 phenotype is due to a mutation in the pectate lyase homolog on BAC MDF20, then we contemplate that loss of pectate lyase activity in general, not necessarily limited to genes with high homology to PMR6, can result in disease resistance. The notion that more distantly related pectate lyases may confer disease resistance is further supported by the fact that MDF20 and PMR6 are not extremely closely related to one another (FIG. 8). In fact, they are about as closely related to nine other Arabidopsis homologs as they are to each other.

Specifically, the present invention can employ any technology (i.e. mutagenesis, antisense, co-suppression) necessary to decrease the activity of the Pel homologs in plants. It is expected that the nucleotide sequence used for any given species will be an endogenous Ped homolog, however, using exogenous Pel homologs may also be effective in generating resistance. An important component of this system is the promoter used to express the antisense/cosuppression construct. The present invention can employ any of the promoters discussed herein or any other promoter sequence that controls expression of the construct in tissues that are normally infected by a pathogen as part of our antisense/cosuppression constructs.

Constitutive promoters such as: CaMV 35s and nptII, should decrease Pel activity throughout the plant and result in a phenotype similar to pmr5 and pmr6. However, for some applications, the dwarf phenotype and altered leaf morphology may not be desirable. It may be possible to separate disease resistance from the pleiotropic phenotypes by using epidermal specific (i.e. chalcone synthase promoter) or pathogen inducible promoters (i.e. PR1 promoter). In theory, these constructs should only inactivate Pel activity where/when it is necessary to achieve disease resistance rather than the global inactivation presumably necessary for the pleiotropic phenotypes. It may also be useful to employ other promoters with different expression patterns.

The present invention also contemplates that resistant plants can be made by expressing proteins that inhibit the enzymatic activity of the PMR proteins.

The present invention further contemplates that the identification of the PMR genes as disease resistance genes also opens new possibilities for rational design of chemicals that inhibit the growth of pathogens. The present invention discloses that a chemical that inhibits the action of either of the PMR proteins or related proteins will cause fungal disease resistance. Thus, it is contemplated that using known techniques the PMR genes can be used to design rational screens for such chemical compounds. As is known in the art this could be accomplished by expressing the genes in a host such as a bacterium or yeast, so that adequate amounts of largely pure protein could be produced. The protein could then be assayed for enzymatic activity in high throughput screens in the presence and absence of possible inhibitory compounds.

The present invention also contemplates that the PMR genes could be used to produce protein for structural studies by techniques such as Xray crystallography. Once the three dimensional structure is determined it will be possible to design inhibitors of the enzyme by those skilled in the art of rational drug design.

The same techniques applied to create resistant plants can also be applied to alter plant morphology. The small size, compact growth, increased branching and cupped leaves seen in pmr5 and pmr6 may be useful traits for some agricultural and horticultural applications. For example, many, horticultural crops have been selected for compact growth habit and increased branching. In addition, many dwarf varieties of vegetable crops and fruit crops are in use today. By transgenically decreasing Pel activity it may be possible to create a well branched, compact dwarf and resistant line simultaneously.

BRIEF DESCRIPTION OF THE DRAWINGS

FIGS. 1A-1–1B-3 shows the phenotype of pmr5 and pmr6. (A) Plants were inoculated with *E. cichoracearum* eight days prior to being photographed. Representative leaves were detached and photographed. Note the extensive fungal growth on Columbia. (B) Mature rosettes just prior to bolting, approximately 28 days old.

FIGS. 3A-1–3B-3 shows a cytological description of pmr5 and pmr6. (A) Uninfected leaves were stained with trypan blue to highlight dead cells. Note that dead cells are clustered along veins. (B) Accumulation of autoflourescent compounds in uninfected pmr5 and pmr6 leaves follows the same pattern as dead cells.

FIGS. 5A-1–C show sequences relating to PMR6. FIG. 5A shows the genomic sequence including upstream and downstream regions (SEQ ID NO: 1). FIG. 5B shows a partial cDNA sequence (SEQ ID NO: 2). FIG. 5C shows predicted amino acid sequence for pmr6 (SEQ ID NO: 3).

FIGS. 7A-1–C show sequences relating to a protion of BAC MDF20 with homology to pectate lyase. FIG. 7A shows the genomic sequence including upstream and downstream regions (SEQ ID NO: 4). FIG. 7B shows the predicted cDNA sequence (SEQ ID NO: 5). FIG. 7C shows the predicted amino acid (SEQ ID NO: 5).

DETAILED DESCRIPTION OF THE INVENTION

Figure 2A:
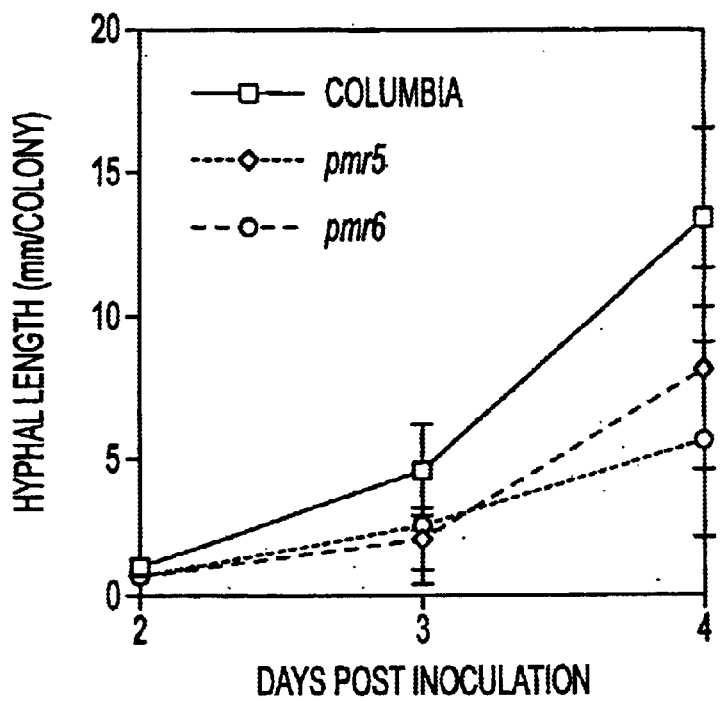
FIGS. 2A and 2B shows the quantification of *E. chichoracearum* growth on pmr5 and pmr6. (A) Hyphal length per colony at various times after inoculation. Note that all mutants support some hyphal growth. (B) Mean conidiophores per colony at six days post inoculation. Error bars are +/−SD based on at least 15 colonies.
Figure 2B:
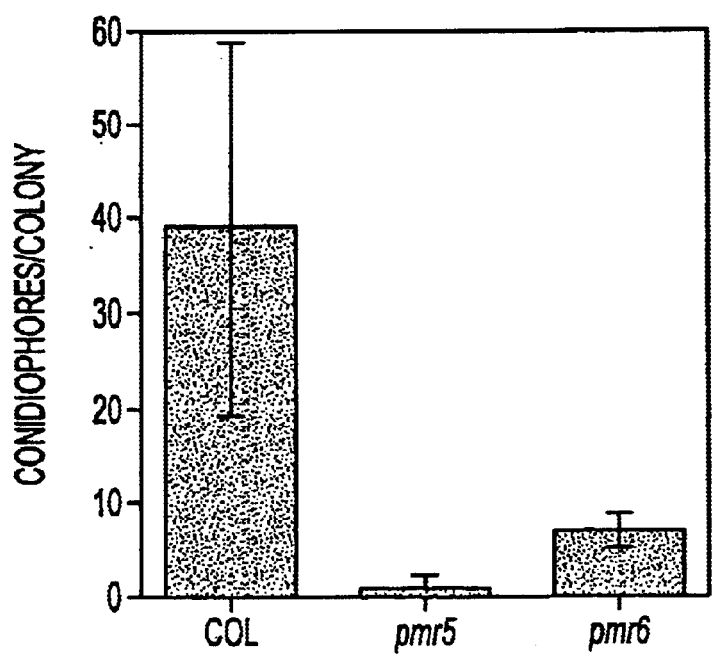

The role of pectate lyases in plant-pathogen interactions has focused on the degradation of plant tissues by pathogen secreted Pels. These Pels macerate plant tissue and facilitate further pathogen growth. At the same time, Pel activity produces poly galacturonic acid oligomers that serve as potent elicitors of plant defenses (reviewed in (Vancutsem, P. and J. Messiaen[12]). Thus, Pel activity allows plants to sense and respond to pathogen attack. In contrast, plant Pels have not previously been shown to be involved in plant-pathogen interactions.

The present invention discloses the surprising discovery that a plant gene with homology to pectate lyase is required for powdery mildew susceptibility. This seems counterintuitive because Pel activity should produce polygalacturonic acid oligomers that could then elicit host defenses. The inventors, therefore, ask why do mutations in a putative Pel gene result in resistant plants? The inventors have formed the following non-limiting theories in response to that question. One possibility is that PMR6 is involved in recycling pectin and when its activity is lost polygalacturonic acid oligomers, that would normally be degraded by PMR6, accumulate and stimulate host defenses. This interpretation is consistent with the constitutive accumulation of autoflourescent compounds and callose, the spontaneous formation microlesions and the basal levels of PR1 expression sometimes seen in the mutants. In this scenario, pmr6 plants are primed to respond to pathogen attack.

Another possibility involves the active suppression of host defenses by di- and trimers of galacturonic acid. This phenomenon, has recently been observed in wheat leaves infiltrated with digested pectin products (Moerschbacher, B. M., et al.[13]). In this scenario, in a compatible interaction *E. cichoracearum* would rely on PMR6 activity to produce di- and trimers of galacturonic that, in turn, would suppress host defenses. Ironically, host defenses are elicited by longer oligomers of galacturonic acid. However, this scenario does not fit the constitutive expression of host defenses observed in the mutants. This entire scenario is very speculative and based on a single report of inhibition of resistance by di- and trimers. Therefore, we favor the pectin-recycling scenario at this time.

The vegetative phenotype of pmr5 and pmr6, compact growth habit, and cupped leaves, may result directly from the loss of Pel activity or may be indirect results of stress or possibly hormonal activity of polygalacturonic acid oligomers. We favor a fairly direct explanation: Cupped leaves could be the result of a failure of Pel activity to sufficiently loosen cell-cell attachments to allow normal cell expansion and growth Similarly, short petioles could be the result of petiole cells that fail to fully expand. Without regard to the non-limiting theories proposed, the inventors have discovered and herein discloses the surprising discovery that a plant gene with homology to pectate lyase is required for powdery mildew susceptibility. Further, the inventors have discovered the necessary nucleotide sequences and methods to employ to use any plant gene with homology to pectate lyase to increase pathogen resistance and alter plant morphology in any plant species. Other discoveries of the present invention are detailed below and in the claims of the present application The present invention discloses that a plant gene having homology to pectate lyase can effectively increase pathogen resistance.

Related nucleotide or amino acid sequences are found when there is similarity or identity of sequence and this may be determined by comparison of sequence information, nucleotide or amino acid, or through hybridization between a gene endcoding pectate lysase probe and a candidate source (e.g., Southern or Northern blots, genomic or cDNA libraries). Conservative changes, such as Glu/Asp, Val/Ile, Ser/Thr, Arg/Lys and Gln/Asn may also be considered in determining sequence similarity.

Typically, a nucleotide sequence may show as little as 80% sequence identity, and more preferably at least 90% sequence identity, between the target sequence and the pectate lysase polynucleotide excluding any deletions or additions which may be present, and still be considered related. Nucleotide sequence identity may be at least 95% and, most preferably, nucleotide sequence identity is at least 98%. Amino acid sequences are considered to be related with as little as 90% sequence identity between the two polypeptides; however, 95% or greater sequence identity is preferred and 98% or greater sequence identity is most preferred.

Pectate lysase. Thus, the use of complex mathematical algorithms is not required because amino acid sequences can be aligned without introducing many gaps. But such algorithms are known in the art, and implemented using default parameters in commercial software packages provided by DNASTAR, Genetics Computer Group, Hitachi Genetics Systems, and Oxford Molecular Group (formerly Intelligenetics). See Doolittle, *Of URFS and ORFS*, University Science Books, 1986; Gribskov and Devereux, *Sequence Analysis Primer*, Stockton Press, 1991; and references cited therein. Percentage identity between a pair of sequences may be calculated by the algorithm implemented in the BESTFIT computer program (Smith and Waterman, J. Mol. Biol., 147, 195–197, 1981; Pearson, Genomics, 11, 635–650, 1991). Another algorithm that calculates sequence divergence has been adapted for rapid database searching and implemented in the BLAST computer program (Altschul et al., Nucl. Acids Res., 25, 3389–3402, 1997).

Conservative amino acid substitutions, such as Glu/Asp, Val/Ile, Ser/Thr, Arg/Lys and Gln/Asn, may also be considered when making comparisons because the chemical similarity of these pairs of amino acid residues would be expected to result in functional equivalency. Amino acid substitutions that are expected to conserve the biological function of the native pectate lysase polypeptide would conserve chemical attributes of the substituted amino acid residues such as hydrophobicity, hydrophilicity, side-chain charge, or size. Functional equivalency or conservation of biological function may be evaluated by methods for structural determination and bioassay as disclosed herein. Thus, amino acid sequences are considered to be related with as little as 90% sequence similarity between the two polypeptides; however, 95% or greater sequence similarity is preferred and 98% or greater sequence similarity is most preferred.

The present invention is more fully defined by reference to the following examples, which are provided only for demonstration of the inventive concept of the present invention and are not intended to further limit the scope of the invention further than that of the claims provided herewith.

EXAMPLES

Materials and Methods

Plant lines and growth conditions: *Arabidopsis thaliana* ecotype Columbia (Col) and Wassilewskija (WS) were used in this study as indicated. Adult plants were grown in ProMix HP (Premier Horticulture Inc., Red Hill, Pa.) and fertilized once with one tsp/gal of Peter's Professional fertilizer (20-20-20) at the first watering after germination. Plants to be infected with powdery mildew were grown in a growth chamber at 22° C. with 14 hours of illumination per day or in greenhouses with supplemental lighting to increase daylength to 14 hr when necessary. Seeds were mutagenized with methane-sulfonic acid ethyl ester (EMS) as described or by transformation with Agrobacterium as described (Bechtold, N., J. Ellis, and G. Pelletier[6]).

Squash, variety Kuta (Park Seed Co.) and *Capsella bursera-pastoris* (gift from F. Ausabel and L. Reuber) were used as a host for the production of *Erysiphe cichoracearum* and *E. orontii* inoculum, respectively. These alternate hosts were used rather than Arabidopsis because they have larger leaves than Arabidopsis. Another advantage to using Capsella rather than Arabidopsis is that Capsella plants are very slow to bolt allowing us to maintain cultures for months on the same plant.

Growth and maintenance of powdery mildews: Inoculum of *Erysiphe cichoracearum* was prepared by touch-inoculating three-week-old squash plants with infected squash leaves. The inoculum was ready for use after 10–12 days of growth. Arabidopsis plants were inoculated by placing approximately four foot high cardboard settling towers over 1 or 2 flats and gently tapping 1–4 squash leaves over the top of the settling towers. For measuring fungal growth it was important to have colonies originating from widely spaced single conidia. Therefore, the squash leaves were tapped over a 3-41/33 Nitex nylon monofilament screen (Sefar America Inc., Kansas City, Mo.) and the resulting powder was brushed back and forth to allow single conidia to fall through. After allowing spores to settle for about 15 minutes, the plants were placed in a dew chamber for 45–60 minutes as described (Adam, L. and S. C. Somerville[7]). Upon removal from the dew chamber the plants were placed in a growth chamber matching the chamber they were grown in prior to inoculation. If the plants were grown in the greenhouse prior to inoculation they were placed in a phytocell, a completely enclosed greenhouse with precise temperature control, after inoculation. The phytocell typically maintained 85–100% relative humidity.

*E. orontii* was maintained on Capsella by simply placing uninfected plants in a growth chamber with infected plants and allowing them to be inoculated by air movement in the growth chamber. Capsella plants grown in this fashion could supply inoculum for several months as new leaves continually grow and become infected. Arabidopsis plants were inoculated by placing a 65 cm tall inoculation tower over a 13.5 cm pot and tapping 4–6 heavily infected Capsella leaves over the top of the tower. After allowing five minutes for the spores to settle the pot was placed directly into the growth chamber.

Isolation of mutants: Mutagenized seeds were sown on flats and placed at 4° for 2–4 days then moved to a greenhouse. Approximately two weeks after germination plants were thinned to approximately one plant per six cm$^2$. When the plants had at least four true leaves, after 17–21 days of growth, the plants were inoculated with powdery mildew. One week later the plants were screened and plants with reduced powdery mildew growth were retained.

Genetic mapping: Mutants were crossed with WS ecotype plants to create $F_2$ mapping populations. $F_2$ seeds was planted as described for screening and DNA was extracted from resistant plants, homozygous mutant, as described (Edwards, K, C. Johnstone, and C. Thompson[8]) PCR-based markers, SSLP and CAPS, polymorphic between Col and WS were used to map the mutations based on co-segregation of markers with the mutation.

Northern blot analysis: To evaluate the correlation between defense gene expression and powdery mildew resistance, the levels of PR1 mRNA after infection was determined. Plants were heavily inoculated with *E. cichoracearum* and 15 plants were harvested for each point at 0,1,3 and 5 days after inoculation. Plants were frozen in liquid nitrogen and ground using mortar and pestle. Total RNA was prepared using TRIZOL reagent following manufacturers instructions (Gibco). Ten ug of RNA was separated using glyoxal gel electrophoresis and blotted to nylon membrane. Blots were also hybridized to a rDNA probe to control for loading. Signals were visualized and quantified using a PhosphorImager (Molecular Dynamics, Sunnyvale, Calif.)

Microscopy: To visualize fungal hyphae, infected leaves were cleared in 95% ethanol until completely white and then stained with 250 ug/ml trypan blue in a 1:1:1 solution of lactic acid: glycerol: water for 15 minutes, rinsed in lactic acid: glycerol: water solution and mounted with 50% glycerol. Individual colonies were photographed at 50–100× magnification using a digital camera (Pixara) attached to a Leica microscope. Total hyphal length was measured using NIH image software.

To visualize microscopic lesions, leaves were stained using a modification of a previously described procedure (Bowling, S. A., et al.[9]). Leaves were placed in a 1:1:1:1 solution of phenol, lactic acid, glycerol, water plus 250 ug/ml trypan blue. Samples were then placed in a bell jar and a vacuum was applied and slowly released twice. Next the tubes containing the leaves and stain were placed in a boiling water bath for two minutes and then allowed to cool for at least one hour. The leaves were destained in the 1:1:1:1 solution used for staining, without trypan blue, for at least two hours. The samples were mounted in 50% glycerol and examined under bright field illumination.

To visualize callose, leaves were cleared in 95% ethanol and then placed in 0.02% analine blue in 150 mM potassium phosphate dibasic, pH>9, and allowed to stain for at least on hour. Leaves were then mounted in 50% glycerol and examined for fluorescence as described (Adam, L. and S. C. Somerville[7]).

Autoflourescent compounds were detected by clearing leaves in 95% ethanol, equilibrating them in a 1:1:1 solution of lactic acid: glycerol: water and mounting in 50% glycerol. The leaves were examined under epifluorescent illumination as described (Adam, L. and S. C. Somerville[7]).

Cloning: Four alleles of pmr6 were identified in our screen, two were derived from T-DNA mutagenized populations and two were derived from EMS mutagenized populations. Plant DNA flanking the site of insertion for pmr6-3 was recovered using the genome walker kit following manufactures instructions (Clontech). The following oligonucleotides, specific for the T-DNA used in the mutagenesis, were used to amplify plant DNA flanking the left border region: LB1-AACTTGATTTGGGTGATGGTTCACGTAGTG (SEQ ID NO; 9) and LB2-GCCCTGATAGACGGTTTTTCGCCCTTTGAC (SEQ ID NO: 10); and the right border region RB1-CAATCCATCTTGTTCAATCATGCGAAACGA (SEQ ID NO: 11) and RB2-CGACTTTTGAACGCGAATAATGGTTTCTG (SEQ ID NO: 12). The PCR products obtained for both the left and right border were sequenced using BigDye cycle sequencing kit (ABI Prism) and an ABI310 sequencer. The site of the T-DNA insertion in pmr6-4 was determined by sequencing a DNA fragment amplified by PCR using one primer in the T-DNA, JV4-AGGTCTRGCGAAGGATAGTGGGATTGT (SEQ ID NO: 13), and another primer in the putative gene, 3417-ATGTATGCTATTGGTGGTAGTG (SEQ ID NO: 14). The mutations in the two EMS alleles was determined by sequencing a DNA fragment amplified with primers flanking the gene, 2026-GAGAGGCCCAATATAAAATACGAG (SEQ ID NO: 15) and 6097-ATAATCCGGACTGGAAAAACAAAC (SEQ ID NO: 16).

pmr5 was mapped 1.7 cM above the CAPS marker LFY3. In that same region lies the BAC MDF20 (SEQ ID NOs: 7 and 8), genbank number AB009050 and on that BAC lies a putative gene homologous to PMR6. Given the very similar phenotypes of pmr5 and pmr6, we propose that the pmr5 phenotype is due to a mutation in this pectate lyase-like gene. To test this hypothesis, the gene MDF20 will be amplified using the primers, MD3'-ATCCCGGGAATACAAGAACTTGACAGCTCC (SEQ ID NO: 17) and MD5'-TACCCGGGGAAGCAGAGATCCTC (SEQ ID NO: 18), and the resulting DNA will be transformed into pmr5 to see if it can complement the pmr5 mutation.

Figure 8:
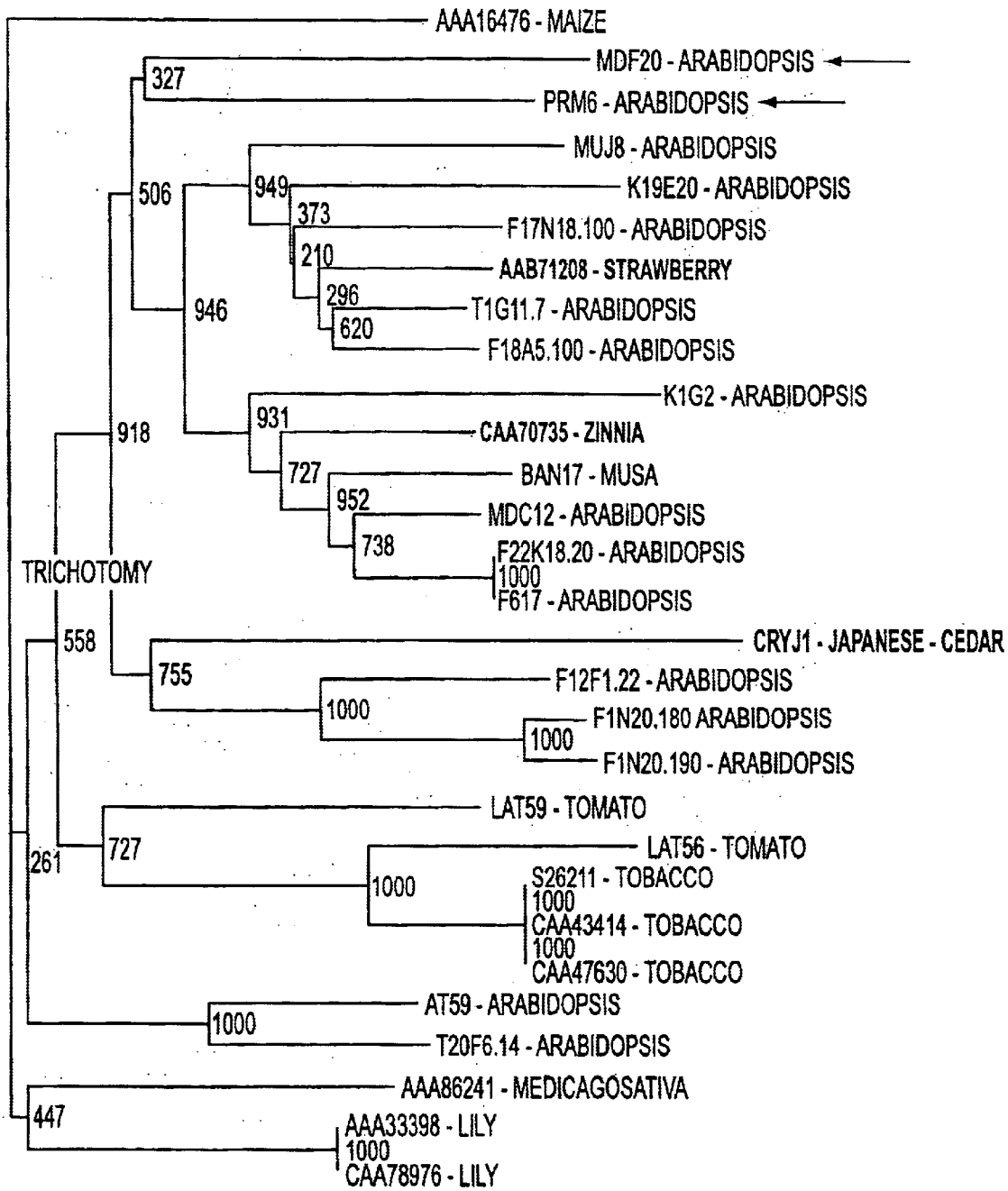
FIG. 8 shows a phylogram, with bootstrap values, of plant genes with homology to pectate lyase. Pectate lyase activity has been demonstrated for the genes in bold. PMR6 and MDF20 are marked by arrows.

Phylogeny of pectate lyase genes: The protein or predicted protein sequences from several plant pectate lyase genes were aligned and a phylogenic tree constructed using clustalX software. The output from clustalX was displayed using TreeViewPPC software (FIG. 8).

Results

Figures 1, 3A:
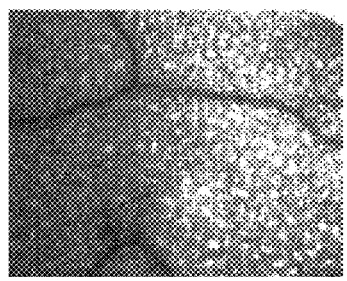

Isolation of mutants and genetics: Five mutants were found that are examples of the invention taught by this patent Crosses between mutants show that two complementation groups that are strongly resistant to powdery mildew are defined by this collection (FIG. 1). The first mutant has been designated powdery mildew resistant 5, pmr5, The remaining four mutants are allelic and have been designated pmr6-1 through pmr6-4. All mutants were backcrossed to Col plants two times prior to all characterizations, excluding mapping. Segregation of powdery mildew resistance in the F1 and F2 generations indicated that all mutants are recessive, nuclear genes that segregate in a simple 3.1 Mendelian fashion ( See Table 1). In addition to powdery mildew resistance, both pmr5 and pmr6 are smaller than wild-type, more compact (shorter petioles) and have leaves cupped up rather than down as in wild-type (FIG. 1). In addition, pmr5 seems to be somewhat more branched than wild-type.

TABLE 1

Genetic analysis of powdery mildew resistant mutants.

| | | | Disease response | | |
|---|---|---|---|---|---|
| Cross (female × male) | Type | Total | Suscep-tible | Resis-tant | $X^2$ |
| PMR5/PMR5 × pmr5/pmr5 | F1 | 13 | 13 | 0 | |
| PMR5/PMR5 × pmr5/pmr5 | F2 | 98 | 74 | 22 | 0.22<sup>a</sup>; $P > 0.05$ |
| PMR6/PMR6 × pmr6/pmr6 | F1 | 20 | 20 | 0 | |

TABLE 1-continued

Genetic analysis of powdery mildew resistant mutants.

| Cross (female × male) | Type | Total | Suscep-tible | Resis-tant | $X^2$ |
|---|---|---|---|---|---|
| PMR6/PMR6 × pmr6/pmr6 | F2 | 486 | 257 | 129 | 0.62[a]; $P > 0.05$ |

A Chi-squared calculated for an expected 3:1, wild-type:mutant ratio

The position of each locus on the Arabidopsis genetic map was determined using PCR-based CAPS and SSLP markers. pmr5 mapped to chromosome 5,1.7 cM above LFY3 based on 116 chromosomes. pmr6 was mapped to chromosome 3, 9.4 cM below R30025 and 4.2 cM above nga707 based on 96 chromosomes.

Figures 2, 3A:
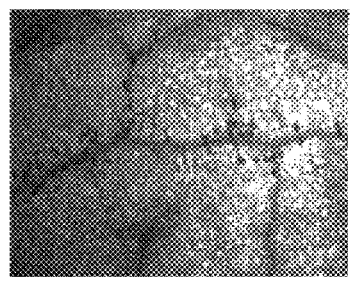

Timecourse of fungal growth: In order to determine if the resistance observed in the mutants was correlated with a block at a defined stage of fungal development, the growth of hyphae and level of conidiation was measured over time using trypan blue staining. The same trend was apparent for both pmr5 and pmr6 mutants. After landing on a leaf, fungal spores germinate and begin growth in a normal fashion. However, colonies on mutant plants grew slower than colonies on wild-type plants. Two days after inoculation hyphal length/colony is significantly less than wild-type (FIG. 2). Eventually, many colonies appear to be dead or dying (shriveled and broken hypha) on the mutants, while colonies on wild-type plants have hundreds of conidiophores (FIG. 2). However, on both pmr5 and pmr6plants a small subset of colonies do produce some conidiophores indicating that neither of the mutations results in a complete block of any stage of fungal development.

Resistance to another powdery mildew: To determine if the powdery mildew resistance observed in pmr5 and pmr6 was broad spectrum or restricted to E. cichoracearum the mutants were challenged with another species of powdery mildew, E orontii. Plants were inoculated with E. orontii and symptoms were scored on a disease response, DR, scale from 0=fully resistant to 4=fully susceptible 7–10 days after inoculation The average DR scores based on nine replicates were: Col 3.6, pmr5 0 and pmr6 0.1, indicating that the mutants are strongly resistant to E. orontii.

Cytological characterization: To see if the accumulation of callose, autoflourescent compounds or the presence of microscopic lesions was correlated with resistance or were constitutively expressed in pmr5 or pmr6, infected leaves were examined to look for these common defense responses. At least eight leaves from several infected plants were examined with each stain at zero, one and five days post inoculation, d.p.i. Many fungal colonies were examined on each leaf. The entire experiment was repeated at least twice for each stain.

Figures 3, 3A:
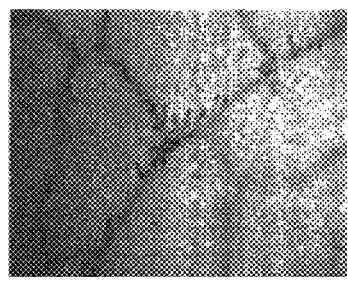
Figures 1, 3B:
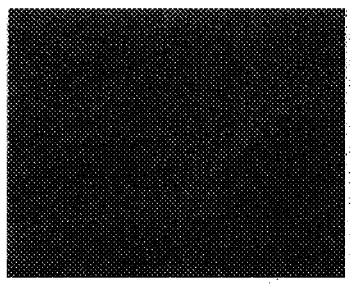
Figures 2, 3B:
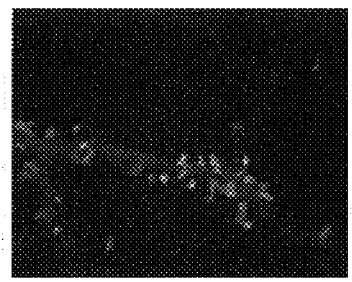
Figures 3, 3B:
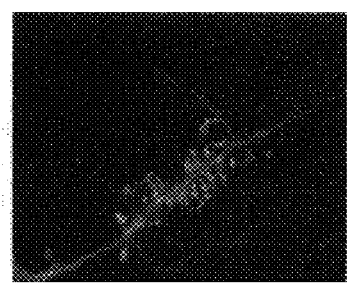

Trypan blue staining was used to visualized dead and dying cells, a hallmark of the hypersensitive response, a common defense employed by plants. Interestingly, both pmr5 and pmr6 had occasional clusters of what appear to be individual dead, crushed mesophyll cells closely associated with veins toward leaf tips (FIG. 3). Col plants did not display any microlesions prior to infection. However, there was no apparent increase in lesions on pmr5 or pmr6 leaves in response to powdery mildew infection at one or 5 d.p.i. when compared to Col. Indeed, no lesions were found to be associated with fungal colonies on pmr5, pmr6 or Col at one d.p.i. After five days, occasional dead epidermal cells beneath a small percentage of colonies were seen on all plants examined. The fact that the majority of colonies on the mutants were not associated with dead epidermal cells, but were stunted, indicates that cell death is not the primary mechanism of resistance in the mutants.

Another defense strategy plants employ to limit pathogen growth is the production of antimicrobial autoflourescent compounds. To determine if levels of autoflourescent compounds were increased in the mutants cleared, unstained leaves were examined under epifluorescent illumination as described (Adam, L. and S. C. Somerville[7]). Both pmr5 and pmr6 constitutively accumulate large amount of autofloures-cent compounds, again focused along veins toward the leaf tips (FIG. 3). As with the microlesions, the level of autoflourescent compounds did not noticeably increase after infection with powdery mildew. No autoflourescent compounds were seen in Col leaves before or after infection with powdery mildew.

In response to penetration attempts by powdery mildews, plants reinforce the cell wall directly beneath the penetration peg by depositing new cell wall material creating a cell wall apposition called a papilla Papilla formation is thought to be an attempt by the plant to prevent invasion by the fungus. Enhanced papilla formation is correlated with the resistance of some barley cultivars and is proposed to be a mechanism for the resistance (Jorgensen, J. H.[10]). To address the possibility that the mutants may have enhanced papilla formation, we stained infected leaves for callose, a component of the papilla, using analine blue. Col, pmr5 and pmr6 plants all produced similar papilla in response to fungal penetration attempts (data not shown). However, a small amount of callose not associated with the fungus was apparent in both mutants. Examination of uninfected leaves revealed that this callose accumulation is constitutive. Similar to the microlesions, callose deposits are concentrated along veins toward the leaf tips. However, the bright background of autoflourescent compounds made the determination of the full extent of the callose deposits impossible.

Figure 4:
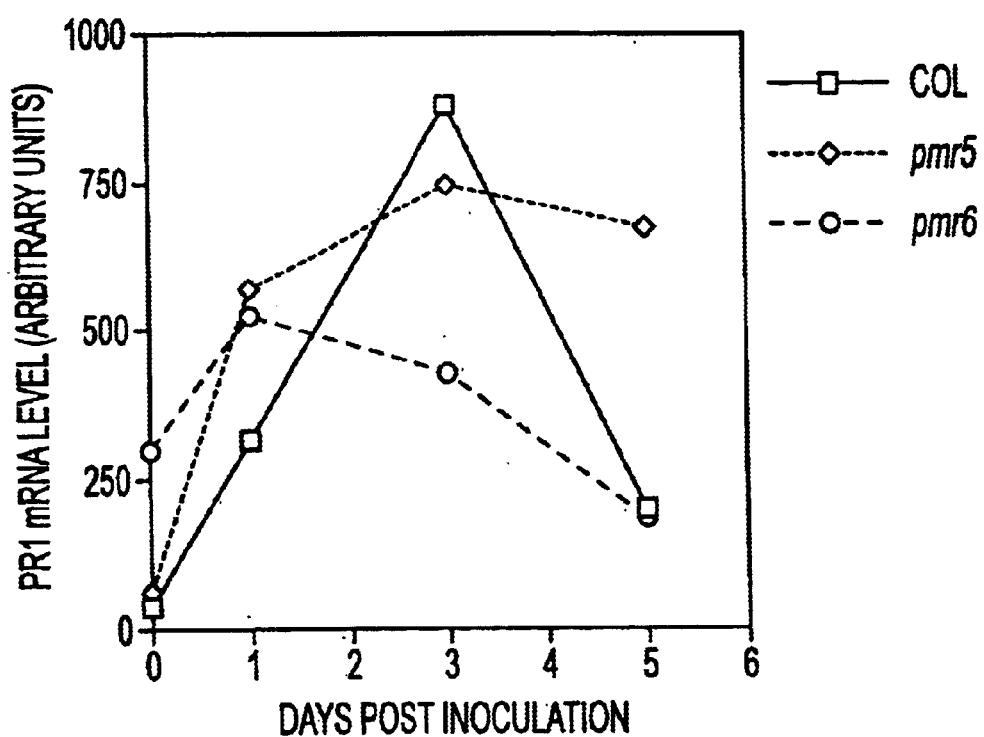
FIG. 4 shows a timecourse of PR1 mRNA expression. Plants were heavily inoculated with *E. cichoracearum* and samples were harvested at 0, 1, 3 and 5 days post inoculation. Total RNA was prepared and the levels of PR1 mRNA determined by northern blotting, normalized to rRNA levels and plotted. Note the elevated PR1 level of pmr6 on day 0.

Kinetics of PR1: In order to determine if the resistance observed in the mutants was correlated with increases in the expression of a known defense gene northern blots were used to determine the steady state levels of MnRNA for the PR1 gene at various times after inoculation. PR1 was chosen as a marker for the SA-dependent SAR pathway (Ryals, J. A., et al.[11]). Both pmr5 and pmr6 constitutively express variable levels of PR1 mRNA ranging from almost no expression, similar to wild-type, to levels higher than pathogen infected Col plants. One day after infection pmr5 and pmr6 typically have higher levels of PR1 than Col plants (FIG. 4). However, by three days after infection the levels of PR1 in both mutants are typically not as high as wild-type levels.

Cloning: Plant DNA flanking the T-DNA insert in pmr6-3 was isolated using the genome walker kit. A database search using the flanking DNA indicated that the region was contained on a sequenced BAC, F28P10. After the BAC was annotated the gene corresponding to PMR6 was designated F28P10.100, from nucleotide 38336 to 41968. NetGene software indicated that the insertion site lies within a predicted gene. A putative cDNA and the corresponding predicted protein sequence were pieced together from the genomic sequence (FIG. 5). The genomic sequence including upstream and down stream regions is shown in FIG. 5A. A partial cDNA sequence is shown in FIG. 5B. The predicted amino acid sequence for PMR6 is shown in FIG. 5C.

Further BLAST searches using the predicted cDNA and protein sequences indicated that the gene had homology to the pectate lyase gene family. Also, one EST matched our tagged sequence and was obtained from the ABRC stock center. However, this clone was not full length, so a RT-PCR product was sequenced to verify the predicted message sequence.

Figure 6:
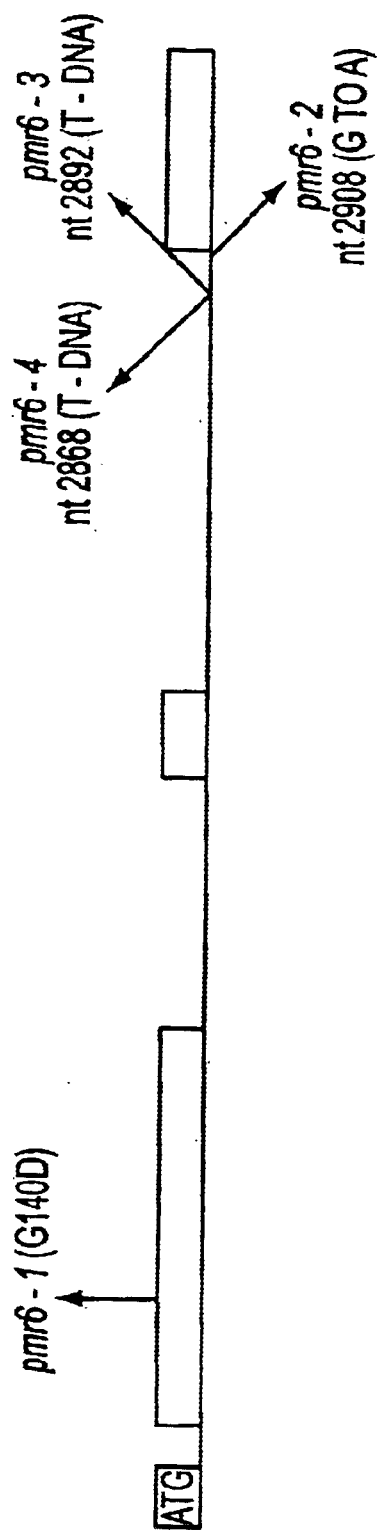
FIG. 6 shows sequence alterations in the pmr6 alleles of the PMR6 gene. pmr6-1 has aspartic acid at 140 instead of glycine. The G to A transition in pmr6-2 alters the splice junction resulting in a 1 bp deletion in the mature message. This frameshift alters the carboxy terminal 85 amino acids of PMR6.

To verify that the gene disruption in pmr6-3 was responsible for the powdery mildew resistant phenotype, the lesions in three independent pmr6 alleles identified by sequence analysis (FIG. 6). pmr6-4 contained a T-DNA insertion at nt 2868. pmr6-1 had a G to A transition that results in a substitution of aspartic acid for glycine at amino acid 140. pmr6-2 had a G to A transition at nt 2908 which results in miss-splicing of the mature message. The miss-splicing was verified by sequencing a RT-PCR product from pmr6-2. The miss-splicing results in a single base deletion causing a frameshift that alters the last 85 amino acids of the protein.

Arabidopsis contains at least 16 putative pectate lyase family members, one of which, on BAC MDF20, maps very close to pmr5. The sequence of a portion of BAC MDF20 with homology to pectate lyase is shown in FIG. 7. FIG. 7A shows the genomic sequence including upstream and down stream regions. Coding regions are shown in CAPS. FIG. 7B shows the predicted cDNA sequence with the predicted open reading frame shown in CAPS. FIG. 7C shows the predicted amino acid sequence. Given the extremely similar phenotypes of pmr5 and pmr6 it seems likely that the pmr5 phenotype could also be due to a mutation in a pectate lyase gene. To address this hypothesis we are currently sequencing the putative gene from pmr5 plants to look for mutations and are also transforming the wild-type gene into pmr5 to see if it can complement the mutation.

Phylogeny of pectate lyase genes: A comparison of several plant pectate lyase and putative pectate lyase genes was conducted to see where PMR6 and the gene on MDF20 fit into the gene family. The predicted protein sequences were aligned using clustalX software and the output was visualized graphically by constructing a phylogram using Tree-ViewPPC software (FIG. 8). It appears that MDF20 and PMR6 are not very closely related, in fact, they are about as closely related to nine other Arabidopsis homologs as they are to each other. This suggests that decreasing the activity of any pectate lyase may be result in disease resistant plants.

References

1. Barras, F., F. Van Gijsegem, and A. K. Chatterjee, *Extracellular enzymes and pathogenesis of soft-rot Erwinia*. Annual Review of Phytopathology, 1994. 32: p. 201–234.

2. Domingo, C., et al., *A pectate lyase from Zinnia elegans is auxin inducible*. Plant Journal, 1998. 13: p. 17–28.

3. Medina Escobar, N., et al., *Cloning, molecular characterization and expression pattern of a strawberry ripening-specific cDNA with sequence homology to pectate lyase from higher plants*. Plant Molecular Biology, 1997. 34: p. 867–877.

4. Taniguchi, Y., et al., *Cryj I, a major allergen of Japanese cedar pollen, has pectate lyase enzyme activity*. Allergy, 1995. 50: p. 90–93.

5. Dircks, L. K., G. U. Y. Vancanneyt, and S. McCormick, *Biochemical characterization and baculovirus expression of the pectate lyase-like LAT56 and LAT59 pollen proteins of tomato*. Plant Physiology and Biochemistry, 1996. 34: p. 509–520.

6. Bechtold, N., J. Ellis, and G. Pelletier, *In planta Agrobacterium mediated gene transfer by infiltration of adult Arabidopsis thaliana plants*. Comptes Rendus de l'Academie des Sciences Serie III Sciences de a Vie, 1993. 316: p. 1194–1199.

7. Adam, L. and S. C. Somerville, *Genetic-Characterization of 5 Powdery Mildew Disease Resistance Loci in Arabidopsis-Thaliana*. Plant Journal, 1996. 9(#3): p. 341–356.

8. Edwards, K., C. Johnstone, and C. Thompson, *A Simple [and] Rapid Method For the Preparation of Plant Genomic Dna For Pcr Analysis*. Nucleic Acids Research, 1991. 19.

9. Bowling, S. A., et al., *The cpr5 mutant of arabidopsis expresses both MPR1-dependent and NPR1-independent resistance*. Plant Cell, 1997.9: p. 1573–1584.

10. Jorgensen, J. H., *Genetics of Powdery Mildew Resistance in Barley*. Critical Reviews in Plant Sciences, 1994. 13(#1): p. 97–119.

11. Ryals, J. A., et al., *Systemic Acquired-Resistance*. Plant Cell, 1996. 8(#10): p. 1809–1819.

12. Vancutsem, P. and J. Messiaen, *Biological Effects of Pectic Fragments in Plant-Cells*. Acta Botanica Neerlandica, 1994. 43(#3): p. 231–245.

13. Moerschbacher, B. M., et al., *Small oligomers of galacturonic acid are endogenous suppressors of disease resistance reactions in wheat leaves*. Journal of Experimental Botany, 1999. 50(#334): p. 605–612.

What is claimed is:

1. An isolated nucleic acid that encodes an amino acid sequence selected from the group consisting of SEQ ID NO:3 and SEQ ID NO:6.

2. A vector comprising the nucleic acid of claim 1.

3. An expression cassette comprising the nucleic acid of claim 1.

4. The expression cassette of claim 3, wherein the nucleic acid is oriented in the sense direction.

5. The expression cassette of claim 3, wherein the nucleic acid is oriented in the antisense direction.

6. A plant cell comprising the nucleic acid of claim 1.

7. A plant cell culture, plant tissue or whole plant comprising the plant cell of claim 6.

8. The plant cell of claim 6, wherein the plant cell is from a monocotyledonous plant.

9. The plant cell of claim 6, wherein the plant cell is from a dicotyledonous plant.

10. A method of increasing resistance of a plant cell culture, a plant tissue or a whole plant to an Erysiphales, said method comprising decreasing the activity of at least one pectate lyase of the plant cell culture, plant tissue or whole plant, wherein the activity is decreased by introducing the expression cassette of claim 3 into one or more cells of the plant cell culture, plant tissue or whole plant, wherein resistance to an Erysiphales is increased in said plant cell culture, plant tissue or whole plant.

11. A method of increasing resistance of a plant cell culture, a plant tissue or a whole plant to an Erysiphales, said method comprising decreasing the activity of at least one pectate lyase of the plant cell culture, plant tissue or whole plant, wherein the activity is decreased by introducing the expression cassette of claims 4 or 5 into one or more cells of the plant cell culture, plant tissue or whole plant, wherein resistance to an Erysiphales is increased in said plant cell culture, plant tissue or whole plant.

12. An isolated nucleic acid selected from the group consisting of SEQ ID NO:1, SEQ ID NO:2, SEQ ID NO:4 and SEQ ID NO:5.

* * * * *

SEQUENCE LISTING

<160> NUMBER OF SEQ ID NOS: 18

<210> SEQ ID NO 1
<211> LENGTH: 5040
<212> TYPE: DNA
<213> ORGANISM: Arabidopsis thaliana
<220> FEATURE:
<223> OTHER INFORMATION: genomic sequence of PMR6

<400> SEQUENCE: 1
cgatttgcag gtatacaagt tactcggcaa tatgtttggc ttctccggat atgaagaata      60

-continued

| | |
|---|---|
| aataacctcc agctcacgca ggcagtgaga aactgctata acaacccaca tcttgatatt | 120 |
| ctcaggtgtg cattttgaat caattaagta aagacggaag ctttctataa ccggagctct | 180 |
| atgtaatggc agattttgt caagaaaaca ctccaacctc ttgcattcag aagaatctct | 240 |
| atgaccatac ttaagtttag gcaaccacat ccaaagatac tcccatcttt tcgacaaaat | 300 |
| gctagtggat acagcaattt tgttggaaca acaataata tcttaataag cacttcatca | 360 |
| gataactcac tgaatctatc catatcttga aacccgaaac cccaagttac tgttgttact | 420 |
| gtcgacagaa cttgggaccc taataagaaa aagataaca tctttcaggc tcataaagct | 480 |
| aaagaagcca attagtaaac aagtgaaaac tcggacacaa agaggaacag tactaaacct | 540 |
| tagaaacaag ctagattgtt aggtgaagct gagaatttt cagtgcccaa agaactgtat | 600 |
| atccttttca aatctagtag aatggtagtc tgaactagga atcaagaaag ggtaaatgta | 660 |
| aacgaagctt gaatggtaca tagcaaggaa aaggaatat gaacaagttg gtttatcaga | 720 |
| agataccaca atcgctgagc atcggaacga caaagtgttg tcctcaccgt tgatactcac | 780 |
| actggccact gacccactca tcaaagcgtt cggcgtccat ttaatttagg tgtttaatta | 840 |
| ccataaacga tgggcctggt tatgggccta acttttatgt tatacgccca tttaacttgg | 900 |
| gtgtttaatt acaaacttgc tttagcgacg actttgacga gaatgagag gcccaatata | 960 |
| aaatacgagc ttgcttacca aaatttgaga cccaaatagt aaaccaatct cctccagaat | 1020 |
| gcaagtggac acaaatcccc aagagaaaca gaatcaaaat ctcaagaaaa cctattagcc | 1080 |
| ctgtttccag caagagggca gagaagcaga gagagagaga gtgtgagaga gaaagcagct | 1140 |
| tcttcttctt ctcctcctct tctcccttat gtggatttca aatccttctc tgctactctc | 1200 |
| tcttcacatt tctctaccaa cattcttctt ctgacactca acacacacac tgcaacttcc | 1260 |
| acagctaaat ctagcaacac caagtcaaaa tccgccacta acgatgcttc ttcaaaactt | 1320 |
| ctccaacacc attttccttc tctgcctctt cttcacactc ctctccgcca ctaaaccccct | 1380 |
| aaatctcact ctccctcacc aacacccttc ccctgattcc gtcgctctcc atgtcatcag | 1440 |
| gtaaacaaaa gctcctccct ctctcattac acattttccc agataaaata aaaactcaaa | 1500 |
| cttttcttctc cgaaattcac aggagtgtaa atgaatctct tgcaagaaga caactaagct | 1560 |
| caccatcatc atcctcatca tcatcatcct cctcatcatc atcctcttgc cgtaccggaa | 1620 |
| acccaatcga cgattgctgg agatgcagcg acgcagactg gtcaacaaac cgacaaagac | 1680 |
| tagcagactg ttcaatcggc ttcggacacg gcacactcgg aggcaaaaac ggcaagatct | 1740 |
| acgtcgtaac tgactcatcc gacaacaacc caacaaaccc aacaccaggg acactccgtt | 1800 |
| acggcgtaat ccaagaagag ccactctgga tcgtcttctc ttcaaacatg ctcatcagac | 1860 |
| taaaacaaga actcatcatc aacagctaca aaaccttaga tggtcgtggc tcagccgttc | 1920 |
| acattaccgg aaacggttgc ttaactctcc aatacgttca acacatcatc atccacaacc | 1980 |
| tccatatcta tgactgtaaa ccttcagctg gattcgagaa acgtggtaga tccgatggag | 2040 |
| atgggatctc gatcttcgga tctcagaaga tctgggttga tcattgttca atgagtcatt | 2100 |
| gcaccgacgg gctaattgat gctgtgatgg gttctacagc tataactata tctaacaatt | 2160 |
| acttcaccca ccacgacgag gttatgttgt tgggtcatga tgataactat gctcctgata | 2220 |
| cggggatgca agtgacgata gcgtttaatc atttcggaca agggcttgtt cagaggatgc | 2280 |
| ctaggtgtcg gagaggttac attcatgtag tgaataatga tttcactgag tggaaaatgt | 2340 |
| atgctattgg tggtagtggt aatcccacca ttaacagtca aggaaatcgt tactctgctc | 2400 |
| cttctgatcc tagcgccaaa gaggtatttt ttcctttta tataacaaat tttacatttt | 2460 |

-continued

```
tttggattac ccatatagaa atatctttcc tttttgttgt tgttgttata tggtgtggaa    2520
cactttcttt agtagcttaa ctttgtaggg tttagtatga ttttgtggat agattttagg    2580
cttttaccat agagaacttt ttattgagta attgacaaat gtgtagtttt cattagttga    2640
ttttgattgg gttgtaaaat gttttgagta tggtcctatc ttctatgaat ccagttcata    2700
tttcacatgg acagttgtta atctttagct agtaggaaaa aatatccagt taaagttgta    2760
tgtaaatggg aaaaggaaga atcttatttt tatgagaatt gggtctacga ggagtgagac    2820
agtgatggta tgtatgtata gtattataag tgcatgacag acatgtgggc tgcttcttct    2880
acttcttctc tgtccacaca ctttattttg ttgttgttag ttgtttgaat accaccacgc    2940
gcaacgacgg cgcgtggaaa agagattgtt tgctgatcgg tggtgaaaag caggtgacga    3000
agcgagtgga ctcgaaggac gatggtgaat ggtcgaattg gaattggaga acagaagggg    3060
atttgatgga gaatgagct ttctttgtgg cctctggtga aggaatgagc tcaatgtact    3120
ctaaagcttc tagtgttgac cctaaagctg cttctctcgt agaccagctc actcgaaacg    3180
ctggcgtttt tggcggtccc aggtactatt tcttttttccc ttttttacccct tctttatttt    3240 ctaattagat ttttatttaa ccaatttaaa agtatactcc cttattagaa aaatctttta    3300
aaaactgaag catgatctct catttcggtg tttaatgtat aataaaatta gctgtgaaag    3360
cgcgtgatta gagcgcatga tttgttattg tcgttattcg ttaagtcaag aacagataac    3420
aaccgtacta ttttactatt ttagttgtgt ttagtctttt actttggagt ctagttaact    3480
tgtgattaga aaagaaaac tctaaactga cgaatttgta atttcttatt ggaaaatagg    3540
ataaataggt tctttcttgt ttgaggttct taatcacatt ctatattcat tcattcaatt    3600
attcttgaaa tggtgatata tagaagagga actatggtaa gtctgaataa ttagaatctg    3660
tataaacaat taaagtgaca cattattggt ttatttgaaa aagtagctca ttgagaatat    3720
cagacgttag ggttttggca gtattccaga attcatgtag agtcgcacgt gattgtctac    3780
ttagggaacc gaccaacttg actagtgtct gaattaaccc cacttgctat tttcattttt    3840
gcattatttt tcaagttttt agattgcatc attttttgttg tcccttttggg attatgggtg    3900 gtggaaatgt ctgtcttaat gttaattaag acatgcatga tcatgatgca aactacattt    3960
tgatacatca aatgtaattt actatacaaa agccaatagg ttttttttggt cgtaatgatg    4020 tcattatgat ggaaatgtgg aggttaagga cgattgggac ccttacctag aaagatgatt    4080
cctttttcta tggatccata ataataatta caagtccttt taaatcgcat taattgtatc    4140
cttttgactt tgtttagcta gaatgaataa tatcgtataa cttctaatga gatggttttt    4200 ggtgggggtta gggatgatca aggtcagagt ggcaattctt actctcctta tggaggcgac    4260
ggcggtggcg gtgggagcag cggtgggagc agcggtggag ggatggacgt tatgggaggt    4320
acgacgagag gaagcagcag cagcagcggc gatgacagca atgtcttcca gatgatattt    4380
ggaagcgatg caccgtctcg gccgcgttta acgttattgt tttctttgtt aatgatttcg    4440
gttttgtcgt tatcaactct attattgtga cgaatggata acaaatagga tttggaccgt    4500
tcaattgatt ggttttggt gtaaagtgtg gctctctctc cattattttc tttaattgta    4560
gttggattgg caacaataca aaacactaaa atgggattgt caaggcaacg tcaaagacga    4620
actttgtctc atccaatcaa atgctttgtt tcatcaatga tgtagcattc tcatctttct    4680
atgtccacta cctttattc ctctaacgaa aattaaggtt gtgtagaagt cacatttttta    4740 atatagcaaa atttgccgca tgaaaaagct tcttcaagtg atgctaatag cgagttttcc    4800
```

-continued

| | |
|---|---|
| atcggttgag aagtctgaga tagagagaat catcagagag aaggcgacaa gggttgcgga | 4860 |
| aggaggagag gaagagaatg ttatggcaaa acgattgtct aaagaagcta tttcaaatgc | 4920 |
| agatgaagga tcttgagttc attcaacaac aaaacataga gccttaacaa tataggttgc | 4980 |
| aatggccaaa catgtttctt tttccagtcc ggattataaa aagaaggatt taactttta | 5040 |

<210> SEQ ID NO 2
<211> LENGTH: 1683
<212> TYPE: DNA
<213> ORGANISM: Arabidopsis thaliana
<220> FEATURE:
<223> OTHER INFORMATION: cDNA sequence of PMR6
<220> FEATURE:
<221> NAME/KEY: CDS
<222> LOCATION: (129)..(1634)

<400> SEQUENCE: 2

| | |
|---|---|
| tttcaaatcc ttctctgcta ctctctcttc acatttctct accaacattc ttcttctgac | 60 |
| actcaacaca cacactgcaa cttccacagc taaatctagc aacaccaagt caaaatccgc | 120 |
| cactaacg atg ctt ctt caa aac ttc tcc aac acc att ttc ctt ctc tgc<br>          Met Leu Leu Gln Asn Phe Ser Asn Thr Ile Phe Leu Leu Cys<br>          1               5                   10 | 170 |
| ctc ttc ttc aca ctc ctc tcc gcc act aaa ccc cta aat ctc act ctc<br>Leu Phe Phe Thr Leu Leu Ser Ala Thr Lys Pro Leu Asn Leu Thr Leu<br>15                  20                25                30 | 218 |
| cct cac caa cac cct tcc cct gat tcc gtc gct ctc cat gtc atc agg<br>Pro His Gln His Pro Ser Pro Asp Ser Val Ala Leu His Val Ile Arg<br>                35                   40                   45 | 266 |
| agt gta aat gaa tct ctt gca aga aga caa cta agc tca cca tca tca<br>Ser Val Asn Glu Ser Leu Ala Arg Arg Gln Leu Ser Ser Pro Ser Ser<br>          50                    55                  60 | 314 |
| tcc tca tca tca tca tcc tcc tca tca tca tcc tct tgc cgt acc gga<br>Ser Ser Ser Ser Ser Ser Ser Ser Ser Ser Ser Cys Arg Thr Gly<br>                65                    70                   75 | 362 |
| aac cca atc gac gat tgc tgg aga tgc agc gac gca gac tgg tca aca<br>Asn Pro Ile Asp Asp Cys Trp Arg Cys Ser Asp Ala Asp Trp Ser Thr<br>80                  85                90 | 410 |
| aac cga caa aga cta gca gac tgt tca atc ggc ttc gga cac ggc aca<br>Asn Arg Gln Arg Leu Ala Asp Cys Ser Ile Gly Phe Gly His Gly Thr<br>95                100              105              110 | 458 |
| ctc gga ggc aaa aac ggc aag atc tac gtc gta act gac tca tcc gac<br>Leu Gly Gly Lys Asn Gly Lys Ile Tyr Val Val Thr Asp Ser Ser Asp<br>                    115              120              125 | 506 |
| aac aac cca aca aac cca aca cca ggg aca ctc cgt tac ggc gta atc<br>Asn Asn Pro Thr Asn Pro Thr Pro Gly Thr Leu Arg Tyr Gly Val Ile<br>          130                    135                  140 | 554 |
| caa gaa gag cca ctc tgg atc gtc ttc tct tca aac atg ctc atc aga<br>Gln Glu Glu Pro Leu Trp Ile Val Phe Ser Ser Asn Met Leu Ile Arg<br>                145              150              155 | 602 |
| cta aaa caa gaa ctc atc atc aac agc tac aaa acc tta gat ggt cgt<br>Leu Lys Gln Glu Leu Ile Ile Asn Ser Tyr Lys Thr Leu Asp Gly Arg<br>160                  165              170 | 650 |
| ggc tca gcc gtt cac att acc gga aac ggt tgc tta act ctc caa tac<br>Gly Ser Ala Val His Ile Thr Gly Asn Gly Cys Leu Thr Leu Gln Tyr<br>175                  180              185              190 | 698 |
| gtt caa cac atc atc atc cac aac ctc cat atc tat gac tgt aaa cct<br>Val Gln His Ile Ile Ile His Asn Leu His Ile Tyr Asp Cys Lys Pro<br>                    195              200              205 | 746 |
| tca gct gga ttc gag aaa cgt ggt aga tcc gat gga gat ggg atc tcg<br>Ser Ala Gly Phe Glu Lys Arg Gly Arg Ser Asp Gly Asp Gly Ile Ser | 794 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 210 |     |     |     | 215 |     |     |     | 220 |     |     |     |      |
| atc | ttc | gga | tct | cag | aag | atc | tgg | gtt | gat | cat | tgt | tca | atg | agt | cat | 842  |
| Ile | Phe | Gly | Ser | Gln | Lys | Ile | Trp | Val | Asp | His | Cys | Ser | Met | Ser | His |      |
|     |     | 225 |     |     |     | 230 |     |     |     | 235 |     |     |     |     |     |      |
| tgc | acc | gac | ggg | cta | att | gat | gct | gtg | atg | ggt | tct | aca | gct | ata | act | 890  |
| Cys | Thr | Asp | Gly | Leu | Ile | Asp | Ala | Val | Met | Gly | Ser | Thr | Ala | Ile | Thr |      |
|     | 240 |     |     |     |     | 245 |     |     |     |     | 250 |     |     |     |     |      |
| ata | tct | aac | aat | tac | ttc | acc | cac | cac | gac | gag | gtt | atg | ttg | ttg | ggt | 938  |
| Ile | Ser | Asn | Asn | Tyr | Phe | Thr | His | His | Asp | Glu | Val | Met | Leu | Leu | Gly |      |
| 255 |     |     |     |     | 260 |     |     |     |     | 265 |     |     |     |     | 270 |      |
| cat | gat | gat | aac | tat | gct | cct | gat | acg | ggg | atg | caa | gtg | acg | ata | gcg | 986  |
| His | Asp | Asp | Asn | Tyr | Ala | Pro | Asp | Thr | Gly | Met | Gln | Val | Thr | Ile | Ala |      |
|     |     |     |     | 275 |     |     |     |     | 280 |     |     |     |     | 285 |     |      |
| ttt | aat | cat | ttc | gga | caa | ggg | ctt | gtt | cag | agg | atg | cct | agg | tgt | cgg | 1034 |
| Phe | Asn | His | Phe | Gly | Gln | Gly | Leu | Val | Gln | Arg | Met | Pro | Arg | Cys | Arg |      |
|     |     | 290 |     |     |     |     | 295 |     |     |     |     | 300 |     |     |     |      |
| aga | ggt | tac | att | cat | gta | gtg | aat | aat | gat | ttc | act | gag | tgg | aaa | atg | 1082 |
| Arg | Gly | Tyr | Ile | His | Val | Val | Asn | Asn | Asp | Phe | Thr | Glu | Trp | Lys | Met |      |
|     | 305 |     |     |     |     | 310 |     |     |     |     | 315 |     |     |     |     |      |
| tat | gct | att | ggt | ggt | agt | ggt | aat | ccc | acc | att | aac | agt | caa | gga | aat | 1130 |
| Tyr | Ala | Ile | Gly | Gly | Ser | Gly | Asn | Pro | Thr | Ile | Asn | Ser | Gln | Gly | Asn |      |
| 320 |     |     |     |     | 325 |     |     |     |     | 330 |     |     |     |     |     |      |
| cgt | tac | tct | gct | cct | tct | gat | cct | agc | gcc | aaa | gag | gtg | acg | aag | cga | 1178 |
| Arg | Tyr | Ser | Ala | Pro | Ser | Asp | Pro | Ser | Ala | Lys | Glu | Val | Thr | Lys | Arg |      |
| 335 |     |     |     |     | 340 |     |     |     |     | 345 |     |     |     |     | 350 |      |
| gtg | gac | tcg | aag | gac | gat | ggt | gaa | tgg | tcg | aat | tgg | aat | tgg | aga | aca | 1226 |
| Val | Asp | Ser | Lys | Asp | Asp | Gly | Glu | Trp | Ser | Asn | Trp | Asn | Trp | Arg | Thr |      |
|     |     |     | 355 |     |     |     |     | 360 |     |     |     |     | 365 |     |     |      |
| gaa | ggg | gat | ttg | atg | gag | aat | gga | gct | ttc | ttt | gtg | gcc | tct | ggt | gaa | 1274 |
| Glu | Gly | Asp | Leu | Met | Glu | Asn | Gly | Ala | Phe | Phe | Val | Ala | Ser | Gly | Glu |      |
|     |     |     | 370 |     |     |     |     | 375 |     |     |     |     | 380 |     |     |      |
| gga | atg | agc | tca | atg | tac | tct | aaa | gct | tct | agt | gtt | gac | cct | aaa | gct | 1322 |
| Gly | Met | Ser | Ser | Met | Tyr | Ser | Lys | Ala | Ser | Ser | Val | Asp | Pro | Lys | Ala |      |
|     |     | 385 |     |     |     |     | 390 |     |     |     |     | 395 |     |     |     |      |
| gct | tct | ctc | gta | gac | cag | ctc | act | cga | aac | gct | ggc | gtt | ttt | ggc | ggt | 1370 |
| Ala | Ser | Leu | Val | Asp | Gln | Leu | Thr | Arg | Asn | Ala | Gly | Val | Phe | Gly | Gly |      |
|     | 400 |     |     |     |     | 405 |     |     |     |     | 410 |     |     |     |     |      |
| ccc | agg | gat | gat | caa | ggt | cag | agt | ggc | aat | tct | tac | tct | cct | tat | gga | 1418 |
| Pro | Arg | Asp | Asp | Gln | Gly | Gln | Ser | Gly | Asn | Ser | Tyr | Ser | Pro | Tyr | Gly |      |
| 415 |     |     |     |     | 420 |     |     |     |     | 425 |     |     |     |     | 430 |      |
| ggc | gac | ggc | ggt | ggc | ggt | ggg | agc | agc | ggt | ggg | agc | agc | ggt | gga | ggg | 1466 |
| Gly | Asp | Gly | Gly | Gly | Gly | Gly | Ser | Ser | Gly | Gly | Ser | Ser | Gly | Gly | Gly |      |
|     |     |     |     | 435 |     |     |     |     | 440 |     |     |     |     | 445 |     |      |
| atg | gac | gtt | atg | gga | ggt | acg | acg | aga | gga | agc | agc | agc | agc | agc | ggc | 1514 |
| Met | Asp | Val | Met | Gly | Gly | Thr | Thr | Arg | Gly | Ser | Ser | Ser | Ser | Ser | Gly |      |
|     |     |     | 450 |     |     |     |     | 455 |     |     |     |     | 460 |     |     |      |
| gat | gac | agc | aat | gtc | ttc | cag | atg | ata | ttt | gga | agc | gat | gca | ccg | tct | 1562 |
| Asp | Asp | Ser | Asn | Val | Phe | Gln | Met | Ile | Phe | Gly | Ser | Asp | Ala | Pro | Ser |      |
|     |     | 465 |     |     |     |     | 470 |     |     |     |     | 475 |     |     |     |      |
| cgg | ccg | cgt | tta | acg | tta | ttg | ttt | tct | ttg | tta | atg | att | tcg | gtt | ttg | 1610 |
| Arg | Pro | Arg | Leu | Thr | Leu | Leu | Phe | Ser | Leu | Leu | Met | Ile | Ser | Val | Leu |      |
|     | 480 |     |     |     |     | 485 |     |     |     |     | 490 |     |     |     |     |      |
| tcg | tta | tca | act | cta | tta | ttg | tga | cgaatggata | | acaaatagga | | tttggaccgt | | | | 1664 |
| Ser | Leu | Ser | Thr | Leu | Leu | Leu |     |     |     |     |     |     |     |     |     |      |
| 495 |     |     |     | 500 |     |     |     |     |     |     |     |     |     |     |     |      | tcaattgatt ggttttttgg                                                   1683

<210> SEQ ID NO 3
<211> LENGTH: 501

<212> TYPE: PRT
<213> ORGANISM: Arabidopsis thaliana
<220> FEATURE:
<223> OTHER INFORMATION: cDNA sequence of PMR6

<400> SEQUENCE: 3

```
Met Leu Leu Gln Asn Phe Ser Asn Thr Ile Phe Leu Cys Leu Phe
 1               5                  10                  15

Phe Thr Leu Leu Ser Ala Thr Lys Pro Leu Asn Leu Thr Leu Pro His
                20                  25                  30

Gln His Pro Ser Pro Asp Ser Val Ala Leu His Val Ile Arg Ser Val
                35                  40                  45

Asn Glu Ser Leu Ala Arg Arg Gln Leu Ser Ser Pro Ser Ser Ser Ser
    50                  55                  60

Ser Ser Ser Ser Ser Ser Ser Ser Ser Cys Arg Thr Gly Asn Pro
 65                  70                  75                  80

Ile Asp Asp Cys Trp Arg Cys Ser Asp Ala Asp Trp Ser Thr Asn Arg
                85                  90                  95

Gln Arg Leu Ala Asp Cys Ser Ile Gly Phe Gly His Gly Thr Leu Gly
                100                 105                 110

Gly Lys Asn Gly Lys Ile Tyr Val Val Thr Asp Ser Ser Asp Asn Asn
                115                 120                 125

Pro Thr Asn Pro Thr Pro Gly Thr Leu Arg Tyr Gly Val Ile Gln Glu
    130                 135                 140

Glu Pro Leu Trp Ile Val Phe Ser Ser Asn Met Leu Ile Arg Leu Lys
145                 150                 155                 160

Gln Glu Leu Ile Ile Asn Ser Tyr Lys Thr Leu Asp Gly Arg Gly Ser
                165                 170                 175

Ala Val His Ile Thr Gly Asn Gly Cys Leu Thr Leu Gln Tyr Val Gln
                180                 185                 190

His Ile Ile Ile His Asn Leu His Ile Tyr Asp Cys Lys Pro Ser Ala
                195                 200                 205

Gly Phe Glu Lys Arg Gly Arg Ser Asp Gly Asp Gly Ile Ser Ile Phe
    210                 215                 220

Gly Ser Gln Lys Ile Trp Val Asp His Cys Ser Met Ser His Cys Thr
225                 230                 235                 240

Asp Gly Leu Ile Asp Ala Val Met Gly Ser Thr Ala Ile Thr Ile Ser
                245                 250                 255

Asn Asn Tyr Phe Thr His His Asp Glu Val Met Leu Leu Gly His Asp
                260                 265                 270

Asp Asn Tyr Ala Pro Asp Thr Gly Met Gln Val Thr Ile Ala Phe Asn
    275                 280                 285

His Phe Gly Gln Gly Leu Val Gln Arg Met Pro Arg Cys Arg Arg Gly
    290                 295                 300

Tyr Ile His Val Val Asn Asn Asp Phe Thr Glu Trp Lys Met Tyr Ala
305                 310                 315                 320

Ile Gly Gly Ser Gly Asn Pro Thr Ile Asn Ser Gln Gly Asn Arg Tyr
                325                 330                 335

Ser Ala Pro Ser Asp Pro Ser Ala Lys Glu Val Thr Lys Arg Val Asp
                340                 345                 350

Ser Lys Asp Asp Gly Glu Trp Ser Asn Trp Asn Trp Arg Thr Glu Gly
    355                 360                 365

Asp Leu Met Glu Asn Gly Ala Phe Phe Val Ala Ser Gly Glu Gly Met
    370                 375                 380
```

```
Ser Ser Met Tyr Ser Lys Ala Ser Ser Val Asp Pro Lys Ala Ala Ser
385                 390                 395                 400

Leu Val Asp Gln Leu Thr Arg Asn Ala Gly Val Phe Gly Gly Pro Arg
                405                 410                 415

Asp Asp Gln Gly Gln Ser Gly Asn Ser Tyr Ser Pro Tyr Gly Gly Asp
            420                 425                 430

Gly Gly Gly Gly Gly Ser Ser Gly Gly Ser Ser Gly Gly Gly Met Asp
            435                 440                 445

Val Met Gly Gly Thr Thr Arg Gly Ser Ser Ser Ser Ser Gly Asp Asp
            450                 455                 460

Ser Asn Val Phe Gln Met Ile Phe Gly Ser Asp Ala Pro Ser Arg Pro
465                 470                 475                 480

Arg Leu Thr Leu Leu Phe Ser Leu Leu Met Ile Ser Val Leu Ser Leu
                485                 490                 495

Ser Thr Leu Leu Leu
                500

<210> SEQ ID NO 4
<211> LENGTH: 2520
<212> TYPE: DNA
<213> ORGANISM: Arabidopsis thaliana
<220> FEATURE:
<223> OTHER INFORMATION: genomic sequence of portion of clone MDF20

<400> SEQUENCE: 4
ctcttgaaag ctctgatggc gggaaacaaa ggttggatga gaatctgaaa aggttggtac      60
tgtgtgatga tgaatttgcc gtattgaatc ccatcgaaga atgggtagaa gtaacagacg     120
gctgagatta tccgatccga tgcatcgacg gaatcatcac ccttggattg gagtacgagt     180
gtggcggctc tgtccctgga aagtctaggt tttgggaatt gggtatcaag gtttagaggg     240
agaaaagaac gaccggttag ggttagggtt ccggtgagag atggtaatgg agcaaaaaac     300
tgagatatta ttgccatttt gctctgtttt tgtttcactt cacacaaaac tgaaagactg     360
cttaacacat gatgagagga taataaacta aactccactc tgttttaaaa gtttagctta     420
aaacattgtg tcgtcttctt atctttctaa tatgataaaa cggtacgtag ttatttgaag     480
taaggtaaca attaaatagc ctctgttatt gtctttgttt tttgtgtata tttaaatatc     540
aaaatccacc ggtataaaac ggcgtaatgc ctttgtattg gacccaattc tttcaatttt     600
cacctaattt aattacctcc gtatttattt tttagtgcac ttcaatgtct cttgcatata     660
tatattggag caaattataa acataatgtt catagtgaaa ttgttagttg gttttaatct     720 cttttttaaga caacatataa tgtcaattgt atgtacgttt ttcttgtttc tcttaaacac     780
ttcttttgcg tttgcatttg cgattcctaa accgccaata gtaaggagac tatcaacgac     840
agtgacatca aattcaacag cgtcttcttg ctcagccaat ggaaatccaa tcgatgagtg     900
ttggagatgc gacgaaaact ggaaggacaa ccgcaaaaac ctcgcggatt gcgcggttgg     960
attcggacgc gactcaattg gcggtagagc cggggagttc tacacggtga ctgattcagg    1020
agacgacaat cctctaaatc caactccagg tacattacgg tacgctgcga cacaagatca    1080
acctctatgg atcatttttg atcgagacat ggtaatacaa ctaaaacaag atcttcaagt    1140
agcttcatac aaaaccattg atggtagagg aaataacgta caaatagctt atggaccgtg    1200
tttaacttta tataaagtta gtaacattat tataaacaat ctttatattc acgattgtgt    1260
tcccgtgaaa cggaatgctt tatcgtcgtt gggaggatac tcggatggag atggaatatc    1320
gatattcgag tctcgagata tttggattga tcattgtacg ttagagaaat gttacgatgg    1380
```

-continued

```
gcttattgat gcggtgaatg gatccacgga tataacgatt tcgaatagtt acatgttgaa     1440
tcataatgaa gtcatgcttt tgggccatag tgatgagtat tccggtgatc gggatatgcg     1500
agttacgatc gcgtttaact attttggtga aggacttgtc caaagaatgc aaggttagt      1560 acaatcttat atttcttttt cttctttttt taatgtcaaa tttataagct aaccaaaata     1620
ttcgtgctta aaataccaat gtgtaggtgt aggcatggat attttcacat agtgaataac     1680
atttatagag actggaagat gtatgctatt ggtggaagtg ctaatccaac gatctttagc     1740
caaggaaatg ttttcatagc ttccaataat cagttcacca aggaggtacg ttcgtgacat     1800
gtgctccaca aaactaagag cgttttaacc tcacaattag tacaatctaa ttcatagtcg     1860
actaatcatt tagaaatttg attttcatgt gtcttactat atggattaga ttctagacgg     1920
aaatgtttgc tccatacttc taaactcaca tgccctatac gcaggttaca aagcgagaga     1980
gtgcagatgg agacgaagaa tggaaggaat ggaactggaa atcagaagga gacgaaatgg     2040
ttaacggagc tttctttaca ccgtcaggga agaggattc tccgagctac gcgaaatttt      2100
cgagtatggt agctcgacca gcttcacttc tcaagaccac acatccatca gtaggtgttc     2160
ttagttgcga aattgaccaa gcttgttaaa aacacaaaca taagcttgtg accaaatcta     2220
gtgtttgtcc ttcttttttct tttttgctct tctacttgtt gtggttattg ttatcgtaaa    2280
taggatttgt actgaatgtg atgatgatca tagacccaaa caacaattgt tcattgtcaa     2340
tttctttacc aaaaaatttc ttttacgagt cacaaagttt cgtcagtttt tttatttata    2400
aatacattaa aattacttaa caaccttttt ccatcggata aaactaagat tgacactcat     2460
cattaataat tttatatata ctcccatttt ttttagtgag tgttaacata agattaggaa    2520
```

<210> SEQ ID NO 5
<211> LENGTH: 1424
<212> TYPE: DNA
<213> ORGANISM: Arabidopsis thaliana
<220> FEATURE:
<223> OTHER INFORMATION: cDNA sequence of portion of clone MDF20
<220> FEATURE:
<221> NAME/KEY: CDS
<222> LOCATION: (97)..(1329)

<400> SEQUENCE: 5

```
ctttcaattt tcacctaatt taattacctc cgtatttatt ttttagtgca cttcaatgtc      60
tcttgcatat atatattgga gcaaattata aacata atg ttc ata gtg aaa ttg       114
                                        Met Phe Ile Val Lys Leu
                                         1               5 tta gtt ggt ttt aat ctc ttt tta aga caa cat ata atg tca att gta      162
Leu Val Gly Phe Asn Leu Phe Leu Arg Gln His Ile Met Ser Ile Val
         10                  15                  20 tgt acg ttt ttc ttg ttt ctc tta aac act tct ttt gcg ttt gca ttt     210
Cys Thr Phe Phe Leu Phe Leu Leu Asn Thr Ser Phe Ala Phe Ala Phe
     25                  30                  35 gcg att cct aaa ccg cca ata gta agg aga cta tca acg aca gtg aca     258
Ala Ile Pro Lys Pro Pro Ile Val Arg Arg Leu Ser Thr Thr Val Thr
 40                  45                  50 tca aat tca aca gcg tct tct tgc tca gcc aat gga aat cca atc gat     306
Ser Asn Ser Thr Ala Ser Ser Cys Ser Ala Asn Gly Asn Pro Ile Asp
 55                  60                  65                  70 gag tgt tgg aga tgc gac gaa aac tgg aag gac aac cgc aaa aac ctc     354
Glu Cys Trp Arg Cys Asp Glu Asn Trp Lys Asp Asn Arg Lys Asn Leu
             75                  80                  85 gcg gat tgc gcg gtt gga ttc gga cgc gac tca att ggc ggt aga gcc     402
```

|     |     |     |     |     |     |     |     |     |     |     |     |     |     |     |
|---|---|---|---|---|---|---|---|---|---|---|---|---|---|---|
| Ala | Asp | Cys | Ala | Val | Gly | Phe | Gly | Arg | Asp | Ser | Ile | Gly | Gly | Arg | Ala |
|  |  |  | 90 |  |  |  |  | 95 |  |  |  | 100 |  |  |  |

| ggg | gag | ttc | tac | acg | gtg | act | gat | tca | gga | gac | gac | aat | cct | cta | aat | 450 |
|---|---|---|---|---|---|---|---|---|---|---|---|---|---|---|---|---|
| Gly | Glu | Phe | Tyr | Thr | Val | Thr | Asp | Ser | Gly | Asp | Asp | Asn | Pro | Leu | Asn |  |
|  |  | 105 |  |  |  |  | 110 |  |  |  |  | 115 |  |  |  |  |

| cca | act | cca | ggt | aca | tta | cgg | tac | gct | gcg | aca | caa | gat | caa | cct | cta | 498 |
|---|---|---|---|---|---|---|---|---|---|---|---|---|---|---|---|---|
| Pro | Thr | Pro | Gly | Thr | Leu | Arg | Tyr | Ala | Ala | Thr | Gln | Asp | Gln | Pro | Leu |  |
|  | 120 |  |  |  |  | 125 |  |  |  |  | 130 |  |  |  |  |  |

| tgg | atc | att | ttt | gat | cga | gac | atg | gta | ata | caa | cta | aaa | caa | gat | ctt | 546 |
|---|---|---|---|---|---|---|---|---|---|---|---|---|---|---|---|---|
| Trp | Ile | Ile | Phe | Asp | Arg | Asp | Met | Val | Ile | Gln | Leu | Lys | Gln | Asp | Leu |  |
| 135 |  |  |  |  | 140 |  |  |  |  | 145 |  |  |  |  | 150 |  |

| caa | gta | gct | tca | tac | aaa | acc | att | gat | ggt | aga | gga | aat | aac | gta | caa | 594 |
|---|---|---|---|---|---|---|---|---|---|---|---|---|---|---|---|---|
| Gln | Val | Ala | Ser | Tyr | Lys | Thr | Ile | Asp | Gly | Arg | Gly | Asn | Asn | Val | Gln |  |
|  |  |  |  | 155 |  |  |  |  | 160 |  |  |  |  | 165 |  |  |

| ata | gct | tat | gga | ccg | tgt | tta | act | tta | tat | aaa | gtt | agt | aac | att | att | 642 |
|---|---|---|---|---|---|---|---|---|---|---|---|---|---|---|---|---|
| Ile | Ala | Tyr | Gly | Pro | Cys | Leu | Thr | Leu | Tyr | Lys | Val | Ser | Asn | Ile | Ile |  |
|  |  |  | 170 |  |  |  |  | 175 |  |  |  |  | 180 |  |  |  |

| ata | aac | aat | ctt | tat | att | cac | gat | tgt | gtt | ccc | gtg | aaa | cgg | aat | gct | 690 |
|---|---|---|---|---|---|---|---|---|---|---|---|---|---|---|---|---|
| Ile | Asn | Asn | Leu | Tyr | Ile | His | Asp | Cys | Val | Pro | Val | Lys | Arg | Asn | Ala |  |
|  |  | 185 |  |  |  |  | 190 |  |  |  |  | 195 |  |  |  |  |

| tta | tcg | tcg | ttg | gga | gga | tac | tcg | gat | gga | gat | gga | ata | tcg | ata | ttc | 738 |
|---|---|---|---|---|---|---|---|---|---|---|---|---|---|---|---|---|
| Leu | Ser | Ser | Leu | Gly | Gly | Tyr | Ser | Asp | Gly | Asp | Gly | Ile | Ser | Ile | Phe |  |
|  | 200 |  |  |  |  | 205 |  |  |  |  | 210 |  |  |  |  |  |

| gag | tct | cga | gat | att | tgg | att | gat | cat | tgt | acg | tta | gag | aaa | tgt | tac | 786 |
|---|---|---|---|---|---|---|---|---|---|---|---|---|---|---|---|---|
| Glu | Ser | Arg | Asp | Ile | Trp | Ile | Asp | His | Cys | Thr | Leu | Glu | Lys | Cys | Tyr |  |
| 215 |  |  |  |  | 220 |  |  |  |  | 225 |  |  |  |  | 230 |  |

| gat | ggg | ctt | att | gat | gcg | gtg | aat | gga | tcc | acg | gat | ata | acg | att | tcg | 834 |
|---|---|---|---|---|---|---|---|---|---|---|---|---|---|---|---|---|
| Asp | Gly | Leu | Ile | Asp | Ala | Val | Asn | Gly | Ser | Thr | Asp | Ile | Thr | Ile | Ser |  |
|  |  |  |  | 235 |  |  |  |  | 240 |  |  |  |  | 245 |  |  |

| aat | agt | tac | atg | ttg | aat | cat | aat | gaa | gtc | atg | ctt | ttg | ggc | cat | agt | 882 |
|---|---|---|---|---|---|---|---|---|---|---|---|---|---|---|---|---|
| Asn | Ser | Tyr | Met | Leu | Asn | His | Asn | Glu | Val | Met | Leu | Leu | Gly | His | Ser |  |
|  |  |  | 250 |  |  |  |  | 255 |  |  |  |  | 260 |  |  |  |

| gat | gag | tat | tcc | ggt | gat | cgg | gat | atg | cga | gtt | acg | atc | gcg | ttt | aac | 930 |
|---|---|---|---|---|---|---|---|---|---|---|---|---|---|---|---|---|
| Asp | Glu | Tyr | Ser | Gly | Asp | Arg | Asp | Met | Arg | Val | Thr | Ile | Ala | Phe | Asn |  |
|  |  | 265 |  |  |  |  | 270 |  |  |  |  | 275 |  |  |  |  |

| tat | ttt | ggt | gaa | gga | ctt | gtc | caa | aga | atg | cca | agg | tgt | agg | cat | gga | 978 |
|---|---|---|---|---|---|---|---|---|---|---|---|---|---|---|---|---|
| Tyr | Phe | Gly | Glu | Gly | Leu | Val | Gln | Arg | Met | Pro | Arg | Cys | Arg | His | Gly |  |
|  | 280 |  |  |  |  | 285 |  |  |  |  | 290 |  |  |  |  |  |

| tat | ttt | cac | ata | gtg | aat | aac | att | tat | aga | gac | tgg | aag | atg | tat | gct | 1026 |
|---|---|---|---|---|---|---|---|---|---|---|---|---|---|---|---|---|
| Tyr | Phe | His | Ile | Val | Asn | Asn | Ile | Tyr | Arg | Asp | Trp | Lys | Met | Tyr | Ala |  |
| 295 |  |  |  |  | 300 |  |  |  |  | 305 |  |  |  |  | 310 |  |

| att | ggt | gga | agt | gct | aat | cca | acg | atc | ttt | agc | caa | gga | aat | gtt | ttc | 1074 |
|---|---|---|---|---|---|---|---|---|---|---|---|---|---|---|---|---|
| Ile | Gly | Gly | Ser | Ala | Asn | Pro | Thr | Ile | Phe | Ser | Gln | Gly | Asn | Val | Phe |  |
|  |  |  |  | 315 |  |  |  |  | 320 |  |  |  |  | 325 |  |  |

| ata | gct | tcc | aat | aat | cag | ttc | acc | aag | gag | gtt | aca | aag | cga | gag | agt | 1122 |
|---|---|---|---|---|---|---|---|---|---|---|---|---|---|---|---|---|
| Ile | Ala | Ser | Asn | Asn | Gln | Phe | Thr | Lys | Glu | Val | Thr | Lys | Arg | Glu | Ser |  |
|  |  |  | 330 |  |  |  |  | 335 |  |  |  |  | 340 |  |  |  |

| gca | gat | gga | gac | gaa | gaa | tgg | aag | gaa | tgg | aac | tgg | aaa | tca | gaa | gga | 1170 |
|---|---|---|---|---|---|---|---|---|---|---|---|---|---|---|---|---|
| Ala | Asp | Gly | Asp | Glu | Glu | Trp | Lys | Glu | Trp | Asn | Trp | Lys | Ser | Glu | Gly |  |
|  |  | 345 |  |  |  |  | 350 |  |  |  |  | 355 |  |  |  |  |

| gac | gaa | atg | gtt | aac | gga | gct | ttc | ttt | aca | ccg | tca | ggg | aaa | gag | gat | 1218 |
|---|---|---|---|---|---|---|---|---|---|---|---|---|---|---|---|---|
| Asp | Glu | Met | Val | Asn | Gly | Ala | Phe | Phe | Thr | Pro | Ser | Gly | Lys | Glu | Asp |  |
|  |  | 360 |  |  |  |  | 365 |  |  |  |  | 370 |  |  |  |  |

| tct | ccg | agc | tac | gcg | aaa | ttt | tcg | agt | atg | gta | gct | cga | cca | gct | tca | 1266 |
|---|---|---|---|---|---|---|---|---|---|---|---|---|---|---|---|---|
| Ser | Pro | Ser | Tyr | Ala | Lys | Phe | Ser | Ser | Met | Val | Ala | Arg | Pro | Ala | Ser |  |
| 375 |  |  |  | 380 |  |  |  |  | 385 |  |  |  |  | 390 |  |  |

| ctt | ctc | aag | acc | aca | cat | cca | tca | gta | ggt | gtt | ctt | agt | tgc | gaa | att | 1314 |
|---|---|---|---|---|---|---|---|---|---|---|---|---|---|---|---|---|
| Leu | Leu | Lys | Thr | Thr | His | Pro | Ser | Val | Gly | Val | Leu | Ser | Cys | Glu | Ile |  |
|  |  |  |  | 395 |  |  |  |  | 400 |  |  |  |  | 405 |  |  |

```
gac caa gct tgt taa aaacacaaac ataagcttgt gaccaaatct agtgtttgtc    1369
Asp Gln Ala Cys
        410 cttctttttc tttttgctc ttctacttgt tgtggttatt gttatcgtaa atagg        1424
```

<210> SEQ ID NO 6
<211> LENGTH: 410
<212> TYPE: PRT
<213> ORGANISM: Arabidopsis thaliana
<220> FEATURE:
<223> OTHER INFORMATION: cDNA sequence of portion of clone MDF20

<400> SEQUENCE: 6

```
Met Phe Ile Val Lys Leu Leu Val Gly Phe Asn Leu Phe Leu Arg Gln
 1               5                  10                  15

His Ile Met Ser Ile Val Cys Thr Phe Leu Phe Leu Leu Asn Thr
                20                  25                  30

Ser Phe Ala Phe Ala Phe Ala Ile Pro Lys Pro Pro Ile Val Arg Arg
                35                  40                  45

Leu Ser Thr Thr Val Thr Ser Asn Ser Thr Ala Ser Ser Cys Ser Ala
        50                  55                  60

Asn Gly Asn Pro Ile Asp Glu Cys Trp Arg Cys Asp Glu Asn Trp Lys
65                  70                  75                  80

Asp Asn Arg Lys Asn Leu Ala Asp Cys Ala Val Gly Phe Gly Arg Asp
                85                  90                  95

Ser Ile Gly Gly Arg Ala Gly Glu Phe Tyr Thr Val Thr Asp Ser Gly
            100                 105                 110

Asp Asp Asn Pro Leu Asn Pro Thr Pro Gly Thr Leu Arg Tyr Ala Ala
            115                 120                 125

Thr Gln Asp Gln Pro Leu Trp Ile Ile Phe Asp Arg Asp Met Val Ile
        130                 135                 140

Gln Leu Lys Gln Asp Leu Gln Val Ala Ser Tyr Lys Thr Ile Asp Gly
145                 150                 155                 160

Arg Gly Asn Asn Val Gln Ile Ala Tyr Gly Pro Cys Leu Thr Leu Tyr
                165                 170                 175

Lys Val Ser Asn Ile Ile Ile Asn Asn Leu Tyr Ile His Asp Cys Val
                180                 185                 190

Pro Val Lys Arg Asn Ala Leu Ser Ser Leu Gly Gly Tyr Ser Asp Gly
            195                 200                 205

Asp Gly Ile Ser Ile Phe Glu Ser Arg Asp Ile Trp Ile Asp His Cys
        210                 215                 220

Thr Leu Glu Lys Cys Tyr Asp Gly Leu Ile Asp Ala Val Asn Gly Ser
225                 230                 235                 240

Thr Asp Ile Thr Ile Ser Asn Ser Tyr Met Leu Asn His Asn Glu Val
                245                 250                 255

Met Leu Leu Gly His Ser Asp Glu Tyr Ser Gly Asp Arg Asp Met Arg
            260                 265                 270

Val Thr Ile Ala Phe Asn Tyr Phe Gly Glu Gly Leu Val Gln Arg Met
        275                 280                 285

Pro Arg Cys Arg His Gly Tyr Phe His Ile Val Asn Asn Ile Tyr Arg
            290                 295                 300

Asp Trp Lys Met Tyr Ala Ile Gly Gly Ser Ala Asn Pro Thr Ile Phe
305                 310                 315                 320

Ser Gln Gly Asn Val Phe Ile Ala Ser Asn Asn Gln Phe Thr Lys Glu
                325                 330                 335
```

```
Val Thr Lys Arg Glu Ser Ala Asp Gly Asp Glu Glu Trp Lys Glu Trp
            340                 345                 350

Asn Trp Lys Ser Glu Gly Asp Glu Met Val Asn Gly Ala Phe Phe Thr
        355                 360                 365

Pro Ser Gly Lys Glu Asp Ser Pro Ser Tyr Ala Lys Phe Ser Ser Met
    370                 375                 380

Val Ala Arg Pro Ala Ser Leu Leu Lys Thr Thr His Pro Ser Val Gly
385                 390                 395                 400

Val Leu Ser Cys Glu Ile Asp Gln Ala Cys
            405                 410

<210> SEQ ID NO 7
<211> LENGTH: 50000
<212> TYPE: DNA
<213> ORGANISM: Arabidopsis thaliana
<220> FEATURE:
<223> OTHER INFORMATION: nucleotides 1-50,000 of clone MDF20, GenBank
      No. AB009050

<400> SEQUENCE: 7
gatcatggga cgcatgtttg acttttttt ttttttaac atcttcatct tattgatatt      60
acgaagaaaa gtaatcaaag cgtaacgctg tgaaaattac aggtataccg tggtctttta    120
tctatggcaa ttttggtagg gaatgatttt acagtttttt ccctcataat ttcatgatat    180
tagataaatg aatatatgtg gattcaaata tttaaaattt ggatattttt taaaggatat    240
cgtctatata tatcaataac taaaaactaa gtaaaatttt tttaaaatgt tctaaatatt    300
tttctcgaat ttgttttttgg tataaacaat caataggttc aagattcatt tccacatcga   360
ctttagatat atcttaaaat aaatacctga ccaaaaatca aatcgtttca aaagatcaat    420
gctaagcaag gtttgtgtgt tcttgttga gattgatttg aatctgcatc tgcaatgaaa     480
agacttgaga gttttcatat tgattttaga cttgctaaga tgtgtgtttg tttgtgaagg    540
tgtgaagaaa gggattgtcg aaagttggga aaaacatgaa gaaagtgaga ctgatgaaga    600
cgatcttgat ataggcatta gtcctaatgc ctcttctgag aagaagaaga agaaggagtc    660
ttggcgttta gatggtcgag gaaaggtaaa agatttgctt atattcctct tcttgttgag    720
acaaatatag agttgagaaa gaattacttt ttttgtgttt tcgtctggta agttcgagca    780
agtatgtgga gaaactatac cctctactct gaggcgagaa tgatatagat ccgaaatggt    840
taccacttct ggattagttg agcacatttg gtttgaaaga atcacgcttt gttgaaatgt    900
acgagagaca catgccatcc cttcagatta aagtgttctc agcgcaagag agactcgatt    960
acttgttgtt aaggaaatta ggtagcaagt aatgatgaat accattagtt tatagagaga   1020
tccaatttct caaaggtttg tgttcttgtg tttgatggtt tcaacaccc ttaaaaagta    1080 aaccggtaaa attcatcgtg ggagtcaaaa ttggtagagt ttaacatgct tattattaat    1140
ttgcacaccc atttcagcat ttgacagttg tatgagtgta atccacacac aaaaaaattg    1200
tttagcaaat tgttatacac aaaacagaga ttaggtaata agaaaattag caaattgtta    1260
cagaaaatat attctcctaa gttgtctagc ctctagtatc ccgataccat acaatccaca   1320
aaacagagga tggaataaag tgagagagga aggaacagaa caatacataa gaaataaaaa   1380
gcaacataaa agattgggtg ttcttgtgag ttaattagaa gaagatgaaa tcgtgagatg   1440
tttcctagtg aacctggtga tccgtgatcg tgtgagtaaa ttcaggaaat caagatacat   1500
aatattgagt aacagaaact gccttgtttt tgttaacttt ttggtgtttc ggtacttccc   1560
tttgtacctt cactttgtct taacttgcct tttgtaaaga ttacgaacaa gttctaatat   1620
```

```
caatataatc tttcaaagaa aagaaactgc cttattttta ggaagtttat cttccgttac    1680
attatttttt attgtacttc ccttttttaa aaaaatatga cgtggcagaa aatgattggc    1740
catctaactt atgttttata atataaatga tggaatttag aacccgagca gtcgcacccc    1800
tcaccaacct tcgcactggc tgcaaatgca agcctttcct gttcttctca ttacacattt    1860
tcctatgttg tagccttcat gtaggcaaaa atctccacat agtatggcac cattaggttt    1920
attacatgtt gcaggcggtg ctcgtttgct tggattttta agatcacatg gatgtttacg    1980
ctttccttgt gtcattccta atagatttgt gaccaatgag ttagagatat tcaagcatat    2040
atatatatat atatatatat gtatatatat aaatataaat atattagatt tagttagatc    2100
taaataaaaa cacattatca ttaaaaaaaa tacaacgaac tgattttttag ttgtttcaca    2160
catcaatatt tgcattttca tttgctttt caagtatatt actctcttca tctcatgaag    2220
atatgttttc tagatattat tttttttgtca ttaaggtaaa agttttgggt ttccaatgta    2280
aaaccgttac ctatttttacc tttattaaac tattaagtaa tattatactc gagaatatta    2340
tacttttaaga cacttttttaa aaaacatttc cgtggttaga cactttctaa agagaaggca    2400
ctttaaatgg ataatttgac caatttaccc tctaaccata tatcgcttta tctctctcat    2460
cctcctattc tttctctctc tttctctcac gttgtcgaaa aataaacaaa actcaagcca    2520
aaaaaatata tttattcctt tttctttctt tcctcttcaa caaatcatca gcttttatga    2580
gaaagagaga ttgagattca ccttctttaa tttttcgcgt gtgctttgat ctgacttgaa    2640
ggaaaaaaat ttcagaccat caatttgaga atctgcccta tctggctgat ttagttacat    2700
gactcgctga atgcttgaat tggatttacg gtttggtttt cgttttatgt ttttgttgtt    2760
tgttgcaaaa ttaatctgat tacttgctct ttgattcttt atcttgcttt tccaatttca    2820
tattcgagat tattctcttg aattggagat taaagcctcg tagtggactt cgaatcgttt    2880
gatagtaatg gtcgaatcac tagttgatgg aactcgttgc ttagttcatg tctagtgaat    2940
ttgattcacg attatatttg ggttgtatat tttcagaaaa tctagttatt ttatgtgttc    3000
atcataaacg gtttataagt ttttttgatgg ttgattcact tactgaagaa ccatgttgct    3060
agttctggtt atgtgaaatt gatagaaatt ttagcttaga tctgagatta attttcattc    3120
acatatgtta gattgatttc tacatttgtg tttaagatat agatgttaaa aatttggtgc    3180
aaaatcgaga agattatctt aacacagtta aatgaacaga cctcagtgga caacaatttc    3240
tggacaacga tttctggaca cgttcttctt taccttttta tctcaaaatc caatcgagaa    3300
gatcatctta acagagttaa atgaacagac ctatgtggac aacaacttct cgacacgttc    3360
ttcccttgaa tttgtgatca tttatgttat attttgagat gttttgtata taaaatcaaa    3420
cttggacttg tatttttaaaa cttaaaaatc aaattgagaa gatcgtctta acagagttaa    3480
atgaacagac ctttgtggac aacacttttct ggacacgttc ttctttacca ttttatctca    3540
aaatccaatc aagaagatca tcttaacaga gttaaatgaa catacctatg tggacaacga    3600
cttgtggaca cgttcttccc ttgaatttgt gatcatttat gttatatttt gagtgtctat    3660
atacaagtga actaatgtgt tgaataagca aaaaaaacag atgatttgtt ttgaccaact    3720
tgtgattctt gcatcaccaa tgacactctt tcattaaaaa aaacaattga tgaaagctct    3780
acacatgaac catttgtgtt ccagtgtttg tcatgtttct atgtcatgtt tcaccattac    3840
gccatatggt caagtctaag tggacaattt atcatggact aaactatcat taactagttg    3900
ggttttgtgt gttgctattt gaaagcaatg tctacagatt gttcttgggt tttggagaca    3960
```

```
tctaagatta ttgggttcta cataaataat tggtgttgga agcttggata gtttgtctcc    4020
atgataactt gtccacgtaa acgtaaccat gtggaaataa gtgattctca taagcaaaag    4080
aatatgcttt taaggttaga cgttcaatga acatcaatt tattaagaaa gaatcaaatt     4140
gtaccaaaca aggcgatcaa atggatatga aatttaatac tggaatttgc taacttgggt    4200
tttccataaa ctctcaaatg tttgattttg ataaactctt aaatgtttga ttttgcaagg    4260
aaagaaaaaa aagtaataat gagaagagaa agagagagag agcgaaaaga agaagcgacg    4320
aagaagaagg aaaaaaaagg aacgtggaga gatgaaactt ttttttttaat tataattttt   4380 taattttcag gggcaaattg gtcaaaagtt taatgaaaaa gttggaaaag tgcctcatcc    4440
ctgacaagtg gctcaaaagg aataaaaattc tctaaaagtg cctaaacgtg tcacattccc   4500
tattatactc cctatgattt tttaaaaatt aattttctag aaaaaacata catattaaaa    4560
tatatattaa aaggtgatta tatatatata tataagtttt gtgatttaca tttcaataat   4620
tcgaagccaa tgattttcaa ttattttct gaagtttac aatttatcta tgataactaa     4680
taaatattgc atagaaaatc taaagaatc aaatttttta aaacaaatat ttttttttaga   4740 aaaccaatta attaagaaca gacggagtaa tgtattcttt aaagtgttta aagagaatat   4800
tatttcttaa agaatgttaa attgttagaa aacttatctt tgtgggacga agaaaatatt   4860
attttctttt aaaaaaagtt ttgtattgtt aaatctaaac atatacatca aactttaaaa   4920
atcaaagcaa aaaagaata tctctccttt tgcatgcttt tgacatattg aatttaatag    4980
ctaattttct taattaagat gttaaactta tggattcatg atttgaacaa aactgaaaaa   5040
aagtatatgg aagcgttggt gagattcata cctatcaaaa tgaacaaaag gatcaccaac   5100
cgaatagtaa aaccaactac tgtatttttt cttcttcttt cttaatttct ctctttatta   5160
aaaatttgtt aattatatca taatcttaac tgttgtatat aaagtatttc ttcctaaaat   5220
atacaaggtg tacgcaacaa atgccaataa aaatggtttc aaattaaaaa gaaagaccaa   5280
aactcatatg aacctcaaaa acatagtatg ctacttttag ttaaaataaa ctttctcatt   5340
tcaagttcta ttttttttgt cattcgctta gttattaatg ctcaaaaagc catttctgag   5400
gattgttatt tacataagtg acatgaagca tcacacgatc taaaagctgt tagaaccaca   5460
tacgaaggca aacacaatca ctatgtacta accgcaaggt ataacaacaa caacaacaac   5520
catgacatgt cagactagtt gtaccgctaa cacaatcagc ctcaacttag gtgttgaaat   5580
cgcatcggac acccttgacc atacatcaaa cgagcatcca catccacatc tgcatccgca   5640
tccgcattca catcgtgttc gttctgaact taaaccagtg gaacgctgga ttcaagttta   5700
ttcatggacc acccatggga acctgctatc taagtagcac taatgccggt ataatcatca   5760
atataacggt tcgagagaaa cgatcgaggc tcaaacagat gacatctctt cctgttatcc   5820
gtatatatcc acataacata gcaagaatac aatatggtct ctagaggagg atggtctgca   5880
caaaccaacc acagtaacac aataaagaaa aagaaaaaca aaggctctat acttgcatta   5940
tttatcttga ttcttcctag gttaggaatg gaataacatt gttctttgta atctatgatc   6000
tatatgtatg tatgtatgta tgtatatcat gacacactaa gatagagata ttggtcttaa   6060
tctcccaaca tatttatttg ttttttatta attcgaaaat gttttgtaaa aaaaaaacac   6120
aaagctttat atgtttccaa gaaaatctga ttgcagagat catcaacatc agcctgtaaa   6180
gaatcttctc catgactgcc atggaagaaa cccacctgca aataaaacag aaacaaacac   6240
taaagtatac tttacatttt tcaaaatgta aagaaagat atagagagaa atcgaagtta   6300
ccacattcag gacaacgaaa atacttttg tctcgagaaa caagtcctgt tcctccacat   6360
```

```
tcttcacatc tcttctgtgc aatctgaaac caaaactcat ttttcaatag acaacacaac    6420
caaataatta atgtatgtgt gtaataatac atactattct tttgctgaat caacacctg    6480 caacaacgaa tggtatgatt ccagctgcaa gatcaattga tttattataa gcttataaga    6540
aaaacacatt ttttaatcac atcactaatt agctaattaa ttaaattacc aatggttcca    6600
actataatct gccacgtaat ctccgatttg cctgtctccg ccaccgtgtc agctagttca    6660
cttagagccg acgtcgtttt gagccgtcga ttactcatcg tcatcatgcc gccgccgccg    6720
ccgcggcttc ttcttcttcc cggagaaacg aaaccagccg tggattttat ctgacgtggt    6780
cttgatctaa cggtccacag agacggaact ctacacagtg aagaagcctc cattgtcgcc    6840
attatgactc aagaaatcaa attcaccgat gaaaatatgt taaaaaaatt gggccacgtc    6900
gacgttattt cgggtcgggt tcgcgccaac cgcaaatacc atcgtgtggc tttaaaaaag    6960
ctgccaatca aaaatatatt ctaaaataca ttaaaacgac ggcgtgtaat cggaaaacag    7020
taaacgccat tagagtcttg tgtgtgttaa taatgaatct caaaacaaaa cttttttgtt    7080
tgtttgtttt ggaattaggg ttttagggta tattcgcaat cactctaatc ggataattcc    7140
tctactctgt taacattatc ttcttcttcg ttcctaccgc aaatggcggg tttctcactg    7200
tactgtttta aaaccctcg aattctcttt actcttccgt cggaatcacc tctctttgtt    7260
ttgggttctg ataaatgttc accggcgacg agacggccga gtagaaagac tcgtgggttt    7320
gtcgtgacgt acgcgcactc taatccgaag ataatcaatc cgaagaagaa gtcgaggtat    7380
gggcaaacgt tatctccata tgacagtgat gaagatgatg atgatgatga tgatgatgat    7440
gatgatgact ggttacttaa tgttagtttc ttttgttttc tcttatgaaa tttgtttgat    7500
tttgagatta agggttttaaa agatttgtct tttctttagg atgatttcgc tgaggttaca    7560
gagtatgaga agaagaagcc taagtcacat aagcaaacca ttgctaagaa agtttgtct    7620 tctcttgatt tgaatctgca tctgcaatga atgattttg ctaagatgtg ctttgtttg    7680 tgaaggtgtg aagaaaggga ttgtcaagcc tgaagaaagt gagactgatg aagatgatct    7740
tgatttaggc attagtccta atgccacttc tgagaagaag aaggagtctt ggcgtttaga    7800
tggtcgagga aaggtaaaaa gagttttgct taaatacctc ttctttgtcg ttgagttgag    7860
aaagttactc ttttttcttgt gtgtttcgtt agatgagttc gaggaagtat gtggagaaac    7920
tataccctcg gctcgcagaa gagattgata tagatccgaa atgtgtacca cttctggatt    7980
acttaagcac atttggtttg aaagagtcac actttgttca aatgtacgag agacacatgc    8040
catcccttca gattaatgtg ttctcagctc aagagagact cgattacttg ttgagtgtcg    8100
gtgttaaaca cagagatatc aagagaatgc tcttgagaca accacagata cttcaataca    8160
ctgttgagaa caatctcaaa gctcacattt cctttctaat gggtcttggc attcctaatt    8220
ccaaaatagg acagattgtt gctgctaccc cttctctctt ctcttacagt gtagagaatt    8280
cattgagacc tacgataagg tatctgatcg aagaggttgg gataaaggaa accgatgttg    8340
gaaaggttgt gcaacttagc cctcagattc tggttcagcg gctcgacata acatggaaca    8400
ctcgctacat gttcctctcc aaggagttag gagcacctag agacagcgta gtgaagatgg    8460
taaagaagca tccgcagctt cttcactaca gtatcgatga cgggttcttg cctcgaatca    8520
atttccttag gagcattggg atgtgcaatt ctgatatact gaaagtcttg actagcctta    8580
cacaggttag tagattgctt gattcttttt catacttaaa tcaaaactag aatgtttgtt    8640
ctcataaaca cttgtcaaat tggtctgaat aggttttgtc tctttcacta gaagataatc    8700
```

```
taaaacctaa gtacatgtat ttggtcaatg agctcaataa tgaagttcac attctgacca    8760
aatacccaat gtacttgagc ttgtccttgg atcaaaggat acgtccgcgc caccgcttct    8820
tggttgagtt aaagaaagtg cggaaagggc cattccctct tagttcatta gttccaaatg    8880
atgaaagctt ttgtcagcaa tgggctggaa ccagtgtaga tacgtatctc gcctttcgcc    8940
agaggctgtt actcaaggag tttgcaaaca agtatgacaa gagaggatga tgatgggaat    9000
ctcttcttct tgattaccga caataagtca acactttggt tagtttcctg cttcaaatcc    9060
ggtaaaagag gttcatatgc agaacctgtg aatgactcat taacttctgg tgaaacgcga    9120
gatactgcaa agattgaact ttttcaggaa agtaactcca gagaagccgg cttggcacag    9180
acatcatatt tgtttaccag atgagagttt cctcaatctt ttccaggttt tgtctacatt    9240
ttaagttctg ctatgtcttg tggtaaagtt ttactctctt tttctcctct tctttctaat    9300
gaatcatgga gaagagaaaa gaatccatgt gtagtatttt ttggcctagt atatatatac    9360
ttaatactaa taagagcatc ttataaaggt attgtttgtt atgtttgatc cttctacgga    9420
caagacgttg gaagaaagat ttttaagtta tgtagattga gtttctttgt gtgcttcttt    9480
actttatact ctatataaac attgtgtctt caataatttc tttgttaatt ttaattttt    9540
tggtaatagc ttcttttgaa caagaaaaaa aaagatcgtc ttggttgaat gactaaaccg    9600
tatatgtaaa acccatttgt ttattttcta cacaacacaa acacaaaatt acatacaacc    9660
aacatatcct gccattattt tactaataaa ttatcagcga aaacaacaa cttaagttga    9720
cctataaaaa tgtgaaaaac cagtgaatag aaatttgtta ccaaataaac catctttgct    9780
tttttgcaaa tgaacacgta attcttatga gtaaacgagc gcaaatctaa gaaaagagta    9840
aaccatcttt ggatttgcca aacccctcca acatcatgtt tgcagtttta ttcttctatg    9900
attaattaat catcttctga tttgcccttc atcttttcat tttcactcgt ttattacttt    9960
tctgtgcacc gaacaaaaaa gatggtgacc atttatgatt gttaagtttt atttgttcta   10020
gttactactc cataattaag aacttgcaat aactccatct tattttacc attatatata   10080
tatatatata tatatatttt tttccctagt atcttactca tgctccatac gtacttaatt   10140
tctcccataa attcataaag ataatctttt aaaacaaaaa tatagtcttg tttaacaaat   10200
aaacaatagt cattctcacc acacacacta aaaaaaatag acaatagtca atgtttgata   10260
gtctgaaatc gatagaaaag tgttcaaacc aaatcaatct gcaatatgga ctatagacat   10320
ctctacaata ataacgtgac aacataacgt aactatgagt ctgtgacatg tcaaatacac   10380
agtatacact caaggacatg tatacatata acacatggag catagcatag ctcatcattt   10440
agatttcttc taattacact actggtgatt ttcactcaga gtcagggaac cagccaatgt   10500
ggcttcaaaa actcctttgt aaagattcaa gttcataaat aaaattcagt ttgcagaaaa   10560
gaaaaaaaaa acagatggat cataattaat taatttccac ataaaagaa gtttctacca   10620
tataatcata ttactcataa aaatatatta atgtatctta aactaattac agacttattt   10680
attttttctga taaatataaa cataatcaaa tagatagagt tggattttaa gttaaatatc   10740
ctttgtattg tgtattaatc agaagaaata ttatttttaa taaacacaaa atcatatcta   10800
ggagatgagt atatatctct tccagcatat gtactttaat cttagtagtt atcaatcatt   10860
gcaaaaaata tatgttaaaa catatcctaa taaaaaaata atatattact atatgaaatt   10920
taaacacgtt attttcttgt atttaaatta tactaaattg atccttacag tatttctttg   10980
aattttttta tccttacaaa tgttaccaaa aaatattaat ttgtaagaag ataattacaa   11040
acaaaagaaa tgcaatgata aacaaaaaaa aaaaaaaggt taaaaagcgc aaacaaaaaa   11100
```

-continued

```
aatagaaatt aattgtgagg ataaatatta cataatttta tcttggagga tatgtaattt    11160
ttatttttt tattttgata agcatgatat atataatgga gatgatggta atgtttatgt     11220
ttgaggaagt taagagctac atagagaggc tccaagtatt tattaaactc atctttctca    11280
cacgacctt cacctccaaa gactcccaac aaaaatcata ataagaaat acaaaaacgt      11340
aaactttgcc aagttttttt ttcttccttt ctttaactct ctcactccca cgaattcgtg    11400
agaagaaacc ttaaaacgtt ttttttccag agcacgaaaa aactccccac ctcacttaaa    11460
cttttttcct tgtgcaggag acatcattcc ccatgaaagt cgaagctttt attcccgccg    11520
ttttattgct ctgttttggg gtaatgttat gtttaaaaag ctcgtgtgcg ttgcagatag    11580
gtaacaataa tgagttgaag aattacataa gttgggaaga tttgagagtt gtggaagatg    11640
gaagaataga gagaagtttt agcattaagg agaatagtaa ttgggtaacc acaaacgcta    11700
acgctaacgc gaacgctact aacgtgagaa gagtgattgt ggttgataaa acggaggag     11760
gagattctgt tacagttcaa ggagctgttg atatggttcc tgattccaat tcacagagag    11820
ttaaaatctt cattcttcct gggatttaca ggtaacttac aaaaaagat ttaagacata     11880
aaccgtgttt gtttttttct ttgtatgtta ttaatctttg agaaacgtct ttgggagtgt    11940
ggggttttgt ttccgaagat ttcgttttttt ttttttgtttt tttttggtgt gataaaagca  12000
gttgaagcta aattcttggg ttagtgggat aatctaagca taagctgctt acgtaaataa    12060
aatcgtgggt ctcaagaatc tttgtctgta aaaccgtaga ataagaatct ttgtctttgt    12120
tatatactct gttcttttt tgtcagaatc tttgtctttg ttatctactc ttgttttttt     12180
tcttcagaat ctcttctctg ctatgtgttg tttgcaggga aaggtgatt gtgccgaaat     12240
caaaaccgta tatttcgttc ataggtaatg agagctatgc gggagataca gtgattagtt    12300
ggagcgataa agcttcagac cttggctgcg atggtaaaga actcggcact tatagaaccg    12360
cctctgttc cattgaatct gatttcttct gtgctactgc catcactttt gaggtcctaa     12420
aaccctctct tttactatta ttccttgtct actttctatg tgtattgtgt tttatgttt     12480
tgaattgttt gtgatgtacg gattgaggca gaacacggtg gttgcagagg cagggggaaca   12540
ggggaggcaa gcggtggcgt tgagaataat tggggacaaa gctgtgttct atagagttag    12600
ggttttggga tcacaagaca ctctttttga tgacaatgga tctcactact tttaccaatg    12660
ctatatccaa ggcaatgtag atttcatctt tggcaatgcg aaatcacttt accaggcaaa    12720
accccttcca tttgatcttc ttaaatcctt tgtatcgaaa tccatttgta aagatattga    12780
tcgaagtttt ggtgtttggt aaccacagga ctgtgatatc cactcaaccg caaagagata    12840
tggcgcgatc gcggctcatc atagagactc ggagactgaa gataccgggt tctcctttgt    12900
gaactgtgat atcagtggta ctgggcagat ttacttagga agggcttggg gaaactactc    12960
aagaactgtt tattcaaact gtttcatagc tgatattatc actcctgtgg gctgagtga    13020
ctggaaacac cctgagaggc aaaggtaaaa aaaggatctt gaaaattgaa aactcatctc    13080
tgaaactaca gcatttctct ctcaaaacaa catcaagcga atttcttttg caggaaagtg    13140
atgttcgggg agtacaattg caggggaaga ggagcagaga gaggaggccg agtaccgtgg    13200
tcgaaaactc ttaccagaga tgaagtgaag ccttttctgg gaagagagtt catatatgga    13260
gatcaatggc tgagactcta aatcctttt caaccggaca taaggtccaa gctagctaac    13320
aggagatgat gatctaattc tactctattc atttgtaatt agtttgaatt tagagagaaa    13380
tagaatctgc atgttttaac tcataccaaa gtaaatgaaa cccaggtttt ggttttagat    13440
```

-continued

```
aaactaaatt tcttacaagc tgatacgaag tggttttaca tggagttttg tgacaataag    13500
gcaaaataca aatggatatc cttttctcct aataaacatt gcataaataa aacctaaaac    13560
aaccagtact aatgaatcct atgcttagat gattggttaa aacaaatgca accaccaaaa    13620
tcatgcctct tcaattttct atacaaccTT tacctactcc tctctcctca gcaccaacca    13680
agtcaaaccc agaatcactt tttctgcaaa ctatgtcaat ttatatatat acataaaaag    13740
aaacatcaac gtttccagag atgtggcacg taccagaatt accatcatta tgtatgactt    13800
caagcaagca tctttacgtt gtcaccagcg tggtagtagt ttttgatagg gtgaagactg    13860
attctgattt gcgggccttc tcatcattaa gggtaacatc atcttctttg tggtcctcca    13920
cggtattttc atggttgaca taggttttag tttcgttact tccaacctct ttatcctctt    13980
cttttgaaag tttgttttcg tcatcttcct taactaccac atctttatgc tctttgttct    14040
gttctcctaa aagggaattg tacgctttct caccttcagg ttctgcctcc tcaacaatat    14100
ttggcatagc actgggtttt gcctttgtgt cttttgaaag agtggacaac atggaaagct    14160
tggattccga gctactatca gaagatacaa tagcgagtat ttcgggttta ggatcgatat    14220
caacccagct atctcccacc cagtctctgg aaatccgaat atcctttctg agcactgtta    14280
agcataagtt ctcccctaac accgtgaaaa caaaacacat gttagtcgta aggcagagat    14340
ggagaaagtg gaggcaacta gagagtaaaa gatgaatata ggaacacact aaatcatacc    14400
agggatatat attttcaagt cctcagtatc cggtttgcca gtggcaatta caacaccttc    14460
ccaccaacca tcattccacc atgcatcaac agcttcacca attgtaagat caaagtatgc    14520
tgttttaaca tctcgaggag caggtcggat tgttgggcgg ttggacaacc ttataccaag    14580
cttgtcaggc atagcagatt taaaagccgg cacccattcc tacacaaaac aatgaggaaa    14640
aaaaacacaa ttaggtgaca aacataagat taaaatagct tccatttcca gaaactaaaa    14700
ttaaacagcc aatggctgtg gaagcaaata tatacctcaa ggtttccata tccatcctcg    14760
tcctctatat catcatactg gagttttacc tgtttccttg atacgtccag gacagtgcat    14820
ctaaaccaac agcctctaat accgctatct tgacacagaa actctatttt tgcatcagtc    14880
ttaaccactc cgttgtaaca aggatgtttc tgaacattgg ttggtgaagg aaatcttttg    14940
cccgaggcat taagttttag tctcttacat gaagattcgt aagttgttaa cagatgatca    15000
gacataattc ttgctcgttt tttcatgctt ctctcagcac caaccattac attctcaccc    15060
tcactccatt cttcatcttc ctctatattc atcgcacagt ctacaggacc agcctccata    15120
gaacttaagc aagacataat cggttggtcc aaatatccac gcaatttact caaatcaaaa    15180
ggtttaactt tgctgttcct gagttgccga tagcacatgt gtaccctTGC caataaagaa    15240
ttcggaaagg aagccacaca ctcctcataa tgctcacggg tcaagacagt ggcaggacca    15300
tcaacacatt ctgcactgat gacctgtgaa tgagggtgta taaaaacctc ttttgggttt    15360
gggttcttga gagcaactgc acccttcact tcttttgtgt agtgaaacca cctcactttg    15420 accttttta ggccacgctt atcctcatac atatcttcca gatatgcaac gtaccgatcc    15480
tccccttTGC tcaagacaaa gacaaaagat tgaacctgaa atccaaaag aagaattacg    15540 cctccaagtg agtagtctca tccaagatct ttacagatac aaatcacaag aacagtcaac    15600
atatatcgaa ctatgcatgc actgatgcca agtcttcaac ttaccccTAT tgttgtccca    15660
tttctgcaaa atgatgggta atgtttgagc tgtttaccac acatccaagg agctcctgac    15720
cacataatct cccaactgtg aataatcaag tttatgggaa gacggacctg taagagagat    15780
tttcccatca gtataacagg aaagtaaaat gcagtgacaa ttgtatgaga gcaacaagca    15840
```

```
gctaaacatc acctcttcac ttgcttgagc tcgctgagca gtaaatccat tgcttggaaa    15900
ttcgggagat ccattagatt cccctgactc acattttggt gactctgtaa atgacaatat    15960
aacaagtgct ttagaataat cagttataaa gttagaagag accaacataa aggaagaatt    16020
cattccttct ccactcaaca gacaatttgt cacatatggt aaaagataaa gataaatgcg    16080
tactcgacca gtttccttgt gtactctgct tagacagcat tgaagtgagc caatccacaa    16140
cttcccttct cgacctccat ttgaagccag aatgaattga attctcagga ccatgaatgc    16200
gcacaaactc ctcagagaca acatagaaca tgtgcctaac acttctctca gtaccaatga    16260
cagctaggat agattcaccg gcagaatcct tgaggaagta atgaacaaca cggttccctc    16320
gctcttggga gacaaaatgc tccttccact cgacaaaatg atgatcattc tcacacattt    16380
ttcaaaataa aattgattcg gcaagcatca aacgctccaa accctccttt acatcagata    16440
aaaacactaa ctactgccag ttcaaagtca agtcttttg tcctaaatca agttctaaag     16500
caaccccaac gcaacaatct ctatatacca atgacagtgg aaaccccttaa aaacctttaa   16560 tctaatgacc aaacaatacc cctaaaatca atccctgtg ccgtggaaat cctaaagcaa     16620
atcactctaa tgcataactc tgatcaacat ctttcccagc ttcctacaac acagctaaat    16680
cgtcgaagtc tctgtaaatt tccagctttt aagaaatcaa ataatccgga cgaagaagaa    16740
gttaggatta gagaaagcag ataagaaccc agtgagcgga gagttatgaa gatctgtaga    16800
aagatcagag actaagccat ggaaacactg atctaagctc gagagcgccg ccaaacacca    16860
agatacgact ttgactgcgg taatcagctt aagcatgacg aagacgaaat gggcatctca    16920
aaattttcag cttagaatag atttataccg attcctctaa ggtttgtaca gaacaaacaa    16980
atgattcagg agaaaaaaaa agtgaacttt agaagcttag aatagcggcg agaagacaaa    17040
atcgacgatc gatttcggag atggagaaga agaagaaaat gagttctgat taaggtaaac    17100
ttggagaaaa taaggtattc ccatggatga tgatctctct tctctctctc tctctctctc    17160
aaagtcacag gggtttggca aaagcagctg ctttggtgaa ggaagaagag agagagaaga    17220
agaaattgtg caattactac gaaatgacga gaatatcagg aagttattgg gccttatatg    17280
ggtctttaat gggccttaaa tgaccgtggc cgactaaaaa aaaaagtcaa cgaaaagtca    17340
aatagatctc tgtctttat ttttttgttc tctctcgtct ctctggctac cgagaaaaca     17400
gagaacgtta agaatcattg cttttctcga gaaaataata ttttttaattg aatcgagaaa   17460 ctcttcaaag ttgaattaag aagaatatta cctcaattga gatttgagag acacgcatag    17520
agagattgat tattgcatcg aatcaagctt ggtttgttag taatggcggg aatagcttta    17580
gttttagatc tactgaagaa atctcaatct aagaacactc tccactcatc ttccttctat    17640
tccgcctccg ccgccgctgt ttctgctgcc gcctctgctc cttttgcgtc taggtttctc    17700
ttcgggtatg tattctctct ctctgtagtg gatttggatt tgttttgact ttcactggat    17760
cgtggtggat tgagttattg gattgattac taggtttctg attttgtttc tgattagggt    17820
ttagaaattc agaattgatc atcttctatt gctcaattga ataagaaagg ttgcagattt    17880
atatcagtta ctagtaaaga tcatatttg caatccaatt tgaagtatag tttaattgtg      17940
gtgagattac aattatcgat gaatagtttt agatatggtt tttgatgttc agggcgtttt    18000
gagttttaca agctctgttt ctattctata tagatctctt gataggtttc tgcattcatg    18060 tgtcttttg atactctcgg tgattaccac ttcatagaga actaattggc atgattggtt     18120
gtgctacgac attgactcag attatttatg tttacagttc ttttgagcct agagttgcgt    18180
```

```
attgtgatgc tgctgctgca atagatgatg attaccttgg tgctatacgg aaaatgtctg    18240
cggatgtttt gcagcgtcaa ccccttgcgt atatttctag gtccaaggaa tacaatatcc    18300
agccaaaacc agttctctcg gcctttgagt tcagggcact tgcaatgact acagtgagat    18360
cccttttgat gttttatttg cctcttttgg agcctaaaac ggcttcagag gatgatgatg    18420
atttcctaaa caatgctgca gaagaaaacc gccacacaga cttgattgtt cctcttaaaa    18480
agtcagcaaa gcaaattgcc cgtgaggtta gtatgcattt aaggttctta ccatctgtag    18540
ttgcttcatg atgtcatggt ttaaactgct aatttcggtg ttatgatcca gaccacagtt    18600
gtgaccactc ggagagtcct tgaaaggctg gctctgagtt atgtctcaca gcgtatggca    18660
tggaaacttc taaagggtaa catcatcttc cattactttt gcttccacaa caaacttgcg    18720
ttgtaaaaaa agttagtaga catatttagc tcgatgaact aatagagcgg agaacataaa    18780
tatattatgc agatgtgcct cagtcggctt tacgcaaggc tcagagaggg ttgccgacac    18840
atgtatatat ctttaaagtc agccaaacaa ctcttagagg tataataaaa cattttggtt    18900
tctctactct tcgtgaccct cccatcaaat gctccttctt tttccagatc agacattgtt    18960
tagttctcct gaagcctata tgcatgttct gtctttggct gtgtttatgc aggtcacttc    19020
ctgggaatcg cagcatcatg ggtagttcaa gtaggcattg aaatctacag atgtgtgttc    19080
ccgaatgtta aacccgagga agaagaagaa gaggagaaag tcgagatatc acagcaagct    19140
aaggatctcg gaaacaaagt tgtgggtatc acagtacgat gtggcgcgtc cttagtatt    19200 gctgccattg gagccgggat atgttcttgc cttatccgtc cctccacggg ccaatggatc    19260
ggtaagctca cctcacccat tattggaact ttacagatag aactcgatag aattttaact    19320
ttttggacca ttgattgatg tgtattgttt gttctctatg taggttgcgc gctgggagac    19380
ttggctggtc cgatggttgt ttcggtttgc ctgcagaaga ctcttcaagc tgattattaa    19440
gttcttgtgt ggaaattgaa ttcttctact tgaatcttga tgatccaaat gaaatcatag    19500
agcttgtttt ttgtttctga aatttcttat tgtcttcact gaaccttaaa aacaatgatc    19560
aatagatttc tcaaaatgta cctacttttg acaacagcac aataagtcag gtatttattt    19620
tcctcggatt ttagttttgt atctgcgatt tttcttctct ttttactttt gtaagtaggg    19680
attttgtgaa ctatcctctt atgcaaacgt gaaaagaat gcttggaaga aaattagta    19740 tttgaagtat ggttcagcta aaccaaaagc ctagcttggg attcgagatg attgggaatg    19800
gagaactagt ttgtttggtt tagggttcgg gtcaactaaa gattcccata ccggatttaa    19860
tttgaacttc ttttggactg caattaggct tattttgggt tcgggtcag ttttggattt    19920 ggccatttgg gttagtttat aggcctcaag tctccaagtc caactagaca aaactcgaaa    19980
atcgatattg tgaagtgctc ttttatcttt cactcttcac acaagcatgc attaagtgaa    20040
tcaaccaagc atgcattagt tttggtgtct aaatctctca ggcccttatt aatacctacc    20100
tatgatcttt ctcaaatctt tggtacaatc tcactcattt ttttatcaac cgaatatacc    20160 taaaatctc taaaaacgat gatcattgct gatttgctaa agagggaga gatattttca    20220 attgttaatg tatagactag agactttaaa gggagacaca tcatcactac caccacacaa    20280
acacgaaact catatgaatg gctccaaata agaagattgt cttagttaga aaatggactt    20340
ccctctttaa tataaatatt aaatactttc acctactttc tccttgcaca ccaagccaca    20400
actgttttat acttgtcccc acctaagata atgaatgcat gaatgcatgg ttttcaacac    20460
cctgaaaaag taaccggta aaattcatcg tgggagtcaa aattggtaga gtttaacatg    20520
cttattatta atttgcacac ccatttctgt tgtatgagtg taatccacac acaaaaaaat    20580
```

```
tgtttagcaa attgttacac aaaacagagc ttaggtaata agaaaattag caaattgtta    20640
cagaaaatat attctcctaa gttgtctagc ctctagtatc ccgataccat acaatccaca    20700
aaacagagga tggaataaag tgagagagga aggaacagaa caatacataa gaaataaaaa    20760
gcaacataaa agattgggtg ttcttgttag ttaattagaa gaatgttaaa ttgtcattat    20820
aaaatatttt ttaaagaatg ttaaatttct agaaaactta tctttgtggg atgaagagaa    20880
tattattttc ttttaaaaaa agttttgtat tgttaaatct aaacatatac atcaaacttt    20940
aaaaatcaaa gcaaaaaaag aatatctctc cttttgcatg cttttgacat attgaattta    21000
ataggtaatt ttcttaatta agatgttaaa cttatggatt catgatttga acaaaactga    21060
aaaaagtata tggaagcgtt ggtgagattc atacctatca aaatgaacaa aaggatcacc    21120
aaccgaatag taaaaccaac tactgtattt atcatggcca ttttcttct tctttcttaa    21180 tttctctctt tattaaaaat ttgttaatta tatcataatc ttaactgttt tatataaaaa    21240 gtgtttttc ctagaatata caaggtattc cgcaaaaaat gccaataaaa atggttttaa    21300
attaaaaaga aagaccaaaa ctcatataac ctcaaaaaca tagtatgtta ttttagtta    21360 atataaatat taaatacttt cacctacttt ctccttgcac accacaactg ttttatactt    21420
gtccccacct aagataatga gtgcatgaat gcatgaacca tcattggccg atgcgtttcc    21480
tggtgcatgt agctcacagc cgtcgttctc acattttgtt atttatgatc atactttttt    21540
ttcattaaaa ggaaaaaggt ttactggttt ggtttagaac aagaactact cgttataatc    21600
atacttttgt ttaattaaaa aaacaaaaac aaataaattc tagtacatct tatattacat    21660
actatagttt gatgataaaa ataaaattca aatgacgatt atcatgtcga aaagacaaat    21720
aataattgtc ttactgacct acctgcctgc ctctatatat atactagtct ttggtcgcct    21780
ttactataac caaacatcga gcttgcctta gagtttgtct caagcttctc cttttttggt    21840
attttgtctt aagcttcctt gcttctcttt cttcttcttc tctactcttt ctctctattt    21900
caaaccttcg ttttctttcc ttttttgtat aaaatcttaa aatcaaccaa gacaatggaa    21960
atgaaattgc tctttacatc ggctttcacc caaatgttcg gctactcgaa ccatatggat    22020
caagccagca actgccaaag cacccgcaac aaaattataa agatgatgaa gaaagaagaa    22080
ttcccaagtg gattccaagt ccctcttcac taccctaaat actccaagtc tgattacgaa    22140
gttatggatg atctccgcct tgacttgctc ctcaaacaat atggattctc ctttgaagga    22200
tctcttgaag acaagagggt ttttgcaatt gaatcatttc tctggcctga tcagctttag    22260
atggtctatg ttggtgttga atgatcttat atcgctctcc acatgcatat caatgagcct    22320
atactcgagt ggttgaatgt ttttaaaatt atgtcaaatt accatgtata tcaatcactt    22380
agtaatgttt tagaactatg tcaaatacta gtgtgtgtta tatttctttg tgtgtgggga    22440
tgttttgaag tatgcaattc ttcacatata tatgtatcat atgagtgcat taataacatc    22500
tttgatgtca tgtataacac taaaaaaatg tgatttatcg acttataaaa atcttaacat    22560
attgacatta acataaaaca tatagattat tgtatgatat agattaaaca tgacgtcatg    22620
ctggatattt tggcttattg gcttgtacat tacttgtgat tatgagtgta taatataaaa    22680
ctaattacta gatttgcaca aaaaaaaaac agaaggatag aaaactaact agaaaattaa    22740
gacattacat acattcttct atatgaaaaa aaacatttaa aaaacaaaac aaaacatttt    22800
tatactaaga tactaatgaa aaatcctatc aagaaaatga agaagatcat aaaaacaaaa    22860
ttatcggatt tgaagagaat aaaattttgac caaaaaaaaa gaagataatt aaaataaaat    22920
```

```
aaaaacaaga attggccaac tgtgagaaca tcatcaatga agaccaattg cgagatccga     22980
caacaccgct tcttttgatt tcgatcttac tttcctgggt atgtctcaat tcttcttcct     23040
ccttcagttc gtgttctgtg tctgattgat tactctcaca aaactcatct tttcattgtc     23100
taaaggtcta atctttagct ataactcaaa atctgtatct aagttctgac aagtttctgt     23160
tacgaaattc aaattttttg atacatatgt tcatttctca gaacaggaga tgtcaatttt     23220
ggcgatggtt ttcgtaacat aaacatgaga tttgattgtt ctgtgcagat ctcatagtta     23280
atctggtttg agtctagaaa tgtcgagtga tgcagctcgt acgccattgt tacccactga     23340
gaagatagat accatggctc aagatttcaa cctgaactca agaacttctt cttcaagaaa     23400
acgaagattg cgtcgctcta gaagtgctcc tcgtggtgat tgtatgtaca atgatgatgt     23460
caaaatcgac gaaccacctc ctcatccgag taaaatccca atgttcagtg atctaaaccc     23520
gaatctcagg cgagtgatca tgttcttggc tttatatctt accattggta cgctctgttt     23580
ctacctcgtg agagaccaga tctccggtca taaaaccagt ggtgtggtag atgctctcta     23640
tttctgtata gtaacgatga caactgttgg atacggtgac cttgtcccta atagttccgc     23700
ctcaaggcta cttgcttgtg ccttcgtctt ctcgggaatg gtcctcgttg gtcacctctt     23760
aagtcgagcg gcggattatc tagtggagaa acaagaggct ttgctcgtta gggcttttcca    23820 tttgcgtcaa agctttggtc caacagacat tctcaaggag ttgcatacta acaagttgag     23880
atacaaatgc tatgctacat gccttgtcct tgtagtcctc ttcattgttg gcacgatttt     23940
ccttgtaatg gttgagaaaa tgccggttat ctcagctttc tactgcgtct gctccacggt     24000
tacaacattg ggttatggag ataagagctt taactcggaa gccggacgcc tttttgctgt     24060
gttttggatc ttgacgagca gcatatgttt ggctcagttt ttccttatg tagctgagct     24120 aaatacagaa aacaaacaga gggcgttggt gaaatgggtt ttaacgcgaa gaatcacaaa     24180
caatgatctc gaagcagctg atctcgatga agatggagtt gttgggtaag aaagacatca     24240
gacatattct atcttctgtt tccttcttcc tcttcttatt cttttttttt tgtctattgt     24300
gtgttgcaga gctgcagagt ttattgtgta taaactgaaa gaaatgggta agattgatga     24360
gaaagatatt tctgggataa tggatgagtt cgagcaactt gattacgatg aatcaggaac     24420
tctcacgact tctgacatcg ttttagctca gaccacgtct cagattcaaa ggtaagcctc     24480
atcatcatca tcatcttgcg aagacgaatc agaatctttg tttagttata ccttcacaca     24540
acaaaaagcc gaagagagtg aacagttttt cgaaattttg tttgttttt cctgtttgtg     24600 tttgtaatgt aatgccacac tctaactctt tgatcgtttc ttgatgctga gtgtataatt     24660
ttacatacat ctatacatat gaagctctct agtgttatgc tccatgacca agaattcatg     24720
gatgattctc tcaaaggaca gggtatgaag actgttttat tgctttaaac ttttttggta     24780
ttttgattga tacaaaacat tttcaaaaga tagcggtttc tcgcgttatg gaagtcgtcg     24840
tttctcgaac tgagattcat ggcaatgagg gtcaagccag tctcttgaaa cacctttttcc    24900 catattagtt cctttctctg cacctgcacc cccgcctaca agctctctta agttagccat     24960
tttgttttct cgaccagagc cgctcatttt ctgatctgct tccttgagca tctgcttaaa     25020
ccgctgcttg cggctcgatg tgttactacc accatcttgt agctgcgaag gaggagctcc     25080
atgtggtcct aagtagatgt tttcttcagc tttactctac aaaatcatac aatgagagat     25140
aaagagttaa caacattttt ttgaaacttg tcttgtacgt aagaaatcaa tcactaacct     25200
taggagaaga aggttttgat gtttcaactt ctgaatcatt attattatta accttgtctt     25260
cttcaatctc caagctcgga atcacaaacc catcagtgtc tgccaccaat caaatgatcg     25320
```

```
actcaagatt tgtaattaca caagaagata cagaaatttg aatgattgaa tccgatcaca   25380
taaacacgaa agaaccctaa tttcaataaa gaaatgcaac tgaatcgatt aaagcgaaat   25440
tacttacccc attcatcatt gtcttctacc ttgggaagat tcgtctgcat tacagatgta   25500
tccattgaag actaacgttc atggacactc tccgaaggac caacagttta caaaaaataa   25560
tttctcagct ctttggcttt tgaatgtgaa tttatgtatc aattttacaa taattcgatt   25620 attttttcacc tgattgattt ttcgcgaaac cctaaatgtt agagcttggg aaaaggggga   25680
aacagataaa taatgatggt gttgaggcga atcggatcgg atccggattc gattgtttgc   25740
gattgacacg gcggagaagg agatgttagg gatactttg  taatctacta tcgatggtcg   25800
gtattcagcc acgtgtcagc tactcattcg tgaaactcct agacgaaaat gttgcgttgt   25860
gctttgtgaa acaaaactag tactatgtgt ttggttttt  gtttatatta gggaaattgc   25920
actctatata catataaaat tataaaatta agtattagaa aaaactactc tcgaatcttt   25980
tctctctatc atgaaaatac ccttatatct ctataccata tttgcttttg acgttaaata   26040
ttttgttacc ttttaataat aatgttatca tcttcccata attatataat ctttaaaatc   26100
aaatcgttgg ttcaatagct ggtaatttgt ttatatcgtc aattgtatta ttaacatgtt   26160
aagtaggttt gtaccctaag tttttcatc  catatatcaa aatcctatcc atattttgct   26220
aacaatatta tcccgataat acgttatcta ttaactattc tgatgcacgt atttttcta   26280 catgattatt cagtcgcaag tcaacttta  tggtattcat gttaaatatt ttattatctt   26340
ttaataataa tgttatcgtc ttcgcatata tatgtctttg aaatctaaac attggtttaa   26400
taactgaaaa tttgcttata tcgtcaaata tattattaac atattaagtt ggtttgtaca   26460
ccatgtcatt tcatccatac atcaaacccc atccatattt cgctaacaat attatctcga   26520
taatgcgtta tctgctaatt atcagagttt taccatatca ctttgtaggg gtatatttgt   26580
catatagatt ttaattgaaa agagatacct aaataaatgg tattcatgta cagattctta   26640
attatttgat ggtccatgta tagatttta  aatcacccct tatattattg ctttgtcttt   26700
tttttttttt gtgaacatta ttgctttgtc tctatatctt tcatattttc acaaatgcag   26760
tatgccatat cattttgtag ttacaagagt gtagagttac tatgactatg aaaaacaatt   26820
aagtaaaatt tgcttattat aacttttaag atataagaaa tcaaattact ttttcaagga   26880
agcacaaagc ataataacga aatcgttgga tccaatccaa caacactcgt atcggatttt   26940 ttttttggata tttaccacaa cagctaacag tagtaaaagt tgtatctcca aatgaaagca   27000
cactattaat atttcaagat tatcgaaatt tgagtatcaa acaatttaac cgccaactct   27060
tgttctttta ttaaaacaat ttttcagttc atcgctatca acgtttcaca atcttacgat   27120
ttaataacat catttcttag ataatttctt ttgttagtat tatatgatat catatcatat   27180
catatcatat cattgatatc atatcattaa ccatctcatg attaccattg aaaacaaatg   27240
gagtcttttg tgagacaaag gtaggttcct aaaggataaa gtgacaattc cctaaatttc   27300
tttaaacaat cagaggaaga aataatgatc acttcagttg agaatatttt caataaatca   27360
gatcgacaat cctagttgac aaccaaaaaa ataaacgaca aacttatgaa gggggtaact   27420
tctagagaaa gattaaacta gtacaacttt acaagtagtt ttcaaccaaa gcttaatgat   27480
actaatattt ccttaacaaa aacaagcatc cttaattagt gggcttcaca tggatttacc   27540
aaattccaaa gcttttttata gattttttcaa agtgttttat tttttcaaat acgtacatgc   27600
aaaaaccaat gcttttcctt ttctcgaaaa aatttagttg caggtgtaat tatgtaagtg   27660
```

-continued

```
tgagaaaaca aataaagctt tcttgtttgg ttcctctgac ttcctctgat ttctctctct   27720
ctctttctca gacttgtctc aaactttca agaactcaga ttcgtctctt ttcaatctct    27780
cttcttaaat caagatccaa acatcgaaac tttggtttaa agatttgaat aagtcataac   27840
tcaaagatcc attaacatca atggataacg acacaatctc gacttctctt tataactagc   27900
tctgtctttg ttttttgcttt gaattaaata agtttctat aatggtggaa aaatctgatg   27960
atgaaaagca ttttactcgg tgttgctttc tttcacagct gtcactgctg ttttttcttg   28020
taaccctaat ttcatctgta gctttcctct gtttcttgaa ctctcaagga gtctcctctc   28080
tcacaataac catggcaatc ttgttcgtct cctcttctgt tttcttgtta cgaatcttca   28140
aggaaaagac aagactatgt ttggctgagg ggtcccaagg agaaggctac gattatgaag   28200
atgatgatga tgatgatggt ctcattgaga ttgatcttgt gagcgaagaa gcagagacta   28260
tagaggcaat gagaaacatt aatcaaagtc gactgagaat taggattgaa gaagaacaag   28320
aagaagatat tgatgatgtg aatatggaag aagataatct tattgagatt gatatttcca   28380
ttggatccat taaaagacga atgtaattta gtttaataga tctcatgatc acaccatcgt   28440
gtaatccgat ttttcattt caaatgtaca aaggaaatcc aacattttaa tatattattg    28500
ttctagatat ttggtgatta gggtttaggg ttttaggaga tatatatcaa tccctttta   28560
tagatgcata tatatatata tatatatata tatatatata tatagtacta attaactgtg   28620
gtagttcttt tgcattaaga ttgtgtaata gattgttgac aaaagacaaa agattgtgta   28680
atagattcct gaaaggtttt gtaaaacaaa acaaaagagt tgcaattct tcgaaagtac    28740
tctccgagca taccccaaac tccgctaact tattttctat gccaaaacac ttgtctttct   28800
cttattgcag agtataatttt tcttcttctt cactatatca tttaaacata aacttctttt    28860
ttaccaaatt tttggttatt gaaaaacact tttccttaa ctttacgaat caatatacaa     28920
gcataactta taatcatcca ccacactaat catcatgcac tttgttaatt gttatggctt    28980
atgagtctta tgacttaaca tccttttta tctggtaaat ctagcaaata ggaatcctct    29040
gcaatctgaa tcttgtttcg aaatttgaga gtatgttgat cttgcgaaaa tcgaaacaat   29100
ctttgcaatg taagaagata tgaagccgca tatgactaac aagaaagttg gtctttatgt   29160
cgtctaaatc agaatataag agcatctcca ttgcctatga aactcaggag agttttagaa   29220
aactcaaata ttaatattta atttaaaaat attggaccat gaaatatgta agcggaagag   29280
ccacaaaaca actattattt tgttttttgtt cttttttag ctaaataagt aataaaatat    29340
tcaaaataaa aagaaggaaa aaatgaaaat aaagaaagga aattcaacat ttctatatag   29400
aattagttat taccattaag ttaaatctaa aaaagaaaga atcttatcc ttttaaaaaa    29460
tagtcaatac caaaattaat ttcattatca aaatgtaata cacttattat atatggaaca   29520
aaattgtcaa atacaataag gttaaaatct actttacagt attgataaat gataatcaat   29580
catgacttta ttgagatatc aaatttaacc ttatcatcaa aacataaaac atagtatagt   29640
atatatgaga aaactatac aactagaaat tatacgtaga aaaatcgtt aaacacccgc     29700
taaaaatcat actataaaac acaatagtat acatagaaaa accgttaaac acccgccaag   29760
tttagtaaaa aaaccgttaa acacccgcaa aaaattagta agtatacaaa tttattttat   29820
atgatcacaa tattatacgt agaaaaaacc gttaaacacc cgccaaatct aatactacta   29880
aatatcgatc ataacttcat taaatgaaaa aaaaactcaa acataatatt aagatctaca   29940
taacttcatt aaaatgatta aagatctaat tatttttcat tttttggggc aaatatttag   30000
atcttctaat ctaataggga atgaactcaa agaaagatat ttgtgtttga agataagtaa   30060
```

-continued

```
actgtaccgg aagttgggtt gtgtctaccg tcaccgatcc acgagagtat cgaacacgaa    30120
atctgaaccg ttcacaggtc cgacgtggca ataaactgta tttaaaatcc ggttttgagt    30180
ctgaatcctt aatagaaaga gatcggagcg ttggtatccc ttttttcttc tctgattcga    30240
acagaataaa taagaacccc aaaaaaaaaa aaagctcact gctttgaagc ctttggatag    30300
cgaaggtgag attccaaagt cttctccttt cgagtctctt tgtacactct gagcttgttc    30360
tctttgttta gcggttgaat cttcatagct tcgtttatat tcgcatgtgg tttttttttt    30420
ttttggtttt gattgttgtc ttgcttcttg aagtcgcgtt tagggtttgt gttttttttgt   30480 gttctctttg atttgtgaat ttgtgttagt ttagtttagg tttagagaga gactaattttt  30540 gatttctgta tgagctcttg gattcctctg tgttgtggt ttggatctaa atctatgttt     30600
tataccacaa agtattcaga ttgaggaaaa ttttggttac ccttcgtttt tgatttggaa    30660
ttgaattatg aagaacttat tgtatgttgt ctatttcctt taaaaattga atcttttttc    30720
tcaatttctc gtgttagagc ccattgaagt ttttattgag ttgtatgtag aaagatggga    30780
tgcaatgaag tttacatgtt gataaagtt ttgggttatg taacccttct tttgcgtgac     30840
ttttgtttca tgaaatttct gccgctattg tgtaagtttt taacactgta cttatatttt    30900
ctacagcgtt ctggtgtttt ctggctttaa gatctactga acattgggtg tgagcaatgg    30960
gggaagaaga tacaaaagtc attgtggagc caacggcaaa tgggactagc tctcttcaaa    31020
agacatcaga tgcaatcagt ggaaaggaag tgcaggagaa tgctagtggc aaggaagtgc    31080
aggagagtaa gaaagaagag gatactggac tcgagaaaat ggagatagat gatgagggta    31140
agcaacatga aggagaaagt gagacaggag ataaagaggt ggaggttaca gaagaagaaa    31200
agaaagatgt cggtgaagac aaggaacaac cagaagctga taaaatggat gaagacacag    31260
atgacaagaa cttgaaagct gatgatggtg tttctggcgt tgctactgag gaagatgctg    31320
taatgaagga aagtgtggag tctgctgaca ataaagatgc cgaaaatcca gaaggagagc    31380
aagagaaaga atcaaaggag gagaaactgg aaggagggaa agcaaatgga acgaagaag    31440 gggatacgga agagaagttg gttggtggag acaaaggga cgatgttgat gaggctgaaa    31500
aggtagagaa tgtggatgaa gatgacaaag aagaggcact gaaggagaag aatgaggccg    31560
aactggctga agaggaggaa acaaataaag gagaggaagt gaaggaagca acaaagaag    31620 atgatgtgga ggcagacact aaggtcgctg agccagaagt ggaagacaaa aaacggaga    31680 gtaaggacga gaatgaagat aaagaagaag agaaggaaga tgagaaagaa gagagtatgg    31740
atgataagga agatgaaaag gaagagagca atgatgatga taaggaagat gaaaaagaag    31800
agagcaatga tgataaggaa gacaaaaag aagatatcaa gaagtctaac aagcgaggga    31860 aaggggaagac tgagaagact cgcgggaaga caaagagtga tgaagaaaag aaggatatag    31920
aacctaagac tcctttttc tctgatcgcc ctgtccgtga gcgaaagtct gttgaaaggc    31980
ttgttgcggt ggttgataaa gattcttcaa gggaattcca tgttgaaaag gtttgccaat    32040
agtttacttt gtttggttta tatatagtgt ttcacggtta gatctattag taatttgctt    32100
ttgataatac agggaaaagg gacacctctc aaagatattc ccaatggtat gttcatattc    32160
tacatattat ccttagtccc tctcatcctt aattagtcgt tttgttgaac cgtctttttg    32220
gctttagttt tcttaggact tactcgagct catagtcgtt tctattactg gatggctctt    32280
tgtgactttg taggcttgat tttcttttct ctatatttta tttgtttctg gctttgtcaa    32340 tctttttat gttagatgtt ttcctttga tttagtgact agagcctggt ttaaaatgca      32400
```

```
agaattccca tggctttgaa gttaattgtc atgattacat tctctaaata cttcattggt   32460
cccatctact caatagttta tctgctcttt aaatgaaatt aataacgtgt atttatctct   32520
gcagttgctt acaaggtatc aaggaagaag tctgatgaag ttttcaagca gttacacaca   32580
attctattcg gtgggaagag agtaaaagtg agtatctctt tgtgcccttt tccattttag   32640
cttctccatt agacaatttg gtaaactgtc aatctcatgc atgttcttgt gggggttcc    32700 aatgaagttt gaagttctta ggactgcatt gtggtatcgt taagattata gagaatctgc   32760
taatcatatt catatgtgac tcgattttct tactttgaca ggctactcag ctcaaggcac   32820
acatattacg cttttctggt tacaaatggc aaggagatga ggtgggcgag acaacacatt   32880
aaaattttat aaccaggctc atctcatatt tcttacataa ttttcttcaa tgatatttga   32940
caggaaaagg caaattgaa agtcaaagaa agtttgaga aaatcaacaa agaaaaattg     33000
ctggagtttt gcgatttatt tgacatatca gttgctaagg ctaccacaaa gaaggttatt   33060
aaggctactt atttctaagt tccgttgttt ggagtttctt ttactgtaat caacttggca   33120
actgactgga tggtactttt cctccaatat aggaagatat tgtgacaaag ctggttgagt   33180
ttttggagaa acctcatgca acaactgatg ttctagtcaa tgagaaagag aaggtaagtt   33240
tggtgctgga aaggccttct gttcagcaat taagcctgaa aatttattgt gcatattaca   33300
actttctatt ttttctattg aatagggagt gaagcgcaaa agaactccta agaaaagttc   33360
acctgcagct ggaagttcat cttcaaaacg atcagcaaag gtattactca atagcttaga   33420
actggaggtt taaatccttg tgctagaaat ttcgtctttg tgtctggtcc aagtacctga   33480
attctgattc gtttctttgg gttctttaca gagccaaaaa aagaccgagg aagcaacaag   33540
gactaacaaa aagagtgtag ctcattctga tgatgagtct gaggaagaga aagaggacga   33600
cgaagaagaa gagaaagagc aggaggttga ggaggaagag gaggagaatg aaaatgggat   33660
tcctgataaa tctgaggacg aggctcctca gctttctgaa agtgaggaga atgttgaatc   33720
cgaggaggag tcagaggaag aaactaaaaa gaagaaacgt ggttctagga catcatctga   33780
taagaaagaa tcagcaggga aatccagaag caagaaaact gcagtcccta cgaaatccag   33840
tccaccaaag aaagctactc aaaagcgctc agcaggtaaa cggaagaaga gtgatgacga   33900
cagtgataca agtccaaagg catcttctaa gaggaagaag actgaaaaac cggccaagga   33960
gcaggccgca gcccctttaa aatctgtatc aaaagaaaag ccaggtttgg tcataccatt   34020
cctttccaaa aaatctttca tttaagaatg aagtatatat gagtacatgc tttgtcagaa   34080
gcttgagcaa tcttaacctt tgatcttata ctgcagaagt ttatccaata ttgcagccat   34140
tttttctttc tttttctga cactatgttt accctgtgtt tgttattctt gtttagtaa    34200 taggaaagag aggcggaaaa gggaaagaca aaaacaagga gcctagcgat gaagaattga   34260
aaactgcaat tattgatatc ttgaaagggg tggacttcaa cacggtgagg atttgaacca   34320
tgaacatctg tgtcattaaa ttacagtaaa tgagcacaga agatagatat ctaacaaatg   34380
ctttatcatt ttctgacagg ccactttcac tgacatcctc aagcgactag gtacagagga   34440
gatattttcc tagcagttat tttcttgttt gatggtcttt gcattggttt ctgtttttgtt  34500 tgattaacag atgcattgtt tttgcccgtc tttcagatgc taagttcaac atcagtctcg   34560
cctcaaaaaa atcatctata aagcggatga tccaagatga gctaactaag ctagcagatg   34620
aagccgagga tgaggaagga gaagaagagg atgctgagca tgaggaagaa gaagagaaag   34680
agaaagctaa aggatcgggt ggtggagagg aggttaaagc ttaatcacaa aggacatgaa   34740
tctagttgac ttactagcta atcgtcaagg gtgcctcctc gattgcctag ccttggtcat   34800
```

-continued

```
taggcaaata tatcagagaa tgtaatttgt tggttgttta gtctggaatt gtactacaag    34860
cagatatatt ttttttttcta aaaaaacttt tggagtcgga gggaggacga cgctgagaag    34920
tagtagtttt aagataagca gctttgtttg tgtataccat ttaacataag ctcctttagg    34980
attcatgccc aacttgaaca ccctttttgat tttttgggttt ttattagttt ctctcatgca    35040
atttcgtttc tgtactatat tactttgccc gttttgtttt ggtcaagttt gtatgatgcc    35100
gacactaatg atactgacaa tcaagaccat gcagagaaag aagagagaca caagaaaata    35160
attcatatcg acctattcaa acaaaagaaa cctattctac tgaataaagc aatgtctaac    35220
cagcagggca gaacaaggaa gaatcaactt ggccagtgct aatgaagaat aaaggatcta    35280
tgccattgat gtggatgtgt tcatagctac agaaacttaa agaaaatcca tgaaaatgaa    35340
gaaatgtaac ttctattatg tacacacttg aacaaggagc gaccagattt cctttttcaac    35400 aaaaaaaaaa aatgatctac tacatcactt ttggaaatca caaaaacaca atcccaaagg    35460
atgctcatgc tgttacattt gtcatgtctc atgacctctg aagttcctaa ggcagatgag    35520
gagcttacaa tatgatagat acatacaata cagcccaaat ggctaaaact tggagaaaca    35580
agatcagtaa cactggccag gctaactatt tggctgcaac taatacaact acacaacaac    35640
aaattcagaa acagttaaaa caagaacatc taaacacaaa tggatggaaa cccaaaaggc    35700
caaaacatca ccacaacaca ctggtcttta gaagtttcac ataaaaaatg gcaaaaggaa    35760
aggtgtctaa taacttaaag aaggtaaacg tttgccaagt ttctttccac ttctaggtaa    35820
ctaagctgag ttgaagaaga gatttcacca gtaagagtct tcaatctttg acaagagtct    35880
gcctttctat cttcttcctc atcttgctct tcttccataa gggggtttat agttttgcag    35940
taactctcaa agtcaatcta cccataatgt tatgaattta agaagacaac agaaaccata    36000
gtcagtaaag aaaagggcaa aagtataaac cacaatgata actatcaact cgaaaaatca    36060
ttgagctaca agagtataca caagttagac aatatgccct tgcagacggc taaatttttga    36120 tcagaaaaac gaaccaggcc agtaactagt caaagtctta aagcaaaaaa atcaaaaaga    36180
atggtagaat ttacaataca taaggaacaa aagttaccat cagattcaac tacttacttt    36240
tatctgatac tcattcagta gtaagccgcc ttcttttccc ataatcagta tcccttgatt    36300
ttgagcgatg gttatcctcg cgagacaacc gcgatttgtt gtgtcctctg gatgatcggc    36360
ctctgttcca ttcctcatca tgttcaggtt cgtccctgtg tctagtacga tgatcaccac    36420
catatcgttc tcgttcttct ctatgacgat ccctctccct ttcccttttct ctgtcacgaa    36480 catgttctct ggagcgttca cgatccttat gatgatgttc cctctcacgc tcacgaccgg    36540
tgtctctatc atcacgatgc cttctctctg gcatatcata accgtgacca acatctttct    36600
ccctcggtat gtccctttca taaccagcat ctttatcctc acgattcctt ctatcagatg    36660
aaccagacca ttcccttttct gaagctcttt cttttttcctt cacaggattt ggacgagccc    36720
ctctttcgtg attaacctct ccatactgat gatcagatgc agcttcctcc ccataactcg    36780
attccgcagc tcttccacta cccagatctt caccagcacc ccaccctcca ctgttaggat    36840
cccacattcc catattatgc cctccatcaa caccagcatt aggcatcatt cccattccat    36900
tcatcggcat ccctcgtcca aaaaatgctg gattcacatg aggtgccact ccaggtaaac    36960
caactcctcc tacaggaggg aatgatgaca aaagcccagg aaactgtgga cctggagccc    37020
cagggaatcc tccatacccct cccattctcg ccatcggtcc accaaaagct tgttcaaacc    37080
cttgccccat cattggttga tgcatcatat tcataggagg ccctgtaccc attccttgac    37140
```

```
caaacccacc attacccatc aaacctcttc cacccatccc attaggccta ttcctcattg    37200
gaccacctgg tcctctacca cccattcctt gagcattgcc tctaccccaa ttacctctac    37260
caaatcctct atttccccca ccttggaaat tcccgccaat ggcgttgttg ttgttgttat    37320
tgttgttgtt ggccacgagt ggtttacttg gaggatcagc aggccctcct ctcttagctt    37380
gtgcaattac agattgagcc tgttgggtcc tattcacctg tgcctctccc attctcttaa    37440
ccgaatatgg ggacgcatac tcaacaacac aaggcctacc gttgaatgga tacccattca    37500
gcgcatcttt gcaagccgaa gctgccacag gatcatagaa ctctacttga caataccctt    37560
tcgacttccc actagctttc tcatcaaaga acttaacctc cttcactgca ccatacttgc    37620
acaactctgc ctcaagctcc gcatcagttg tccaccaatg cagatcccct acgaaaagaa    37680
aagctccacc gcctcctcca ccaccagttc ccccgccaac aacaccaggc atagcgatat    37740
tagctccgtt cccaaccatg ttactaccag gtccaggagg aatcccgcca ttaacattac    37800
ccatcacagg tctcatcaaa ttctcgttat tccccaacac aggcggtggt ggcaagagac    37860
cctgcgaaat attattccct ctaggtgcct cgagatcatt agcccgatta aagcttgcc     37920 ctagctcaac tctcagccca cctccagtac cagtaccaat tccaccagga atctcctggc    37980
taacatcgct taccttaacc tcctgagctc catatccact agaagcgacc accacatcag    38040
taccacttcc acttcctcct cctcctgact ctgcttctgc ttctttctca acgctctcac    38100
caaccaaacc aggtatcgaa atcgaaacct cagcttcacc taaaactggt tcaaccctat    38160
cttcctcctc catattaacc ttctcctttt cctcgtttct agatcccgct tcgtcgttct    38220
ttttcataga ctgaagaaac ccttctccaa cattaacgtc gttataaaga tcctcataat    38280
catcatcctc ttcctccgcc ataaacccgt cgtcagcaac ggcagatatc gcctcgtttt    38340
gatgaaattg atccatctga tctctcccat ctccctcatc catcttaaaa gactcttcct    38400
tgtgataaaa aaaaagctc ctttctcgaa tcagatttat cacaagctta cgttatcact    38460
cgctcgaaca tgaacaatct caataaaaga agagattttg cagaaatttt gtcaccggag    38520
acaggacctg ttgctagaaa ccctaatccg gtagatttgt gaaatttctt ggattttctt    38580
ttttgatttc tttacaatta aaattatttt tttcctcgat ggaatccaac taatttcact    38640
aacatgcacc gtacacagtc gcgcattgta gagccttttt ctagtgtaga gatgacacgt    38700
gttttccgaa tttacgagaa ctaacaacaa tccaatacgc gtggtttcat gacccagaac    38760
aaatgggctt gcttttaatg ggctcactta tgtgaactac ctgtcgttca aactttcgaa    38820
aacttattaa acgactcgtc gtctgatcat ttctgaataa aacttcctgt cgtctcataa    38880
taaccggttt tagccggtta acggctactt cacttccgac aatacaggcg ccaccaacgg    38940
tcatatatct ctcgattatc acaattcaca acgtttcgtg tttaaaataa ttctctttct    39000
tataataaat ccattaaccg aaacttgcaa atacttattt tactaagaac tgagaatcag    39060
aacactttgg atttttgtta tctttcccag aatcagacaa aacaagaaaa acgatgcgtc    39120
ggtttgctgt aatttacatt tttgtcttct taatttccat ttctggtaat gtaaaagcgg    39180
ccaatgcacc cgctcaatcg ccgagactcg ccgtgaaaca tcatcctccg gcaaaatctc    39240
atcatcttgt tatttctccg ttaaaggctc cgacaaagtc tcctcaaacg cccactttac    39300
atccgccggc aaaatctcat cgtgttattt ctccgtcgaa gtctccttta actcctactt    39360
tacatcctcc ggtgatccaa aaatctccag aggcaccatc ttcgacgaag caaacatcgc    39420
cttcaaagtc tccggagaaa tcctctgttt cctctccggc ggccttttgtg actccatcga    39480 tatcccctgt tctttctccg gcgacttccc catcttggac cactgcatct ccatcgaaat    39540
```

```
cacctgtttt tactccgacg aattcccctg tttcctctcg aaccattgct tctccattga   39600
aatcccctgt ttcgtctccg gcgacttccc ctgttacatc tcgtaccatt gcgtctcctc   39660
tgaaatcccc tgtttcatct ccggtgactt cccctgtttc ctctccgact acatccacga   39720
ctcctgtctc tacgcctgca acttccctg tatcccctcc cactacaatt ccagggaagt   39780
ctccaatctc tgctccaatg ataagtccca ccacctcaat agaatcgcct gccaccaccc   39840
catcaaacca accaccagtc tccgccgatg ctccatatat cgcagcaaca tcgccagtaa   39900
caacccctga tattccatca actccagcga atacgccgga catatttcct tacggacgag   39960
gtccggtgag tagttctgca ccagcgacgg cgaatctggc tccagagact gctgaggttc   40020
ccgccggagc caagtcggct tctaaattcg ttcaacatga tctcctatgc atattttga    40080
tcttagtagc cactttggtt cttccagcta actagctttt tgtcagacta taagaagact   40140
cttcagtata tcttgtaatt ctaatgaaca agatacttac ttgttttgta ttgattactt   40200
tatagtatat taatgttggt agattatatt tgttagtaca atatgttttc gtaaaaacac   40260
cattttctta ttccatgata tagctatgaa aaaaatcaac aaacttaata gaaacttgat   40320
aaaaagaagt ttataaagca acattcaaac ggaagaaaca aatgacattt ctcacataga   40380
aagtttactt gaatcctcca aatcattaac ttgtgcaaac ctgaagggat aatcttggaa   40440
ctgcttcaca ttgttgaaca tactgtttcc taaaccccaa tgtattggct ccatataagc   40500
tgtcctctgt accatcggac catatggacc atccgaacaa ctcccgtaaa acaagctttg   40560
cccgttcgct atcatcggct ctgtcacatt cgagaaggaa gacacttccg cagtatttga   40620
ggtcatctgg ttattaaaag ggaagaaaga gagcccgttg taatccatag taggcagagg   40680
aaacaactga tactgctcaa aacattgccg attgtaaccg cataaccaa gttggtcatt    40740
agaccaacaa ctagtgtcag gaaatgtctg attcctattc gtagcctctt ggatcttgtt   40800
ttctactgcc atgaaaaccg catagaggtc atttaaagaa cactggtcga gcttttgtc    40860
ccatgtagga tactttgtcg caatcgtcgg tttctccacc ttagtgttgt ttttctccaa   40920
gcattcttgc acggtgtatg tcttggtgca gctgcttgac gcagtgtctc tgtacttggt   40980
taagatttca cggactttgc tcccatcctt tggccataac tcgggctcca tgaccatttc   41040
gtcccctgct ctgctcgggc cgtacacaat gacacaagtg tccacaccgc agagtgttga   41100
gaactcactg gctttcttat acaaacatgc tttcctcttc ttgtaagtcg ttatcctcgt   41160
tttctcgttc gttatcctcg tcatctttac catctttcga cccatccaga tacctttgct   41220
tcaatctaaa aagccataaa agagtaaaac acaacaatag atcataatct tgaaaattga   41280
aatagtaata tcatcatttg gatgtaacga tcagctacca aaacatacag aaacactaca   41340
aatttacaac caaagcacta atactagtaa acattttgtt gtcaataaaa aatttgtaac   41400
tcatatagct tttaggttta cattttaaca tttcatagca atgtaagcct tacaaatgta   41460
tagggaagaa agattcatat tatttattc tcaatttttt cactaataag cataatcctt    41520
atcgttttgt caagcttcct atgcataatt ccaaatccat atacgattaa cacgaatagt   41580
aaaacagatg ggatattaac ataaagtaaa tgcagagtga ttactagaag aaaaaaagaa   41640
tgtatataat accttcttta agagctctac tttctgaagt ttcttgattt aacaatggag   41700
ttcctctttc tgtgtttata taagacacac gcaaaaaag aatatatgtt tttttttttt    41760
tttttttgtcg taaagaatat atggtttatt ctcgaatatt gtttcctccc ctaaattacg   41820
gtagcaatgc tgatatttta tttctttcca tgttttcgag tagaattaaa gaggacgaag   41880
```

```
ctatacaaat ctttagtttc tatgttcacg cacaagtgat aagagttcag ttaaaggaaa    41940
acattgtaat tacagcatga tcaagaaaga agattttgtt tgtgatttgt gccaattaat    42000
tttctcaaat attccttttt tgctttaatt gaaaactttg ttaatattct tacggaaatt    42060
tggcgccgga ggtggctgag gttccgtttg caagttgcaa caatgttctt attggtcttc    42120
atggccactt tggtagtttg gttgtataga aattagaaaa aagattaaag tttgttgtcg    42180
taagtttgtc acacttctgt gatgactatt tgtactgata ctcgatagtt cattttaata    42240
taatactagg agacatcgac aaataataaa tttgtttcat aaaattttaa actactagta    42300
gctgttggtg ttgatcgatt gatcggtaat tcatagcctt tgaaatatac atttaacaat    42360
ttcaccaatc accatatgct catacgcact ggtatgtaac taaaaatga ctagaacttg    42420 taaaatgtcc catgcaatta ttacttagtg cgtatttga attttgttt ttttatcctt     42480 tattatcttt cacattcgaa taaatatcag ctatatgtga taaacaaagt tttgccactt    42540
gatgagtagt actacgagac tgaaacgtga catatcgtgg acccatgatt taatttgatc    42600
aaactatatg acaatgaaga cggaaataat aggttaactt aaatatgtga gacattttc     42660 gtatactatt tatatgccaa attcactact ataattggta ataggcagtg ttgatggtgg    42720
cgagtagcat gggatatgtt ctaatgggat attttacatg cttatccact aagggacgat    42780
atgtttccac gtcagcaaaa tggttaattc cattttcttt gttaaaaaac cttattcaat    42840
ggatatttaa tatcatataa aaaaattacc atctaaaagt acaattagtt tgactatatg    42900
ctattcaagt cctcatagtt ttattattca attataagtc agtcataata gaaatttaaa    42960
cttgtttcca tgttacacat taaacaccag tttgaaaaaa tcaactctga tttttataat    43020
aaaataaatg taatctcaat catctcctga acttcaacaa gtaaaacgtt aattagtttt    43080
gataatttca ctgatttgtt tcataaaaac acctatactc ctataaataa ttaaatattg    43140
taggcacgag gtatatagta gagaacgaaa gttggggtca attatagaaa tatttaaaac    43200
atacgggcaa aaaatagaaa ataaaggcaa taaggaaaaa agtataggt caagaaggaa     43260 ttataaagtt gataatttc ttgatttaaa aattcagtat atatatcaga aaagccccaa     43320
ataaattttg ggtcgttaaa aagaaaagaa aaagagaaat agaattttgc gtttcaagta    43380
ctccatctcc gtctcttttc ctccgcatct aaaaccatct gagaaatatc tccgacgaag    43440
gagaagaaac gaaaatgacg gagactggag taatcggatg tggctgtcgc ggagtcaccg    43500
gcggcaattt cttccatccc ggaggatttt ctttgaaatc ttgtttcctc gagcagagta    43560
caaagcgtaa tcgtaacttt ttccgaagcg tttctatgat tcctcctttc aaacgcggtc    43620
gtttcatcac taagttgcgt tccgtcgccg ggaacagccg aatctttagg taattagttt    43680
cgctctcgct gttaaattca tgaaaaatgg aaatcgatta catcattttc gttagtggaa    43740
tcaatttggg gaagaaatta gttgtctgcg agtgaaattg gattggaatt aagtgatttt    43800
ttaatcgaat tgttgttgtt gttgatgaac atgattaata gcatggatgc tcgagagaaa    43860
tcacgatcgt ttgtgttggt atcatcaagg cacaagagag ttccagtttt tgtgatgatg    43920
ccgattgata catttggaat tgatgcttct gggtgtccaa agattaaaag gttaagtttc    43980
ttgaaatgtt tcaatgtacc cgatttatat aaccttacat ggtatgaaat atagtataat    44040
tcctttttca gaacaagaca agtctagttt cttcttttag taaatgatat atctatcttt    44100
attgtttcag gctcaaggct ttaactgtat ctcttaaggc actcaagtta gctggtgttc    44160
atggaatcgc agttgaggtt tggtgggga ttgtagagcg tttctctcct cttgagttta     44220
aatggtcact gtatgaagag ctttttagac tgatttctga ggcaggggttg aagttacatg    44280
```

```
ttgctctttg ctttcattca aatatgcatt tgtttggtgg gaaaggaggc atcagtcttc    44340
cactctggat ccgagaggtt ggtattgtta gaattacagg tatttagtta tttgtttgcg    44400
gtagagatag aaggttgcct gatgcggatt tttcttcttc ctttgaatat ttttaaggtt    44460
gagaactttt tctgatgaaa ccttggagac tatagatttc tgttacacaa tcatagatgc    44520
taacttgatt atgttgtcgt tgggaatgct ttcctttgtt acgaagttta gctcaactgc    44580
ttttcacctt ataatttcca gattggagac gtcaataagg acatatacta tagagataaa    44640
agcggatttt ccaacaatga ctatctcaca cttggagtcg atcaacttcc tttgttcggt    44700
ggccgtactg ctgttcaatg ctatgaagat tttatgctca gtttttcaac aaaatttgag    44760
ccatatcttg ggaatgtgat tgaagaaata agtataggtc ttggtccttc gggggagctt    44820
aggtacttct gatcttctgt ggactaccac cggtaaagcc acaatagcta caataggagt    44880
ttcttacaca gttatctctt gcagatatcc tgcacatcct tctggagatg ggaggtggaa    44940
atttcctgga attggtgaat tccaatgcca tgacaagtac atgtgagtgc ttatttattg    45000
aaaatttgta tttgcctgta ctaatcacac ttacagattt atactacttg gtttaggatg    45060
gaagacttga tggcagtggc atcccaagaa ggcaaacctc aatggggaag cagagatcct    45120
ccgaataccg gctgctataa tagctttcca tctggagttc cgttctttga ggagggcaat    45180
gatagctttc tctctgacta tggtcgtttc tttctagtat gttctatatc atagcctctt    45240
tggtgattct gatataatat attgttatga tataaaagtg gctagtaggc tggattatag    45300
ataacaacgt gaactgcttt tcattgtagg aatggtacag tgggaagttg atttgtcatg    45360
ctgatgctat tcttgcaaag gcagccgatg tcttgcggag acgtcaggaa gaagagaaaa    45420
gctctgtaat gctggttgca aaaattggtg gaatctattg gtggtataag acatcttcac    45480
accccgctga actaactgca ggttattaca cacctccct cagggatggt tatgatcctg     45540
tagcttccgt cttgtctcgt catggtgctg ctctcaacat cccgtgagag ccttttttctg   45600 aagtttttctt ttactatgta cataattctc agaagctgca tggtccagtt tcactaacga    45660
gagaatctat catatctttt cagctgcttg gatatggcag atagtgaaat acctgagaaa    45720
tatctttgca gccctgaagg attacgtaga caggtacttt cttcgtaaa cccttgatcc      45780 agaattcaat tatgttcata tgaagtatgt atgttacttg tatttagacc ggtcactgtt    45840
gaagcactat ttacttccgt agagacactt caaactagtc tagtctctgt gttcttactg    45900
cgctgctaca ttagacaatt aagcatgcct tataagaaca tgaacaaatc agcattatca    45960
cattttcttt tgctagatac atgatgtttc gaagaagtgg acaatacatg tgactggtag    46020
aaacacaagc gaaagatttg atgaggtgag ttatttgcac atgctttagt cttatacgtc    46080
tgaggtcaaa gtggtggtta ttaaccatt tctatatgaa ttctgcaaca gatgggacta     46140
aggcaaatac gagagaactg tgtgcaaccg aatggcgaca ctctaagatc atttacgttt    46200
tgcagaatga atgagaagat ctttagggtc gagaactgga acaactttgt cccttttcatt   46260 agacagatga gtgcagatat gtaaacacac tcaccaccca ttggtgtgtt tgtcttttgt    46320
tacagaatcg atctttcctc accatattgc ttttcagat atgtgatgag gagaactaat     46380
caaatcaaaa attgttatat gataaaatct ctctctgttt ctattcttca tttgttcta    46440 tctctattgc aaaagtcttg cagaaacctt tttcattgga tcaaaagtt acattgtatg    46500 ttttgattat cagaaagcga tccaatacag aaggtttaat cacagcaaat gtgttacata   46560
caaagatatt attgaatcaa aggacttgcc tatcagcagc ctcggcaaca agaggcaacc    46620
```

-continued

```
tcggggtcag accaaacaag caagcagaga atccatagat caaagagaca agcaagaaga   46680
ggaacactgt gctgtccaaa ctcatcacca catctaaacc aaacccatct ctaggattaa   46740
agctcctctc aagcaaatcc gggaaaatca acaacacatc aagcacaatc gcctgcatcg   46800
tgttgaacct gacgtacctg ctgaaattag ggttcctcac aacgacgaag tagagagtga   46860
tgaagataag aaacccattg aaagggaagc tcttgaaagc tctgatggcg ggaaacaaag   46920
gttggatgag aatctgaaaa ggttggtact gtgtgatgat gaatttgccg tattgaatcc   46980
catcgaagaa tgggtagaag taacagacgg ctgagattat ccgatccgat gcatcgacgg   47040
aatcatcacc cttggattgg agtacgagtg tggcggctct gtccctggaa agtctaggtt   47100
ttgggaattg ggtatcaagg tttagaggga gaaagaacg accggttagg gttagggttc    47160
cggtgagaga tggtaatgga gcaaaaaact gagatattat tgccattttg ctctgttttt   47220
gtttcacttc acacaaaact gaaagactgc ttaacacatg atgagaggat aataaactaa   47280
actccactct gttttaaaag tttagcttaa aacattgtgt cgtcttctta tctttctaat   47340
atgataaaac ggtacgtagt tatttgaagt aaggtaacaa ttaaatagcc tctgttattg   47400
tctttgtttt ttgtgtatat ttaaatatca aaatccaccg gtataaaacg gcgtaatgcc   47460
tttgtattgg acccaattct ttcaattttc acctaattta attacctccg tatttatttt   47520
ttagtgcact tcaatgtctc ttgcatatat atattggagc aaattataaa cataatgttc   47580
atagtgaaat tgttagttgg ttttaatctc ttttaagac aacatataat gtcaattgta    47640
tgtacgtttt tcttgtttct cttaaacact tcttttgcgt ttgcatttgc gattcctaaa   47700
ccgccaatag taaggagact atcaacgaca gtgacatcaa attcaacagc gtcttcttgc   47760
tcagccaatg gaaatccaat cgatgagtgt tggagatgcg acgaaaactg gaaggacaac   47820
cgcaaaaacc tcgcggattg cgcggttgga ttcggacgcg actcaattgg cggtagagcc   47880
ggggagttct acacggtgac tgattcagga gacgacaatc ctctaaatcc aactccaggt   47940
acattacggt acgctgcgac acaagatcaa cctctatgga tcattttga tcgagacatg    48000
gtaatacaac taaacaaga tcttcaagta gcttcataca aaaccattga tggtagagga    48060
aataacgtac aaatagctta tggaccgtgt ttaactttat ataaagttag taacattatt   48120
ataaacaatc tttatattca cgattgtgtt cccgtgaaac ggaatgcttt atcgtcgttg   48180
ggaggatact cggatggaga tggaatatcg atattcgagt ctcgagatat ttggattgat   48240
cattgtacgt tagagaaatg ttacgatggg cttattgatg cggtgaatgg atccacggat   48300
ataacgattt cgaatagtta catgttgaat cataatgaag tcatgctttt gggccatagt   48360
gatgagtatt ccggtgatcg ggatatgcga gttacgatcg cgtttaacta ttttggtgaa   48420
ggacttgtcc aaagaatgcc aaggttagta caatcttata tttctttttc ttctttttt    48480
aatgtcaaat ttataagcta accaaaatat tcgtgcttaa aataccaatg tgtaggtgta   48540
ggcatggata ttttcacata gtgaataaca tttatagaga ctggaagatg tatgctattg   48600
gtggaagtgc taatccaacg atctttagcc aaggaaatgt tttcatagct tccaataatc   48660
agttcaccaa ggaggtacgt tcgtgacatg tgctccacaa aactaagagc gttttaacct   48720
cacaattagt acaatctaat tcatagtcga ctaatcattt agaaatttga ttttcatgtg   48780
tcttactata tggattagat tctagacgga aatgtttgct ccatacttct aaactccact   48840
gccctatacg caggttacaa agcgagagag tgcagatgga gacgaagaat ggaaggaatg   48900
gaactggaaa tcagaaggag acgaaatggt taacggagct ttctttacac cgtcaggaa    48960
agaggattct ccgagctacg cgaaatttc gagtatggta gctcgaccag cttcacttct    49020
```

-continued

```
caagaccaca catccatcag taggtgttct tagttgcgaa attgaccaag cttgttaaaa      49080
acacaaacat aagcttgtga ccaaatctag tgtttgtcct tctttttctt ttttgctctt      49140
ctacttgttg tggttattgt tatcgtaaat aggatttgta ctgaatgtga tgatgatcat      49200
agacccaaac aacaattgtt cattgtcaat ttctttacca aaaaatttct tttacgagtc      49260
acaaagtttc gtcagttttt ttatttataa atacattaaa attacttaac aaccttttc       49320 catcggataa aactaagatt gacactcatc attaataatt ttatatatac tcccattttt      49380
tttagtgagt gttaacataa gattaggaat tattcgtata ttgttagttt cttttattct      49440
aactttccca atcatattgg gattgagctc atcccaatat gtataaatag cgtactcaag      49500
agaccaatca tcaagtggct agtaatgtgg ctcaagacct aatttcgtag ctagctactt      49560
ttttatttgt attttgtata taacacatta aaggcttttt tttcctttga ttcaatgtaa      49620
atttcgttac ctttcaaatt tctgattgt gatgatctga attagttttt ggactcatta       49680
tgtgaaaatc agttagacaa atacaaaaac aagaaaaata tgacaagatc accaaaatca      49740
ggacttgttt acatcatcaa ctaaacaaac acgtgaaaca agaacacaca aatatataaa      49800
ctaccgacta tttaattcga caaccaactt ttaaataaat aaaaaaaact caacaataga      49860
gggaaataaa taatcctcat ttactttccc ccaaaaacca taaataaaag attcacaaaa      49920
aaaaaaacat ggaagaatag aagaaacgaa gtgaaactat agaagccaag aagaagcaaa      49980
caagcagagc aagctcacca                                                 50000
```

<210> SEQ ID NO 8
<211> LENGTH: 36699
<212> TYPE: DNA
<213> ORGANISM: Arabidopsis thaliana
<220> FEATURE:
<223> OTHER INFORMATION: nucleotides 50,001-86,699 of clone MDF20,
GenBank No. AB009050

<400> SEQUENCE: 8

```
ccaaaccagc cttagctcct ccgatgatcc taaccgcacc agcatcatct gccgtcgcat        60
catcggcctc tccgtcaggc ccttcggcag gcgaatccga gtcaccaaaa ggatcattat       120
ctggcgacgg tgcagccttc ttcttctttc ctttcgcttt cccttagcc gcttttggag        180 aatccgcaac atcaccatcc tctggtgccg gagcaggagc cggagcttca acagccgaag       240
ccttaaacaa ctcttaggc aacaaaacct tatcagtcgc atatatagct aaaggctgct        300
catcaataag agtatcaacg atcttgacag tgttgatcct tgtcttgagg gtaaccttct       360
ctccatcgtt ctgtacagta agctcaaact tgttagctcc atctgtcgca agtgtgttca      420
tcggaccatt gttggatttg agcatcgcca ttgagtaata tgtcgggaca gcgaggaaat       480
cgagaaatgc ttcttctt ggagctgtca agttcttgta tttgggcaag aaaccttca         540 ttgcatcatc tcctggacag aacactgtca tgcctccttc taaactctcc tgttacaaca      600
taaacacaat ccaaacccg gttttaatct ctcaagatca atttggtcta tcttgaagtt       660
gacttgatta agatagtgaa gttgaaactt ttgtagctac tcaattataa tggctagtgt       720
gagttagtgg agacaaatta ttgttacttt tcatatttga aaaagatgaa ccattttaa       780 aaatttagtt aatagaattt ggtttcataa atttgaattg gaaactaac taattatgtt        840 ccgataattg aggtaattaa gtctatatgt tgactatat ttgctaattg cttacgaaac       900
agtcaacacc ttttgacctt tttctttttg tttcaaaacc aatgtggcaa tagctattgg       960
ctacaataca acagtacaat cacatgcatc ttttctgaat aagtaacttc tcatttaaca     1020
```

-continued

```
acggaaatta aaaggataat cattttagat agagctacta atcagtgtta attatgtaag      1080
tagtaaatat ctgatttctt tttttaataa tttctaaatt tatacagaca catgcatcta      1140
cttattgatt atttatgtta taaatggaaa acagaaaact aatacttta ctaaaatcag       1200 ggttagtagt gataagtgta ccaattacat ttattaatta gtacacagcc acatgcatat      1260
aattattgat taattaaaca gaagattact aattatcgta attaattact aatcaggggt      1320
ttagtatagt acctgatagg tttttgaagc tccagggtta gtgagaagag tctcagcaaa      1380
cactttgcat ccatgagccg acattattcc ggtaagattc atctccgccg gagcaggagt      1440
cggagccgcc gcagtctccg acggtaaaac tctactgatc tgaataatgg agatgttata      1500
cggaacttct tcaatagatt taacaaagaa agaagacaga tctccaccgt caggaccaaa      1560
cccaacttta ccacctctca gatccgttat gttaacgaat cctgaggttc caggagcagc      1620
tccggtggct tgaaacagag tagcggcgag agcagagccg tcacggatct ggtggagttt      1680
tttggttccg aagtaatcta aaaggacgtg gagggagaga atgttttttga gagttgagag      1740 tgtatagcct ttagaggtta atgctgacat ggcggcgtta tctactgcgc aaacggttat      1800
ggttcttctc cggttgattt cgtcggcgag gtgtgtttgt gttaggaaat ggctgaagga      1860
agagaatgat gggtggtttg ctaggaggcg cgtgacgttg tgcgcgtggg tttgagttgt      1920
gaggagaagg agaatgttga agatgatgat gagagaactc atcttcttgg ccattgttgg      1980
agagagtgaa gagtttggtt tggtgatttt tgagagagtg tgagtgaaga agagcttaaa      2040
gtgaggggat gaagaagaag gtggtgttta gttttttaatg gacgtggttt ttggttgtaa      2100
ttacgattgt gccattgtat ttatttattg tgatgacatt attttattgta tttattgcga      2160 atttaagctt atgggctttt gcaagttttg tgaccatgtc aaatgctctt ctttccagcc      2220
ttccacgggt tccacctagc tactatttta gaattatta acgattgtt gaactttcta       2280 gaaaaatgga agttttatg aactaggtat ctatatatgt agacgaaatt aaatatagga      2340
tgaaacaagt gagacatgct aatctttcta aagagaaaaa gtttatgatt cagaaattga      2400
tatatttgtg cccatatttg tattattgtg gtctagtttc gacattaagc atcaagagga      2460
aaccattatt tgaccacatc gccgctacaa atgtttgatt gcctttacta gacattattg      2520
cttcggattt taccctataa tattgatact ttggtagact aagtgtaggt aaaaaattgt      2580
aagtttatag aaaagtatga gggaaattaa aaacaatagg aattgcgaca acgcattta      2640 gcctaaagca gattcaaaca gccttacgaa attcatttgt aattgtagca catgtcccca      2700
actaatctta acctaacatc tacagagtgt ttaaatgtca aatttatttt ggcttagcaa      2760
tatttatgat ttgttctcct tttgttgag aaatttatag tggatcataa ctatcatgtg       2820
atttgtatgt gtagctaaaa atagaaatac ctttttagac tcaaaaacat acaaaatttt      2880
catattatta tataatcaaa catgtcacgt gggagttgga agagtatctc ttcgtcataa      2940
attaaggtat cgtaaaccca ttactccatt attaataaaa attcaagctc atttcacaag      3000
catagaatct tcttcttctt cgtttataaa acaaatcttt atttgttcct taaagtttga      3060
ttagacccga atctacgaga ctttgactgt agcaatgtca tcagtgtcag tgtcggtgat      3120
aaaacgtaag ttaaagtgca tgaatgcgtg atcgttacgg tcaggtaaaa ccggagatat      3180
atatatgaag caatttcatg gtttatatgc aaaaattcag gggtacttgt gtaatttatg      3240
ttgtctgaaa atggtgacgc aggactcaag gtaccgacta accacgtgga tggttgagat      3300
ctgttatcag attctccacc gacaatcggt cggtccatgt actggctgga ctgagtaaaa      3360
```

```
ctagttgttt gaagatctga cgcaacggtt tgttgtccca tgtcacttaa gatacgatgg    3420
ttgttgtgtt ttataattaa acaacagtaa tcacaaagct tctcaattct tgagagtcta    3480
aatatacatg atcaaattta taatatttca tacacataat tatcatttgg aacctgtacc    3540
catatcatat aataacaatg ctaacatcat ttgtatctca ttgatcctag tatgtgtctt    3600
atcattggca acaaacacat ggactccttc ttctcctgta atctgtatcc aactacatcc    3660 aggtttttc ttcaaaccct tagctttcat catctctctc atcttcacaa cttcatccca    3720
acttccttca accgcataag cattcgatat cgtcacatag ttaccggagt tttcaggctc    3780
ggattcaagc aatttccttg ataagtagtc cacaagctca gtcttacgct gtttgttgca    3840
agaagcaacc aaagattgga tcattcgtgc atctggcttg aatggcattt cctcgattaa    3900
ccttaaagct ttttctgttt ctccagctga tgcaagaaga tctaccataa gtccataatg    3960
ttccaagcat ggtttcatac tacgctttga acgatatca gtgaaaatct cgatagcctg    4020
gttaatatcc cctgcgtggt tacatgctga taagacattt gtgattgtga tgttgtctgg    4080
tttaagacct acaccttcta agcttctgta tagagcgatt gcttctttta agttaccata    4140
taatgcatac gccgagatca tggcattgga gagaggcaac tcgctgtata gcttacttcc    4200
gaaaaccttc tctgctttgt ttatatctcc acatttagca tacatgtcaa ccaaagaagt    4260
ttcaatagaa accaaagagg aatgctgtag atttcttatg atgtatccgt ggattgttct    4320
tccgatatgc aatgatgcta gatgtgcgca agcagagaga gcgacagtga tgctaaatgc    4380
atttggtctc aggcccgatt cttgcatctt tctaagaaac agaattgcct cctcactgca    4440
accattttga accataccat tcatcatagt cgtccatgag ataagatttg gaattatccc    4500
tgaggattgc atctgcaaga acatatcctt ggcctcatct acctgaccat tccttagaag    4560
acttagaatg atcaaattcc atgttatcac atttggaggt acaccttcta gctgcatccc    4620
atagaacaat ctcaaagcct ctccactaag accagattct gcataggctg caagtaacgt    4680
attccacagt atcaagtctt tctctactgt agaatcaaac actttcttag catcaacaat    4740
gctgccacac ttggcataca tatccatcac agtgctggct aaaacgatat cagattcaaa    4800
actatgtcta atgcaataac actgcacctc ttttcccgagc tttagattct cagtacgtgc    4860
agcagcagac attaatgtcg ctaaagtgac acaatcatat ttcagcttct ctagtctcat    4920
taattgacac atgtagatag catcttcaac tagcccttgt tgaacatacc cagaaataat    4980
cagattccat gtaaccacat cctttcaaa catccgatca aaaccatct cagcatactc    5040 tatcaaaccc actttgcaat agaaattcaa taaagatgtc cccaagatat tatccagctc    5100
cattccattt acaatagcaa tggcatgcga ctgtttcccc tcttcaaccc cacccatatt    5160
agcagaagca gataagcaag tcgagacagt gacacgagta ggctcaacac cttgcttcct    5220
catatcagaa aaaagccgaa tcgcttcctc attcttacca ttttgtacat aaccaaccat    5280
caacgcattc caagcaacag catttctgtc aggaatttca tcaaacacct tactcgcatc    5340
atccaaaaca ccacatttcc catacatatc agctaaacta ctagccacaa acacacaatc    5400
ctcaagacca gattttacca catacccatg aaccctctc ccaaatctac tccatttcaa    5460
cgcaccacac gctttacaaa cattcggaac cacaaaatta tcaggaaaaa tctcattttc    5520
aagcatctca acaaaaccca ttaaagctcc ttcacataac ccaatcctac atttcacacc    5580
aataatagct gcccaagaga aaacattacg aaccctcaat ttcgagaaaa gaacttcagc    5640
aatctccaaa gcatcgcact tggcgtagaa tatcaccaat ttagtctcga tgtactcatt    5700
cctcgcgtag aaatcaccgt tctttaaaat ccgagcatga atttgcttcc ctgtacttaa    5760
```

-continued

```
atctctctcg taaacgcatc cttggaggat ttcaccgtat atctcaggac caatgcgtaa    5820
gtttctgaaa tccatctctg taactaaact cagagcttct ttgatctcac cgttcttaca    5880
aagagacgaa acgcgatgaa agtaagatgt ggaagaagga gaatgagctt gttcatcgtg    5940
gtgtttagaa gaaggtttcg atgatactga aaatggaact ttattcggga tagtgttgaa    6000
aggaagagaa gccattcatg cctctctgat aaacgtctct gaagataaaa cagagttctt    6060
tcgaatcctc gtatttaaat tattttattt attatctcct cgacttcttt tcgtaaaatg    6120
ttctccaccg ttgattcttg tggcaaatac agacacgtgt acggttttca tctgttactc    6180
gatacatatt tgtaccgatc gcgattcgta tgtgtaccaa ccggttttcg atttgatctc    6240
ggtttagttg aattataacg ttgaaaaata taattcat ttattagaat atacttcaaa    6300
agtaacgaca aaaaaaaaat acttcaaaag tatataaaca aaaaatttga gataataaca    6360
gaagaagaag gtgacatttt ttataggctt ttaatattta tctgaaacct atgtatgacc    6420
taaaagacaa taaaagcatt agctaacaca agcatcaaaa catatacggg aatggaagag    6480
gaatagtaag ccatcgctga accggttgta ccgccttcgg ctcctcctcc tcctcctcct    6540
tggccgccac cgccttgtcc ccctccgcca atagtaccgt aaggataagg aggagtataa    6600
aaataaggat acggaggaga atacatcgtc gaaggtggtg gacctggtgg ttggttgcaa    6660
cagcctgtcg tcggaacagg agggcagcga gaacgtggcg gtgaagactg tgaaggcggt    6720
gggggtggtg aatactgtgg agacggtgga ggagggttac catatggaga gtagcctgta    6780
gaggacggtg gttgaggcgg ttggttacat gggtaaggag tgcaaaaacc agcgtttgaa    6840
tccaaagctg agtttagatt gacacagttt aaaagtgata gataaaaggt aataagagga    6900
acagagagag aagcttgaag agacaacatg atgatgactt agagaaaatg atgagtgttt    6960
ggtctttggt tttgagattt ataataaaaa gagatgaatt ttttcctcgg tttcgtatta    7020
tctgccgcat ggcattacac atgtcggggg tgttggagga tttctgaaga aaacgtttgt    7080
gtcttttagc tgatgtagac aaattttttgt catgtaatga caaattaaaa cgcatttgta    7140
ttactttgga atatatagat atataccgat cggtaccatt ttcatcaata gatgtcccaa    7200
agaagatgga ttatgagtaa catgagtttt aagataattg tgacaagtcg aatgaatctt    7260
ttgctatggg aaagatgaag aactatgaat tgtttcaagt aatcaaataa tcaaatttta    7320
cgttgaagac ggggtttaca cgatggataa tatgtggctc caactaagct gttgcatgct    7380
cccgagttgc aattacattc aatcgctctg gcccatgtag tgaaggctga caagagcaac    7440
cagaaaaaag ttgatgaggg tcatttgtta gtaaggtgct agccttcaca ataaactgct    7500
taattatgat aactttaacc ctcgctttga aattaccatc gatgatggct ttttggacaa    7560
gtttggaaaa agtatccacc aaactcatga tttgcttgtg cattcatggt gctgggtgag    7620
tttgttttga ctagtctgtt gtaggattca actacttttc aaatgatgca caagctagtg    7680
ttgaggtgtg actacacttt cggacagtat tgtatccgag gaaatattaa ttctgatggt    7740
gtgggttgtg gtcttgtcga gagtggaatg aggactaaca taacccatat ttaagtctgc    7800
atgctgcatg ttttttatta aaaaactgtg tgaggtatgt taatcttgat aaataaattg    7860
atgatatata acaatactta tttatgaaac ttagatatgt tataagttta ttcaccaaac    7920
tgaattcaaa atggctttga gtgatgagtt tcaaaccggt tcgatagaac aagattttaa    7980
tctaatataa gctcatggtt gagcatgcac cagaacgtca catagaatca atttaaatcc    8040
atagtaaacc ctgtcatatg gtttagtatt ttacaaatta caacccactt tatcaaatgg    8100
```

-continued

```
tttcaatatt caatgtgttg acatttacct atatatttta aataataaca agacgataaa    8160
tttacttatt taataactca ttgtattggt ttaaccaatt agatgaatgt tgtttacaat    8220
gattcaagga taccgaaacc gagttcaagt tttgttataa gatgatctac aaccgtgagc    8280
ttgacacaaa tattatcagt ctaattctgg gactaaagag attatggatc acatattcat    8340
aatttcatga ttacataaaa aaagtaaaaa taaataaatg atatatagat aaaaattggt    8400
gaaatgtatt aaaagttgca atgatatcac ccacttaatt tagctatgat attttaggtt    8460
aatgtaatta atgttttttct tatatcaaat ttttgtttag ccaaactaaa caaatttgag    8520
aaatataata acatgccata aaataagttt tatatgaatc caattaatac cctaatttgg    8580
attttcattt aaatatcaca aactttaggt ttatcaggga aacataataa agaaatgtta    8640
tataaaaatt tagcaacact tttaaaatct aaaatctctg atattctgag aaatgtcaaa    8700
aaaaatattc cagattgcat ataataataa aatcataata aaagaatta aaatatattg    8760 atacttcata aatagaagtc actgtccaag tctctgctttt tttatacatc gagaggcaga    8820
gaaggtgttc ttcttcttgt ccaaaagaga agacaaaacc taaatgtctt taggttacgc    8880
agagaaatta tccttcattg aagatgttgg tcaagtcggc atggctgaat tcttcgaccc    8940
atctcatctt ctacaatgca aggtttctat ttttttgttc cttctcctcc tggggttttg    9000
tgggtttact ctattttttct cgagattctg tataatttca cgttgcgttg attttttctc    9060
tggattaatc gcttagctgt ttagatttta gagttgatcc ttcttgtgtt ctgtcctagt    9120
gtttgatttt ggatcgtagg ttcatattaa gcctttaagt ttttatattt gtcgtttgga    9180
tggtcgtgaa gagttgttga agagttggag aatgattagt acttaatgat tcatataatc    9240
tagttttagg ttatacagta cctgttttta gacttgcatt gtgttgtgtt aattgaagaa    9300
tgaaatttgg tgataacaag catcttaaga ttatgtgatt ttatttactg attatgtgaa    9360
aaccgttgtc tggattcaaa tttgtgtgga gattttgact gtttgtttat cattgtttta    9420
tctaacaagc caaaggtct gataaaagga tttggttgct agatcttggc gtgtttattg    9480
tttatttcac tattgtgcta actctggtgt ttgtctttgg aaatgcagat tgaagaactt    9540
gctaagttga ttcaaaaggt ttgaatcttt accctcttttc gtattcttct tggtgctttt    9600
gaatatatgt ttttggtttc ttgttgttat taagtatct ttaagaaggc tggtttgatg    9660
tttgcagagt aagcatctag tagtctttac tggtgcaggc atttcaactt cttgtggtat    9720
tcctgatttc cgaggcccca aaggaatttg gacgttacag gtgtgagcta aggccattta    9780
atcctctttt ctttgactat ctgctcgagt gatttgattt tgaattctgt cattgattgg    9840
tctgttatca tcacttcttg acttgattgc attgtcttgg attatgtggc taatatactt    9900
gtcttttgta aagcatcatc tcttgaaagt taactcttgt gatccgtgtt taatggtttc    9960
agcgcgaggg caaagattta cctaaagcat ctctgccatt tcaccgtgca atgccgagta   10020
tgacccatat ggctttggtt gaattagaaa gagctggcat tttaaaattt gttatcagtc   10080
aggttatcct cttttcccta cagaattact ttataactac cgtgcttgaa cactgatagg   10140
atcttgtctt catgtttaca tttctaattt cacttatatg ctgccttcat aaatgatcag   10200
aatgtggatg gcttacatct tcgatctgga ataccaagag agaagctttc tgaactgcat   10260
ggagactctt ttatggagat gtgcccatca tgtggagcag agtaagccaa aaatatgtta   10320
ttgcgtttct cttatactgt gaccccttgt gattgagagc tgtcataatc tatccgtata   10380
ttggaccata aatggtaaca acctttcttg aaatttcgaa ggtacctgcg tgatttcgag   10440
gtggaaacta ttggattaaa ggagacatca agaaagtgtt ctgttgaaaa gtgtggagct   10500
```

```
aaacttaaag atacggtctt ggattgggag gtaacacgaa agcgttgcct ttgaatcaga    10560
gtccaccagt tttacctttt tatgtagtta aagaatttaa gaaactgaat tatgaaactt    10620
tctttatatg actcttatgc tgcaggatgc tttgcctcca aaagaaattg atcctgcgga    10680
gaagcactgc aaaaaggctg atcttgtact ctgtttgggt accaggtaat taatgactca    10740
taggaactct catgtttgtt tccttaacac ttttgatcag ttagccaaac aactctcttc    10800
tctagagtat gttgcatttt gtttgttata tgtgtctaac ctctttatgc agtttgcaga    10860
taaccccctgc ttgcaatttg cctctcaagt gtctcaaagg tggaggcaag atcgtcatag   10920
ttaatcttca ggtaattgtt tattttgttc atgtgcacga gatttaatgc gcgccatata    10980
tgtaaatgaa attttctccg tttgctgata ttttctctgg aatgtatatg cagaatgag     11040
ttttctggac tgtgtagttt gtgactgatt atatttaccc tttcagaaaa caccgaaaga    11100
caagaaagca aatgtagtga ttcatggtct tgttgataag gtaagattta cgttttgttg    11160
ttttcaaaaa ttctggacat aacctaagtg atgtttaaca gattaccttc agcactgtgc    11220
cccaacttga gtcttataga ttttttccct tcattattct gatgtgcagg tggttgcagg    11280
ggtcatggaa tcgctcaaca tgaagattcc tccatatgtc agaattgatc ttttccagat    11340
aatcctaact caatctataa gcggaggtag cttttcctga atctttcatg gttttttgtgc   11400
aacatatatg tcttgtcctg cactgtaatt gggtgtgtca aactttttat taatgatgtt    11460
aggcttcata gctctcactc acatgttttt catttctgtt acagatcaga ggtttattaa    11520
ttggaccctg cgtgttgcga gtgttcatgg attgacttct cagttaccat tcatcaagtc    11580
tattgaggta atctctagaa actactaaac caatgccaaa acaatcaaat tcaattttc     11640
tgatattttt catttgcaat acaggttctt ttctcagata accataatta caaagacgca    11700
gttctcgata agcagccttt tcttatgaaa aggtaaaact aacctcttct tagaaatcag    11760
tttcttgtcc tatttctaac tcttatatat attctcatcc tctttcagga aacagcacg     11820
aaacgaaact tttgatatat tctttaaagt taactacagt gacggttgtg actgtgtctc    11880
cactcaactt agcctcccat ttgaattcaa ggttattac gatccataaa agatctttgt     11940
tatcttgact catgaccatt tttctcacaa cattttcaaa taacctgtgt agatttcaac    12000
agaagagcat gtagagatta ttgacaagga ggctgtgcta caaagcctga gagagaaagc    12060
ggtagaagaa tccagttgcg ggcaaagcgg tgtggttgag agaagagtgg tttctgaacc    12120
gagaagtgag gctgttgtgt atgctacggt gactagtctc aggacttacc atagtcaaca    12180
atctctgctt gctaatggag acctgaaatg gaagctggaa ggttctggaa catcccgtaa    12240
acgctctaga accgggaagc gaaaatcgaa ggctctggca aagaaaccga aggcatagga    12300
agaagaaaag aaagcttttg gtgtatataa agaaacacta gtctaaccgg aataggtaat    12360
atggaagtta ttggcgtttt gagagctgag tgaattttgt ttttggtcca cattcggttc    12420
tcttgaaaca aaagttaacc aggaattgaa agagataatc ttggttcgtt gtcgtttagt    12480
atcggttgat ttttgtagaa gctagtgcat tcgaaatatt attaaaaaaa atttacaaga    12540
tgatcaagcg atgccagaat ctgtcgactg gtaggaatct cggatttgaa aaatacataa    12600
aacgacatgc tctcaataat ccagtactgt tgctattta gctttaaaaa cctagtggtg     12660
aacaattaat aatgatcaag aaaagatgtt atagtacata atttagatat acattgtact    12720
gttctatttt aatataatat gcaaataatg taaaacaaat caacgaaagt tagctgtact    12780
tatatgacat cgtcagttag aattcttttt tttttttat gttttttat tgaataaaag      12840
```

```
gataattatg tttttcattt tcaagggatt attttttcca agtggcaatt aatatttcaa    12900
gtgggaacat gtgtcaagcg aaactttttt ttttttttc acaatattga ttgcaacttt     12960 tttgttttgac aacttttaac tgttaggaat taaggaataa ataaaagatt caaaaaaat    13020 ttcgttttt gtttgacatc aagagatggt ctcctctcaa atgaaagtaa aatagaaatc    13080
tatattcatg aaaaagattg gacagctatt caaaatcaat aatgaacgac ttgttttttt    13140
ttctattaac aaagaataga aaaagaccaa gcttagctac agctgtatta cgcaagtttt    13200
atatgaaatg accggctaac atatatatgc aaggggaaga ggagaataca aatatcacaa    13260
aaatccaaat ttcctttgta gcaaccatga gttccgtggg tgtatttcgt aaggaggaaa    13320
tcgatggaaa cccatatttt gtgatattaa cagaaacaaa agttgatcaa aaagaagaa     13380 aaaaacata ttttttatgt cctgctgcac gtataaaata tctaaagttc aaacgaaaga    13440
tgctcgagaa ttatgattat ggtgacgata acgaagacga cgataatgat gctgacgaag    13500
atgccaaaga agatggcgat ggtcatgaca agctgtatcc attcaattct tcctctcact    13560
tccccaacac aagacgcggt gatcgacaag gcaaatcttt gcttgactgc tacctccctg    13620
gaatctgtaa gaaccccgta gttcctcttt tcaggtacaa cgataaagaa ccttattgtc    13680
acatatccca gtgcggtgca tgcaaaggga aaatgctcga cacaagcaaa gattatgcat    13740
gtctccaatg tcaaagaaag ttccacagag aatgtgttga gtctccactt gagatcaaac    13800
acccttccca cccctttcat tctcttcgac tttacggtct tccaacgttt cagaagtgct    13860
tttgttgtga acatctctc tacgacatgt tttatcattg tgctacctgc gatttgagta    13920
tgagtccggt ctgtgcgttg aagccggtac ccattgtcat agaacaatca agaagtcatc    13980
accatcctct cacctttttc cctgcacaag ctttaatttg ccatatatgc gccgtgatta    14040
agaagtttga tcccgcatac atctgtgtcc aatgcgtctt tgtcgtccac aaaaactgta    14100
tcggttttcc acatgtcata agaatatcac gtcactctca tcgtatctct tttacgtctt    14160
ctcttccatc tagaaagctg tcatgcggag tctgtcggaa acaagttgac aacaaatatg    14220
gtgcatactc ttgccttgaa tgtgatgctt attttgttca ttcaagttgt gcaacacatc    14280
caaaggtgtg ggatggaaaa gaactcgaag gagtaccaga agaagatgat ataatagacg    14340
atggtgagcc gttcgagaga atagctgatg gaataatact ccatccgttt catagtcacc    14400
atctacgact tgagatcagc atagcttatg atgcaaataa gtattgtcga gggtgtgccc    14460
ttccaatcta tgaaggtcaa ttctattcat gcatggaatg cgacttcatc ctccacgaaa    14520
gctgtgcaaa tgctccgcgc atgaaacgac atcctttata tccacatcct cttacactaa    14580
aagttgccaa gcataatatt gacggaggta tatttcattg tagcgaatgc aggcgtgttg    14640
gtaatggctt cttctatgag tgtggtaaag agaataataat cgtccagcta gacttacgat    14700
gtgcctcgat tatcgaacca tttgattatc aaggtcatga gcatcccttg ttcctaccct    14760
gggaaacaga gaaagagaca cgatgtcaaa tgtgcaaata cgacagcggc cattcaaagt    14820
taatttgcat ggactgcgat tattctatat gtttccggtg tgctacattc ccatacatgg    14880
caaggtataa gcatgacagt cattttctca caatttccaa tgggaaagag gaaagtgatc    14940
agcaagattg gtgtgagatt tgtgaacgca aaatagtaaa agtaaaagaa agagggaatg    15000
tgctgtggaa tcagaaagaa gcattgcgat atagatgcaa tgtttgctgc accactcttc    15060
acatagattg tttacacggg aaagagatgt acatcaaacc tcgggaaaca gaacgagatc    15120
atctcacttt tcacactttt agagacatgg aaaggatatt tattagagtc catctcaaca    15180
gttctctctc ccgacccgtt tgcagtagat gcaatcgtcg ttgtccattc ccaatatttt    15240
```

-continued

```
tcaaagggtt aagactaatc tattgttctc tggattgtgt tagaaatctg ccacgttttt    15300
cccttttagt ttgaagtatt ttgatatttt ggcatgttgt ttttctaaag tataattttg    15360
agatgtaact tttcatattt aaaaagaatg atttatgtga tttttatttt tattttcgtt    15420
gaattttagc cacagttaac taatcctata cataatagat gaagacgatg ttcggaaaac    15480
tagtaggcgg tagctaggtt cagtagggc ttattataac acataaatcg atgaatcaaa    15540
gcctagatgg aacatatatg ttagtaaatt atttacttat tattctaata ttttcttagt    15600
tttataacaa aaaatatcta tagaatatga aatgtagtgg aagtctactt cgggttcatt    15660
aatattttta taccatgttt ggggttcaaa ttcttagtga gcggagtttc ttacatatta    15720
atggtataaa aattatttga gatccaaagt gatgtatgca tagtcgttgg taacataggt    15780
ttcataacaa aactttcagt tagatccaaa tgttgtggag agagtttcgc cataaagtcg    15840
atgttcgcag gaggtattca tcatagtaaa aaaaaaacat gcactacacc gactaaaatt    15900
taattaccga ttttgaacgt ctaattcgat aaactttttt ggtgttcaca ttaacacaaa    15960
cagacaaccc aacctcctcc agtaaagcat tagccatgga ttctggtggc cacaacctcc    16020
ctctacaacc tcaacctctt ccagaaaatt ttcgtttgtt ccatttagaa aagattacat    16080
ggttaaacta acccataaca tattaaattt agtcttttac caccaaaaaa gatcaaatta    16140
aatttagatg ataactgtta atacgaaacc tagttctttt ttaatctaac gttatatgaa    16200
ttgtagtatt ttccttggtt actctttcag tagtaataat attatgtata gtacacggta    16260
ataattttac agttttgtct tatgtgaact catgacatgt ttccgttcca tatgggatcc    16320
taaggccact tctattgcac aaataataga agtgtcttta gatattaaat aaataaaata    16380
ataaggtaaa tgtcttttaaa ttggtggaga aagggaatt tgtgtttgg gaagacatta    16440 aagacatgtt tttagagaca tatttgctta ggtggcaata tatcattggt tttttttta    16500 ttcttttatt ttaatcacaa ccaaagacat ttacttaaat ttgtgcaatg tagatactct    16560
aaggcttgct ctaatcgaga gtgtatttc atgtgaaact aatctttgga aagaagatcc    16620
ggaagagacg gtctcatcac tgatatttca tattaaaaaa gattgtacag caagaaatca    16680
ataacaaaca acttttctt cttataaaaa ctatataaaa tatgtttaac caaaaaaaaa    16740
caacactgta aaagacttgg ttgtattcac aagtttttaat attaaatggc tggctaatac    16800
aaatatcaaa tatgcaatgg ggagaaggag aatatcacaa aaatccaaac ccccagttgt    16860
agcaaccatg aggaaattga tagagaacaa ttttttggttt acacattaac acaaacaagc    16920
aatccaacct cttccggtga ggcactagcc atggattcta gtggtatttt gattgatctt    16980
caaacttgaa atttaatttg ttgtttatca agtctgactt cttaaattt ttttaatgtt    17040 gcagtgattc ctgagcaaaa gaaaaagaa acattgtctg gggcgaattc ttgatatatt    17100
tccgtcttca aagactttcg ttcatctctc taattagaat aacattaact ataaatgttt    17160
tagctgatgt ttaagaaagt aatttagatg acaaaaaaaa aaaaaagtaa tttcaagtta    17220
tgattaaaca ttaaacagga ttatgtccac ttgataaaag gacaattgtg ttttccaagt    17280
ggtacttcta tacattattt tcttaagtgg caattaataa ttttaactgg caggatatct    17340
caaatgaaac tttttttttca caatattggt tgcaacattt tgtttgacaa cttttaaccg    17400
ttacgaatct cggaattaaa aagaataaaa gacttgctca ataatccaat agttgctatt    17460
acaagttagt aaacgtagtg gcggacgaaa tattaatgtt ataagacata atttagaaaa    17520
aatatgttgt gttctatttt aatgcatttt ttttggtca acattcgaat taggccatct    17580
```

```
tatataaaga aattggacgg gatgaaaatt ttcattttgt tccacttact aaaaaaacta    17640
tataattaaa ctaatattag atttaaatat tagattctta tcacaaaaaa aagatttaaa    17700
atgataacta aatttgctct agctttattt atatgcacgg tagtattttc cttgtttact    17760
cttcttaaag taataaagat tgtgtaatat tgtacactct tattattata caattttgtc    17820
ctacgtgaag tcatgatgtt ccggttcccg ttcccatccc atatcaagat ggaatccgaa    17880
ggcttgtttc caacttccaa ccggagtgca ttttcatata aaacaattc tttagaaaca     17940 ggatccggaa gggacggtct cctcccaaat aaaaattgaa tagaaatcaa tatattatat    18000
ttaaaaaagg tactccgaaa aagaccaagc ttagttatat tcacaagtag cgattcgaga    18060
tcaatactga acatcaagca tataaaaaga ccaagcttag ctgtattcac aagtttgtat    18120
cataaatggc tggctaatat atgagaagaa gaagatcaca caaagaaat ccaaatcccc     18180 atcgtagcaa acatgagtga agtcggtgta tttcgtaagg aggaaattga tggaaaattg    18240
tttttggctt acacattaac acaaacagaa accccaacgt cctccggtga agcagctgcg    18300
gcggccaaaa aagctatgta ttttggcgtc gacgacctcc ctcttcaacc tcttttttc    18360 tgtccttctg tccgcatcaa atttctccat tccaaaccaa aaaaccatga tgatgatcat    18420
catcatggtg gtttcatgcc tcatccgtta aattctaccc ctcacttccc ttgtacaaga    18480
agccatgatc aacaaggcga gtcgttgctt gattgcgaca aagattatat ctgtaagctc    18540
cctgtaatcc ctcttttttg gtgcaacaat aaagaatttc gctatggcaa attcgattgt    18600
cgtgcatgta atgggaatat tttcagcaca agctatttta catgtctcca gtgtcaagga    18660
aagttccaca aagaatgtgt agagtctcca cttgagatca acacccttc ccacccttt      18720 cattctcttc gacttttcag tggttcaagt aatcagaagt gtagttgctg taaagtatat    18780
acaccaaata tgtattatca ttgtactacc tgcgagttga gtatgaatcc agtatgtgca    18840
atgaggccgg taccccttagt tgtagaccac ccaaaaagcc accccaccc tctctccttt    18900 ttccctacac aagcttctac agtttgcaat atttgtgcaa tgattaagaa gcttgatccc    18960
acatacatct gtatccaatg tgttttcgta atccataaag gttgtatggg tttcccacat    19020
atcataagga tatctcgtca cccccaccgt atctccttta cctcttctct tccacctgga    19080
aacttttcct gcggagtatg taggcaacaa gttgacaaca attatggtgc atactcttgc    19140
gagatatgtg atgattattt tgttcattcg aaatgttcat tacttccaag gatttgggac    19200
ggaaaagaac ttgaaggagt accagaagaa gatgataaga tagatgatgg ggagccgttc    19260
aagaggatag ctgatggaat aatactccat ccttttcata gtcaccatat gcggcttgag    19320
atcgacaaag cttatgatgg aaataagtat tgtcgaggat gtgcccttcc aatctatgaa    19380
ggtcaattct attcatgcat ggaatgcgac ttcatcctcc acgaaagctg tgcaaatgct    19440
ccacgcatga acggtatcc cttatatcca catccactta cactaaaagg taccaccacg     19500
agacatgaga atcaaaaagg taaagtttgt tgtagcgaat gccgacgtga ttgcaatggc    19560
ttcttctatg agtatcgtaa agaaaaagaa atcttccagc tagacctacg atgtgcctcg    19620
attattgaac catttgatta tcaaggccac caacatccct tatttctacc ttgggacaca    19680 aagaaaaga cacgatgtca aatgtgcaaa tacgaaagca aggagtcaaa gttaatttgc     19740
ttggaatgcg attattctat atgcttccgt tgtgctactt ttccgtacaa ggcaaggtat    19800
aaacatgata gtcatttcct cacaatttgt gatgggaaag aggaaagtga cgaaccagat    19860
tggtgtgagg tttgcgaagg caaaatagaa gaagtaaaag agacagggta taactggaaa    19920
ggtaaaaaaa cagaattgcg atactacaaa tgcaatgact gctgcaccgc tcttcatgtt    19980
```

```
gattgtttat ttgggagaga catgtacatt aaacctggtg aaacagaaaa agagtatctc    20040 tcttttccg atttctcatt tagcgaagac gtttggaaat ggatggatgt tcgggctctt     20100
ctcaatagtt ccctctctcg accaatttgc aatggatgca agtgccgttg tccattccca    20160
atattttaca aaggggacaa actaatattc tgttcttggt attgtcttaa gattgagcat    20220
ccaccgactc cctcccgtgt ttcttggtaa tttgaagtat ttttgacatt ttggctttgt    20280
tttttttttt tttttttagtt tcagttgtga gatgtaactc tttcatatgt gactttttatt   20340 ttcatttcct tgaattttt agccacaaga tcaattaagt tacaataaag gaaaatcatt    20400
gtcagttggc tttataatat tatagctttt acaagaaaca aatattatat cgcaaaattc    20460
agcaaaggag ataatttaat gaaatttctc tgttggagtt ttgatccttg aattgctatt    20520
ggaattcttg attgctctct ccatctcctt tgagttatct ttgtcttcct atgtttttt     20580 tggatgattt gacaaagccg tctagtccca acattcaatt tacatagcaa ggtttcgatt   20640
ttttcaaagg acatgcacca ccaagccaag aggagagaga actaaaattc ttaccgatca    20700
catcacactc catcttgatc tgaacaacac gcaatgccta agattaaaat cacatttcgt    20760
tacctgaatt tccgggaatt tctataaaaa aataaatatc gaagagagtt cacttactag    20820
aaaatataaa taatgctttg ttcctctaaa gagatctctt tcatgactag tccacatagc    20880
tcattttcat caaaacagag atctctaagc aagtgtaatc aggtgtcttg cttgactaat    20940
aagcatcgat cgtctccgag tctaatctct ttgtcccttt gactgttcct tttacccatt    21000
catatcctca ctacgtgttc atatctgcct cttccccacc caaccttcat ttttaatta     21060 attgttttc aaattttacg tactttacaa aactaactct ttaccaaatc aagataattt     21120
aataataact tgaaattgat tggagtgggg gatagagaaa gatatagaca catctgtaat    21180
aagagagacc atgtgttgtt acttgttttt gttgcagttg agtactgacc cataactgca    21240
aagtttgttg tccaaacaaa tactattatt ttctaattaa aatatataat aaatttaata    21300
cattgatata tatataaata tgtatatgta tatatatatt ttttgttcat gttgaattta    21360
atacagtaaa aggttaatta tatgttttcc aagtggtact tctttactct ttttttttaat   21420 tggcaataaa tcttttcaag tgggagtata ttttaaattt tttttttttt ttcacaatac    21480
tgattgcaac ttttttgttt gacaagttgt taactgttag gaatctcgga attgaagtca    21540
tgacatgttc tcgttcccag atgggatcgg aaaggcttgt tccaatcgag agagtgcatt    21600
tttgaataaa actatataat ctgtaatgaa aacaagatcc ggaagagacg gtctcctcta    21660
taatcaaaat aaaatataaa acgattgtaa agctattcca aatcaattac aaacgacttt    21720
ttttacaaca aagaatataa aaagaccaag tttagctgta ttctctagtt ttatattaaa    21780
tgaccagcta atatatatgt gcaattttt aaagagaaaa aataaaatata tatatata     21840 tatgtgtgca atgggtgaga tgaaagggaa gaagaatatc actatcaaaa aaaaaaaaa    21900 aaaatccaaa ttcccatttt agcagccatg agttctgtgg gtgtatttag taagaaggaa   21960
aaggatggaa tataattttg ggtattcaca ttagcacaaa caatagatcc aacctcctca    22020
aatttcaggc tcaattaaaa acgtagtggt ggacaagtaa tgatcaagat gagatgttat    22080
agtttcataa attaatagta atattgtgtt ggttttctaa taagtccaac aaatcggagg    22140
ggacataatt ttttttgttcc agttagaaac aactatatag ttgacatata tgttttaaaa   22200
tttagacttc attactaaga aaggaaagac ttataagagt ttagacttt agtgatttga     22260 gatcaatata ataaacgact attcttttta taataaagaa tttagaaaga ccaaaaataa    22320
```

```
ttagttgtta agaaaaaaaa cttagctgta ttgacaagtt tttatattaa atggttggct    22380
attaggcctg ttacggatcc ggatatccgg gattttgag gtatccggat ccggatccgt    22440
atccggcgga tccgtcattt cagtctctgg atccgtatct gccaacctcg gatattcggg    22500
atcctgaagt ctgtgaaaaa gtacgagtat ccgcggaccg gatccgatcc ggtttttttt    22560
tatcatcttc tttcctcccg aacacaagca accgaacttc accgccaaga ttctttccag    22620
aaaaaacagc tccaaatctg caacgaaaga gtgaatccaa cgccaagggg aagaagaaga    22680
gatagaggca gcggttgttt cggtggaggt tgaggatgag ggtgatttgg tggaggagga    22740
tgacgatttg gtgccatggt ggtagagatg gtcgtttggt ggaggctggt gtcgagagga    22800
atgagtgagg aagataaaag gattaggttt tttggaaaat gggccaagat atgggctgga    22860
aaatatcata attttaattt ttagtatggc ccaataaaac ccataaacat aaaacattga    22920
atattaccgg atccggatat ccggtcatat tttttatgat tatccggatc cggcggatat    22980
aaaatattac tatccgtatc cggaaccgtt tcacacggat atccggtttt tcggatcgga    23040
tcccggttcc agatacggat acccgcggat cccggatatt tgttccaggg ctattggcta    23100
tatatgcaag agggagaagg agaagaaaga tcacaaaaa aatttccaaa tccccattat    23160
cgaaaccatg agttccgtgg gagtattttg aaggaggaa attgatggaa aaccattttt    23220
ggtatacaca ttaacacaaa cagacaaccc aaactcctcc agtgaatcac tggccatgga    23280
ttctggtggc cataaactcc ctcttcaacc tctttttttca tgtcctagtt cacgtatcaa    23340
ttttcataag cgcaatcaca ttgatggtca tgagactcaa gagttttatc cattcaattg    23400
ttcccctcac ttccccagca aaagaaccag tactgatcaa gaaggcgaat ctttccttga    23460
ttgggacaac ccttatatct gtaagcttcc tgtagtcctt ctcttttggt gcaacactga    23520
acaacctgat ccagaagatt ttcggtgtgg tgcatgcggg cgtccaacgc tcagtgcaac    23580
ctattatgca tgccttatat gtgaaaaaat gttccacaaa gaatgcgtag agtctccatt    23640
cgagatcata catccttccc accctttttca ctctcttcga cttaccagtt ctccacagag    23700
tcaaaactgc atttgttgtc accattattt caacgacatt ttttatcact gttctacatg    23760
caagctcatt atgcatccga tctgtgcgat gaggtcaata ccctttgctg tagaccaccc    23820
aaaaagccat tcccaccctc tcaccttta ccctgcacaa gcttctttag tttgccatt    23880
ttgtgcctcg attaagaagt ttgatcccac atatatttgt atccaatgtg tcttcgcaat    23940
ccataaagat tgtcggggtt tcccgcatgt catcaggata tctcgccacc accaccgtat    24000
atctttacc tcttctcttc tatctggaac cttttcatgc ggagtctgca gagaacaagt    24060
tgacaacaat tatggtgcgt atgcttgcaa taaatgtgat ggttattttg ttcattcaaa    24120
atgtgcaata gatccaaagg tgtgggatgg aaaagaactc gaaggagtac cagaagaaaa    24180
tgataagata gatgatggtg agccgttcaa gaggatagct gatggaataa tactccaccc    24240
ttttcatagt caccatctgc aacttgagat ctttagagct tatgacgaaa atacgtattg    24300
tcgagggtgt gcgcttccga tctatgaagg tcaattctat tcatgcatgg aatgcgactt    24360
tatcctccat gaaagttgtg caaatgctcc atgcatgaag cgacatccct tacatccata    24420
tccacttaca cttttaaaca cggcatctcc tggtgaggaa agtgtaagcc agtgtactgc    24480
atgtaggcgt ctggttgttg gcttctacta ttttcattat ttagataaac atcacgaacg    24540
tatagcacta gacttacggt gtgcctcgat tatcgaacca tttgaattcc acggccacaa    24600
acatcccttta tacctacctt gggaggactc aaataaagtg acgcactgtc aaatctgcaa    24660
agaagatttt gatatggata gtttggaagt aaattgcatg gagtgcgatt atacgatatg    24720
```

```
tttccattgc gcttccttgc cagaaaaagt aaggtataag catgatagtc attttctcat    24780
gatctgtgat ggaaaagagg caagtgataa accatactgg tgtgagatct gtgaaggaaa    24840
aatagaagtt gtaaaagaaa aagcgaattc gggggacaaa aaaaaaaaaa ggttgccaac    24900
aaatagagac aaaaaagaaa ggaaaattta taaatgcaat gactgctgta ccactcttca    24960
tgctgaatgt ttacttggcc agacatttac ttcaaatctg ctcaaacaat agaatctgtt    25020
cagattcttc tcaacagttc tctctcccga ccaatatgcg atcgatgcta ctgccgctgt    25080
ccattcccaa tatattttaa agcggagaac aaatacttgt gttctcgcag ttgtagtccg    25140
aattccaatt aggcaatgta taacaaaaat gcgaggtact gacgacttac ccattttccc    25200
cctattttga tattccggct ctgtgagatg taattttcta tttcgtttat tattttttaa    25260
aattttatgt aagatgtaat tttcttttt tctcttttggt tttttttgtta attttttttc    25320
tgaacttacg tattatgttt ttttttttttt taatgttctt gcattttttaa gccacaatca    25380
aatatgcaga acacaagtaa aaaaaaatgc agagagttca cttctagatg tccctagctt    25440
tgtctgaaac ccagctataa acaatgtcca tccccctgaa tcctcaaaaa caagtcatgg    25500
gtatttcatg actagtcccc agctcattct tatcgaaaca gagaagttag actttgacgc    25560
tgattttgaa aactttcaaa tatattatat agaagtaatc catcatcagt ttcacatttc    25620
tctcgcctct tttgtgtttt tttttcttca catttgttgt acatatgaat atgatacaaa    25680
gagttgataa ataagaacct taaaatacag agactcaaca aatatatctg atctgtttat    25740
cacaccatta tttgatgagt tgtgttgtaa tatttgatct gatgaagtat aataatcctc    25800
tcagcgtttg tcatgtgagc tcagtgtata gttgatgttg tctgatataa tctattactc    25860
catcttcagt caagtattta accgataacc ctcgcgaaat gcattgcctg aaagaagcag    25920
aggaatgagc aagagaaatc attttttagt gtatatgaac tgttctcggg aaggataaat    25980
aaatctcaca ctaccttaat ctactcgaac tgatttgatt aggaacagta ttgtcaacga    26040
ttttgacgtt agcctgcgaa agaaatcgag ggggcactat tcagtaaacc atgtgcacaa    26100
tcacggactg atacagcaga gtcagaacag aaacctggta atacttacac agttttcgtt    26160
taagatttcg tcaccagaga tcatattttc aacatcttgt ccttctctac ggatgcacac    26220
aatgccataa tctttgcaaa tagttcttaa cttcaaaaac caagtgttga aaaggagca    26280
taactgtgag taaatttgat aaacacatct acgtttatat aacaatgcta ccttggttta    26340
cctgttcagg gatccaaaca ccgggagtgc agaaagatag cagtaaatcc gagccacata    26400
gtagcatgac tttgagagat tctagcatta gaataaattt gtgtttgtca tttgcgtagt    26460
ggctagcacg tatgataaaa acatagcaag caacactatt cagacgaccc agcaattact    26520
cccaaaatgt aagtgagata aactttgaat agaaagatgc taaaggcgac acaggacact    26580
tcttgcagtt atcttaccct cgggtacatg tcgatttgtt gttaagaaag tcttgacccct    26640
tgataaaacc gtcaaagttc gttggtagtt gctttgagat gcctgtagaa acagcttcca    26700
cattttttgta aacaacgcat tgttccacta aagagaactg attaaaagct tttcgaggaa    26760
taagaaagta cctcccacgg atcaaccatt acaaagtcag agctttgaca tgatacatta    26820
cacatctcta aacgatgttc tgcagataaa aggccctaca cataatctga tgaaattatt    26880
agttctaagg gaaactaaac agaatagtaa acagaagaac tttgggagct aaaaaagaaa    26940
aagaagctct tagtttcatc acacataaca tgtccattag cataggttca gaaaaaaaag    27000
agtcattatg gaaagaaact aagattctca agatgacaaa taccttcttc ttatatgcat    27060
```

```
cattaacagg agacatatat cctccaagaa catgaaatcc ttttgagcgt aattcatctc   27120
tcgccagctc tagcgacaaa aaaaggaag agaacttatc agtttgatgt aaagaaacat   27180
atacatttga acaaaggtc acagcaatgg acaagaatca acaattgaaa cctctaagtt   27240
ctgcagttca ttcttgtcat atgccggttt tataaaccaa aatatacaaa gctaacacaa   27300
tcatatactc aagaaacggt ttcactcaag aagtaaacaa caaggcatat aatcttaagc   27360
tacttttgac tataaaccag tattggattt tcccattgaa acgagtcaaa acactgatca   27420
ttatgcctca aattgtgaaa actttcggat tgatagaatc tgaaacgcca ttgataaaca   27480
tataaaaaaa tgaattatat atctactctg gtaaaagaac tgaccaaaca tgcgtaaatg   27540
catgaaagta ggaggattga aactcccagt tgccacaagc actacacaag ttttgtccct   27600
gtttcagaca aacaatcgaa aatattcaac acccggacgg aattttaata ataaacctgg   27660
tgagaatctc atcatcataa gtaaccaagc agatcaaatt tacaaaatca gaattttcac   27720
aaaaaagaca aatgaaggga atcaaaatcg agaataagct tcaaaattta ctcagtgttt   27780
gatccataag ataatttctc gactggtaac gggacatcca ttgaactctg atgattgaat   27840
ctcagtctct taatggtagc tccggcgaat gatcagggac agcgaaaata agacgacgac   27900
ggcgaaagta ttaaaagata gagagaaacg acatcgtatg aaaaaggttt gttaaaacga   27960
aacgttttac agctaacgag aagatagata ttagacacaa tacgaagccg tttaaaacta   28020
aacgcatcgt tcaggtagcg agggttaaaa aagctaaaaa agcttcattc tatttttttc   28080
agtgaaaaac gaaagcgaaa atgaaatctt tatccccaaa attttgaaat tcaaatccgc   28140
gctaacagtc tctctctctc tctcgctcta tctctagagt aggtcgtcgg cgatgttttc   28200
cgtcaaggag aatccgaggg ggaagacggc gaatgtgaag attgagaatc ttttcgttca   28260
gatctttgag aggaagaggc gaatcgtcga gcaggttcag caacaagtag atctctatga   28320 ccagcatttta gcttccaaat gcctactcgc cggagtatct cctccgtcgt ggctctggtc   28380
tccgtctcta ccttcccaaa cttccggtag ttgttaaatc tgattttag tgctcaattt   28440 cttgtccgtg atggtaaatg tagatttgtt tggctaatta gagcaaaatt gattagtagt   28500
cttagtggct attgagtaat gatgctgcga agttgtttga tacttaaacg ggaaatggat   28560
tgaaagttta taaagcgtat taccataaat ttgatgtcga attactgtga gaagatggaa   28620
ttgaaagatt agaaatggtg ttagggttca taatcacact ttgatgttga tttttctgtg   28680
ataagttaag gagcatttttg ttaaggctag tattaacgta cattgcgtgt atatctgttt   28740
cagttacgat tgaatagaag agtttctgtt tgcgattctt attgtgatgt ttgtttatat   28800
gtatacagag ttaaataagg aggagattat atcagaactt ctatttcctt catcaagacc   28860
ttccatcgtt tgtcctagca gtcgtcccttt ttcataccaa cggcctgtca ggtttctagc   28920
tgacaatgta gtaagacaag acctgacctc tgtggtaaat aacccgctag aagagcagtt   28980
gcttgaagag gaaccgcaac acaacctctc acacaactta gtcagacaag tttcgaatca   29040
ttctcatgag caggatgtta atattgcatc tcctagagat gtacatgaga aagagagatt   29100
gccagaaagt gtctcaatcg attgcagaga gaatcaaagt tgttcatctc ccgaacactc   29160
caagaatcag agagttgaaa ctaatcttga tgctacatct cctggatgta gccaagggga   29220
aaaggttccc aaatgtgtct caactactgg ttgtaagcgg aaatcttcat ctcttggtta   29280
ttgtcaagag gaaattgaac cagacacttg cattgaccct ggattatcac ttgctaagat   29340
gcagagatca aggtcacgtc aaaaagcttt ggagcttcgt agtagtgcaa aagcgtcaaa   29400
aagccgttca aacagtagaa atgagctcaa accttctccg ggtggtgata taggctttgg   29460
```

```
gattgcttca ttaaggtctg atagtgttag tgagataaag ttatttaagc atgatgaaaa   29520
tgatgaagag tgtcgagaag aagtggagaa cagtaattct caaggtaaaa gaggagatca   29580
atgtattaag attagtgtac ctacagagtc ttttaccttg catcatgaag tggattcagt   29640
gtcaatatct tcaagtggtg atgcttatgc ttctattgta ccagaatgtc tactcgagtc   29700
tggtcatgtg aatgacattg atatattaca gtccattgag acaattgatg aagcgtctgg   29760
caaagtagat gagcaagtgg atgatcccaa aagcagaagt tgctatgaaa cagcttatct   29820
cgatggaagt acaagatcta aaagctcaat tcaagataac tccaagagga aacatcaaaa   29880
atcaagcaac tccttttctg gtaattttct gttaacaaat tcaaatccct ctcactgggc   29940
tgatcatgaa gtagaattac ctcaagcaat aactacgact agtgaagttt ctatggtgac   30000
agatgcggga acgagcatct ttcagtctga aatcattgca agatctagaa gtaatgctcg   30060
agaaaataga tccaagaccg agcattcagg ctctgttgag tcttcttcaa ttaacttgga   30120
gccaagagat tcaattccag tactgcaagg tagccatgta aaagattcac tgaatccctc   30180
tagtgttgat gctgaaggtt tagtagttga aatatattact agcagcgatc aatcaaaaga   30240
aacgggtgaa tgtgttgaca ctaacagatg ttcaagtgct gaaagggtaa gccaaactgg   30300
tatctcccca gatgagacca catttgcggg tgcaatccaa gactctatat cccagatcga   30360
gcttttgagc tttgttgagt cctcttcaat tgaactgcag tcgagacact cagtcaagca   30420
atcagacgat gaaagtgtat tgttgaagcc cgttactgtt aatggcgaag ctttattagt   30480
ggaggaagat aacaatggtg agtcaactga aattagcggt atttcaaaat ctagaagttt   30540
aagccaaact gacatcacgg tagttttgcc agtggtggtg gaatctattc ttaatgaaag   30600
tggtactccg gaaaaattga ttgaccattc taaaagatgt gatatcagtt gtgggtccaa   30660
ggaagtacag ccactgggtt cattgaccga agtggggagt aaccaaagcc atggaataat   30720
tagtagggca agaagctcac tcatagaaga ggaatcagca aatgactata aggctctttc   30780
tgatgggtct aatcataaat cggctgacaa acaacttgaa gttagagaag gaaattcatt   30840
gctgagaacc cctgatcgcc ctgtttttgt ggacaacttc gatgaggttc cagagaatag   30900
tcgagaaaaa tcaagcatgg agaaggtccc caccccagca cccaccgcaa gggtgtttga   30960
tgtcccatct ctcactgatt ctggagtaaa tttatcggca aacaatgaaa tgaatgacat   31020
tgaagatcac aatgggttaa acatagaaat ggtagcagaa atggaatcgt atgcaagcca   31080
ccctggctta aaagtgggag agaatgaacc tacagagtca aatacattca ctggccatat   31140
agatgcattg acaaagagac ctcaacatga acatcctct gaaaaagctg ttcccccaat   31200
taaaagagat gtaacatgta cagaagcaga tgaatgtcat gatctagaga gcccgattca   31260
agaatttttc tgctctagtt cccccatggg gggttccatg cggcagaata agcggagaag   31320
aatcctggaa aaaccaacta gaagagagct ttcgtcaagt ccagggggtga atattctttc   31380 cctaagtctt gggacagctc aatatatgag agtctttaac tgctcttttcc ttctaaatgt   31440 aattaagatg cttttttgaat catgggattt tatatgttgc agggagacat tctcgagtca   31500
gattatgtta gggaagcagt acatcatagg gaggaagccg catgtcacaa cgtcgataac   31560
tatgacgttg agttacagaa gttgattgga tctgcatctt cacatcacta tagtgttgag   31620
ttacaaaaaa tgattggatc tgcatcgtca gctgagttac gatttgaaga ggtatgttca   31680
ttatttctct gtattcttat gtataatgtc ttctaaatag taatctcttt ctcctgaagt   31740
tttaatcgct cataaaaaaa caaagatatc ttcattccat gctctaaaag ggaaatagac   31800
```

```
aattatacca tcaattataa gctgtactat tgttattact gtaatgagaa aatctcattc  31860
taggtctaag tgtcgtagta ttaagcacct ctcaagctac acatgtatat aaaaacctcc  31920
ataaaagtta tgggtcaaaa gctaaatgta attaagatgc tttttgaatc atgggatttt  31980
ataatgttgc agggagacat tctcgagtca gattatgtta gagaagcagt acatcatagg  32040
gaggaagccg catgtcacaa cgtcgataac tatgacgttg agttacagaa gttgattgga  32100
tctgcatctt cacatcacta tagtgttgag ttacaaaaaa tgattggatc tgcatcgtca  32160
gctgagttac gatttgaaga ggtctgttca ttatttctct gtattcttat gtttaatgtc  32220
ttctaaatag taacctcttt ctcctgaagt tttaatcgct cattaaaaaa aaaaagatat  32280
cttcgttcca tgctctaaaa gggaaataga caattaaacc ttcaattaaa agctgtacta  32340
ttgttattac taatgagaaa atctcattct aggtctaagt gtcgtagtat taagcatctc  32400
tcaagctaca catgtatata aaaagctcca caaaaattat cggtcaaaat ctgaaatcct  32460
aattaagtct cagattagta gtgctcatcc ttgtgtgtct ttatttctat gactctactg  32520
attgtctgcc aagagatgaa actgcagtac agttcaagct cttagttcca taatgattta  32580
tcttgttcta tatgatgtgc aattaaccag aacatggatg tttacagagt tatttactca  32640
aggaagctgg attgatgagt cctgcctcgc tttcctacag aacagaacag ctaagtgtac  32700
agaggagtca aattgctcca gatcacagag ttggatcaga aaatattaac tttttttccat  32760 atgctggtga aacctcacat ggattagcta gttgtattgt tcgcgactca gatagttctc  32820
cttgcttaac acccttgggt ttgataagct cagacgatgg aagcccccct gtcttggagg  32880
gttttattat ccagactgat gatgaaaatc aaagcggctc caaaaaccag ttaaatcatg  32940
acagcttcca acttccaaga actacagcag aaagtgcagc catgatagag cagatttgca  33000
agtctgcttg catgaacact ccgtcattac atctggctaa acatttaag ttcgatgaaa  33060 aactagactt ggatcagtct gttttcaaccg agctgtttga tggcatgttt ttcagtcaga  33120
atctcgaggg tagctctgtc tttgataact tggggattaa ccatgattat acaggaagat  33180
cgtacactga ctcttgcct ggtactggct catctgctga ggctaggaat ccttgcatgt  33240
caccaactga gaagctgtgg tatagaagtt tgcaaaagtc ttccagttca gagaaacgaa  33300
gcactcagac accagaccta ccttgcatta gcgaagagaa tgagaacata gaagaggaag  33360
ctgagaactt atgtacgaac actccaaagt ctatgaggtc agagaagcga ggaagttcaa  33420
ttccggaact tccttgcata gctgaagaga acgaaaacat agatgagata tctgatgctg  33480
tcaatgaagc atctggttct gaaagggaga atgtgtctgc tgaaaggaaa cctcttggtg  33540
atgttaatga agatcctatg aagcttcttc catctgtttc tgaagccaag attcctgccg  33600
atagacagag tctagactct gtcagtactg cattcagctt ttcagctaag tgcaacagtg  33660
tcaaaagtaa agtgggaaag ctgagtaacc gaagattcac gggtaaaggt aaagagaacc  33720 aagtggagc aggtgctaaa agaaatgtta accgcctag tagcaggttc agtaagccta  33780
agttgtcttg caactcgagt ttgcaactg taggtccacg gttacaagaa aaagaaccta  33840
ggcacaacaa cattgtctca aacatcactt cgttcgttcc actagtgcag cagcaaaaac  33900
cagcacctgc actaattaca ggtaattgtt atttctttcg agtatgaggc ttttgaaatt  33960
tccaattaat tggaggtatc attttaccat cttgcgctag ttattcacct gatttgcccc  34020
tatttatgtt tcctccaggg aaaagggatg tcaaagtaaa ggccctggag gctgctgagg  34080
cttcaaaacg tattgctgaa cagaaagaga atgatcgtaa gctgaagaag gaagctatga  34140
agcttgaacg ggcaaaacag gaacaggaaa atctgaaaaa gcaagagata gagaagaaaa  34200
```

-continued

```
agaaagaaga agatcgaaag aaaaaggagg cagaaatggc ttggaagcag gagatggaaa    34260
agaaaaagaa agaagaagaa aggaagagaa aggagtttga aatggctgat aggaaaaggc    34320
agagggaaga agaagacaaa aggttgaagg aagctaaaaa aagacaacgc attgcagatt    34380
ttcaaagaca acaaagagag gctgatgaaa agcttcaagc tgaaaagaa ttgaaaagac     34440 aagctatggt aagagccctt ctcttgttct gttcttcaaa actttgtttg actattgtgg    34500
tgtaggagat tttgctaagt taaaaataac gacatttta ggatgcgaga ataaaagcac     34560
aaaaggaact caaagaagac caaaataatg ctgagaaaac caggcaagcg aattctagga    34620
tcccagcggt gagatcaaag agtaattcta gtgatgatac caatgcttca agaagctcta    34680
gagaaaatga tttcaaggta taagtctctc atcttttgta gacaatttag agatgaaacc    34740
aatcataatt gatgacaata gttgtgcttg caggtgataa gcaatccagg gaacatgtct    34800
gaagaagcca acatgggaat tgaagaaatg gaagagtcgt acaacatctc tccatacaaa    34860
tgctcagatg acgaagatga agaggaagac gacaatgacg acatgtccaa caaaaattc    34920 gctcctactt gggccaggtt ttgtttctga attgctctct cattcgttaa tgtttatctc    34980
tcattagtca ttatcatttg tttaccccaa cgcttcttat ctacacagca agagcaatgt    35040
acggctcgct gtcatttccc aacaaaacat tgatcccgat gttacttttc ctgcaaaaag    35100
cgcctgtgat ataagtaacg gtaagatatc ttgattacat tttatagaaa aaagtgtca    35160 tagttttcgc catacttatg gataagtttt tgttatgaat ctctcagttc ttttgccgcg    35220
aaagttccag tcgagatagc ataaacaacg agaagccaaa ggtcagattc tcagtgacat    35280
taaaaccaca aacaaagtaa gtatctatgt gtttcaagtt tcttcttaac ttttgctgaa    35340
aatgaggaac ataaaccata gtatctttaa gcttaagatt ccttttgct ttcttatgta     35400 tcagtgaatg ggtaatgtaa taattaatta gtcaatcccc attgacgctc atgttcatac    35460
ataacggcta cttccatttt gtaaaatatt cataggttct gttgattttc ctagtggaaa    35520
gagccaggtg ctgaaagcaa gagatttgtt ctttttcaat ataaccaaat tctcactact    35580
tttcaatgtc gacttcgtca aaataacttt tggataagaa agaaaaaaaa taacttttg     35640 gatcacgatc gcttaactat atttattatt taataactgt cgaattcaga acttaaataa    35700
agtagtcaca aatcacaatt gtgggattta ttatttagca ctcgctcact tttgcacaac    35760
ggattgaaaa atgctgttga acttgttaaa tatgtttact gagatggtat aatcacagaa    35820
attcactagt atcaatttca gtatctgttt caaaagtagt gaatgctttt tctagtctac    35880
aaaacagtta acagtaaaca gtcaaccata gtgggtgagt caaattgagt tatatgataa    35940
aatagacaga aacttaaatg aagtaaaaga tcaataatat ttctattcac gtggtggcgc    36000
tatatagatt ccattaaaac ggtcagtttt gattttgcg tcccatgtac cagacccac      36060 ccgacccgct ccaccacttt tgttcccacc cttaaaaacg acagcgtttc acaccaacct    36120
taataaccgt tgccacagta aaaatactat aatacctca ccttcttcat aatcatcaat     36180
tcgaatccat tttcccacca cagtaatacc gaaactttct cttctctctc tctctaatgt    36240
ctctatcaag aaagcttctt gttatcttct tcacatggat aacagctcta tccatgtcga    36300
aaccaatctt cgtatcatcc gataacatga atttcacatt caaatccttc acaatccgta    36360
acctcacatt cctcggagat tcacatctcc gaaacggtgt cgttgggctc acaagagagc    36420
taggtgttcc cgatacaagc tccggtacag taatctacaa caatccgatc cgtttctacg    36480
atccggattc aaacaccacg gcgtctttct ccactcactt ctccttcacc gttcaaaact    36540
```

-continued

```
taaacccaga tccaacctcc gccggtgacg gactcgcttt cttcctctct cacgacaacg      36600
atactttagg aagtcccggt ggttacttag gtctcgtcaa ttcctctcag ccgatgaaga      36660
atcgattcgt cgctatcgaa ttcgatacga aattggatc                             36699
```

```
<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:  PCR primer

<400> SEQUENCE: 9
aacttgattt gggtgatggt tcacgtagtg                                         30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:  PCR primer

<400> SEQUENCE: 10
gccctgatag acggttttc gcccttgac                                          30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:  PCR primer

<400> SEQUENCE: 11
caatccatct tgttcaatca tgcgaaacga                                         30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:  PCR primer

<400> SEQUENCE: 12
cgacttttga acgcgcaata atggtttctg                                         30

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:  PCR primer

<400> SEQUENCE: 13
aggtcttgcg aaggatagtg ggattgt                                            27

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence:  PCR primer

<400> SEQUENCE: 14
atgtatgcta ttggtggtag tg                                                 22
```

-continued

```
<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:  PCR primer

<400> SEQUENCE: 15
gagaggccca atataaaata cgag                                              24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:  PCR primer

<400> SEQUENCE: 16
ataatccgga ctggaaaaag aaac                                              24

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:  PCR primer

<400> SEQUENCE: 17
atcccgggaa tacaagaact tgacagctcc                                        30

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence:  PCR primer

<400> SEQUENCE: 18
tacccgggga agcagagatc ctc                                               23
```